(12) United States Patent
Baroudy et al.

(10) Patent No.: US 6,689,765 B2
(45) Date of Patent: Feb. 10, 2004

(54) PIPERAZINE DERIVATIVES USEFUL AS CCR5 ANTAGONISTS

(75) Inventors: Bahige M. Baroudy, Westfield, NJ (US); John W. Clader, Cranford, NJ (US); Hubert B. Josien, Jersey City, NJ (US); Stuart W. McCombie, Caldwell, NJ (US); Brian A. McKittrick, Bloomfield, NJ (US); Michael W. Miller, Westfield, NJ (US); Bernard R. Neustadt, West Orange, NJ (US); Anandan Palani, Kenilworth, NJ (US); Elizabeth M. Smith, Verona, NJ (US); Ruo Steensma, Weehawken, NJ (US); Jayaram R. Tagat, Westfield, NJ (US); Susan F. Vice, Mountainside, NJ (US); Mark A. Laughlin, Edison, NJ (US); Eric Gilbert, Scotch Plains, NJ (US); Marc A. Labroli, Mount Laurel, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/061,011

(22) Filed: Jan. 30, 2002

(65) Prior Publication Data

US 2003/0069252 A1 Apr. 10, 2003

Related U.S. Application Data

(62) Division of application No. 09/562,814, filed on May 1, 2000, now Pat. No. 6,391,865.
(60) Provisional application No. 60/132,509, filed on May 4, 1999.

(51) Int. Cl.[7] ............... A61K 31/695; A61K 31/69; A61K 31/497; A61K 38/00; A61K 31/70
(52) U.S. Cl. ............... 514/63; 514/64; 514/252.12; 514/252.13; 514/252.19; 514/253.01; 514/253.1; 514/253.11; 514/2; 514/42; 514/43; 514/45; 514/49; 514/220; 514/262; 514/263
(58) Field of Search .............. 514/252.12, 252.13, 514/253.01, 253.1, 253.11, 252.19, 63, 64, 2, 42, 43–52, 220, 262, 263

(56) References Cited

U.S. PATENT DOCUMENTS

| | | | |
|---|---|---|---|
| 5,368,854 A | 11/1994 | Rennick | 424/85.2 |
| 5,883,096 A | 3/1999 | Lowe et al. | 514/252 |
| 5,889,006 A | 3/1999 | Lowe et al. | 519/252 |
| 6,037,352 A | 3/2000 | Lowe et al. | 514/316 |
| 6,066,636 A | 5/2000 | Kozlowski et al. | 514/252 |

FOREIGN PATENT DOCUMENTS

| | | |
|---|---|---|
| WO | WO 94/18192 | 8/1994 |
| WO | WO 96/26196 | 8/1996 |
| WO | WO 97/16440 | 5/1997 |
| WO | WO 98/05292 | 2/1998 |
| WO | WO 99/04794 | 2/1999 |
| WO | WO 00/00488 | 1/2000 |

OTHER PUBLICATIONS

Vandamme et al, *Antiviral Chemistry and Chemotherapy*, 9 (1998) p. 187–203.
Connor et al, *Virology*, 206 (1995) p. 935–944.
Plater–Zyberk et al, *Immunol. Let.*, 57 (1997) p. 117–120.
Boiardi et al, *Clinical and Experimental Rheumatology*, 17, (1999) p. 419–425.
Hatano et al, *Clin. Exp. Immunol.*, 117 (1999) p. 237–243.
Raychaudhuri et al, *International J. of Immunopharmacology*, 20 (1998) p. 661–667.
Chihara et al, *J. Allergy Clin. Immunol.*, 100, 6, part 2 (1997) p. S52–S55.
Beck et al, *J. Immunol.*, 159, 6 (1997) p. 2962–72.
Thea et al, *J. Org. Chem.*, 50 (1985) p. 1867–1872.
Deng et al, *Nature*, 381 (1996) p. 661–666.
Dragic et al, *Nature*, 381 (1996) p. 667–673.
Liu et al, *Cell*, 86 (1996) p. 367–377.

*Primary Examiner*—Shengjun Wang
(74) *Attorney, Agent, or Firm*—Anita W. Magatti

(57) ABSTRACT

The use of CCR5 antagonists of the formula

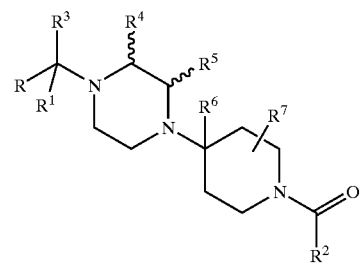

I or a pharmaceutically acceptable salt thereof, wherein
  R is optionally substituted phenyl, pyridyl, thiophenyl or naphthyl;
  $R^1$ is hydrogen or alkyl;
  $R^2$ is substituted phenyl, substituted heteroaryl, naphthyl, fluorenyl, diphenylmethyl or optionally substituted phenyl- or heteroaryl-alkyl;
  $R^3$ is hydrogen, alkyl, alkoxyalkyl, cycloalkyl, cycloalkylalkyl, or optionally substituted phenyl, phenylalkyl, naphthyl, naphthylalkyl, heteroaryl or heteroarylalkyl;
  $R^4$, $R^5$ and $R^7$ are hydrogen or alkyl;
  $R^6$ is hydrogen, alkyl or alkenyl;
for the treatment of HIV, solid organ transplant rejection, graft v, host disease, arthritis, rheumatoid arthritis, inflammatory bowel disease, atopic dermatitis, psoriasis, asthma, allergies or multiple sclerosis is disclosed, as well as novel compounds, pharmaceutical compositions comprising them, and the combination of CCR5 antagonists of the invention in combination with antiviral agents useful in the treatment of HIV or agents useful in the treatment of inflammatory diseases.

12 Claims, No Drawings

PIPERAZINE DERIVATIVES USEFUL AS CCR5 ANTAGONISTS

CROSS REFERENCE TO RELATED APPLICATIONS

This application is a division of U.S. Ser. No. 09/562,814, filed May 1, 2000, now U.S. Pat. No. 6,391,865 B1, which claims the benefit of U.S. Provisional Application No. 60/132,509, filed May 4, 1999.

BACKGROUND

The present invention relates to piperazine derivatives useful as selective CCR5 antagonists, pharmaceutical compositions containing the compounds, and methods of treatment using the compounds. The invention also relates to the use of a combination of a CCR5 antagonist of this invention and one or more antiviral or other agents useful in the treatment of Human Immunodeficiency Virus (HIV). The invention further relates to the use of a CCR-5 antagonist of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

The global health crisis caused by HIV, the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR-5 receptors have been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Related piperazine derivatives which are muscarinic antagonists useful in the treatment of cognitive disorders such as Alzheimer's disease are disclosed in U.S. Pat. Nos 5,883,096; 6,037,352; 5,889,006.

A-M. Vandamme et al., *Antiviral Chemistry & Chemotherapy*, 9:187–203 (1998) disclose current clinical treatments of HIV-1 infections in man including at least triple drug combinations or so-called Highly Active Anti-retroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention relates to the treatment of HIV comprising administering to a mammal in need of such treatment an effective amount of a CCR5 antagonist represented by the structural formula I:

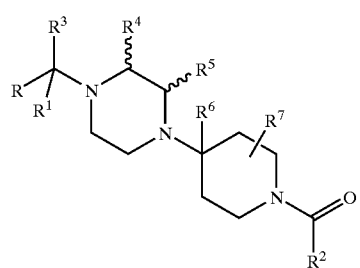

or a pharmaceutically acceptable salt thereof, wherein

R is $R^8$-phenyl, $R^8$-pyridyl, $R^8$-thiophenyl or $R^8$-naphthyl;

$R^1$ is hydrogen or $C_1$–$C_6$ alkyl;

$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide; $R^{12}$, $R^{13}$-substituted 5-membered heteroaryl; naphthyl; fluorenyl; diphenyl-methyl

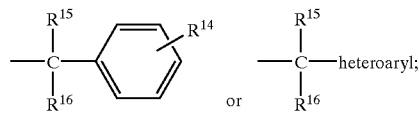

$R^3$ is hydrogen, $C_1$–$C_6$ alkyl, $(C_1$–$C_6)$alkoxy$(C_1$–$C_6)$ alkyl, $C_3$–$C_{10}$ cycloalkyl, $C_3$–$C_{10}$ cycloalkyl$(C_1$–$C_6)$ alkyl, $R^8$-phenyl, $R^8$-phenyl$(C_1$–$C_6)$alkyl, $R^8$-naphthyl, $R^8$-naphthyl$(C_1$–$C_6)$alkyl, $R^8$-heteroaryl or $R^8$-heteroaryl$(C_1$–$C_6)$alkyl;

$R^4$, $R^5$, $R^7$ and $R^{13}$ are independently selected from the group consisting of hydrogen and $(C_1$–$C_6)$-alkyl;

$R^6$ is hydrogen, $C_1$–$C_6$ alkyl or $C_2$–$C_6$ alkenyl;

$R^8$ is 1 to 3 substituents independently selected from the group consisting of hydrogen, halogen, $C_1$–$C_6$ alkyl, $C_1$–$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C$(=$NOCH_3$), $CH_3C$(=$NOCH_2CH_3$),

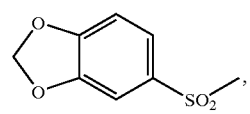

—$NH_2$, —$NHCOCF_3$, —$NHCONH(C_1$–$C_6$ alkyl), —$NHCO(C_1$–$C_6$ alkyl), —$NHSO_2(C_1$–$C_6$ alkyl), 5-membered heteroaryl and

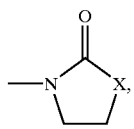

wherein X is —O—, —NH— or —N(CH$_3$)—;

R$^9$ and R$^{10}$ are independently selected from the group consisting of (C$_1$–C$_6$)alkyl, halogen, —NR$^{17}$R$^{18}$, —OH, —CF$_3$, —OCH$_3$, —O-acyl, —OCF$_3$ and —Si(CH$_3$)$_3$;

R$^{11}$ is R$^9$, hydrogen, phenyl, —NO$_2$, —CN, —CH$_2$F, —CHF$_2$, —CHO, —CH=NOR$^{17}$, pyridyl, pyridyl N-oxide, pyrimidinyl, pyrazinyl, —N(R$^{17}$)CONR$^{18}$R$^{19}$, —NHCONH(chloro-(C$_1$–C$_6$)alkyl), —NHCONH((C$_3$–C$_1$)cycloalkyl(C$_1$–C$_6$)alkyl), —NHCO(C$_1$–C$_6$)alkyl, —NHCOCF$_3$, —NHSO$_2$N((C$_1$–C$_6$)alkyl)$_2$, —NHSO$_2$(C$_1$–C$_6$)alkyl, —N(SO$_2$CF$_3$)$_2$, —NHCO$_2$(C$_1$–C$_6$)alkyl, C$_3$–C$_{10}$ cycloalkyl, —SR$^{20}$, —SOR$^{20}$, —SO$_2$R$^{20}$, —SO$_2$NH(C$_{1-C6}$ alkyl), —OSO$_2$(C$_1$–C$_6$)alkyl, —OSO$_2$CF$_3$, hydroxy(C$_1$–C$_6$)alkyl, —CON R$^{17}$R$^{18}$, —CON(CH$_2$CH$_2$—O— CH$_3$)$_2$, —OCONH(C$_1$–C$_6$)alkyl, —CO$_2$R$^{17}$, —Si(CH$_3$)$_3$ or —B(OC(CH$_3$)$_2$)

R$^{12}$ is (C$_1$–C$_6$)alkyl, —NH$_2$ or R$^{14}$-phenyl;

R$^{14}$ is 1 to 3 substituents independently selected from the group consisting of hydrogen, (C$_1$–C$_6$) alkyl, —CF$_3$, —CO$_2$R$_{17}$, —CN, (C$_1$–C$_6$)alkoxy and halogen;

R$^{15}$ and R$^{16}$ are independently selected from the group consisting of hydrogen and C$_1$–C$_6$ alkyl, or R$^{15}$ and R$^{16}$ together are a C$_2$–C$_5$ alkylene group and with the carbon to which they are attached form a Spiro ring of 3 to 6 carbon atoms;

R$^{17}$, R$^{18}$ and R$^{19}$ are independently selected from the group consisting of H and C$_1$–C$_6$ alkyl; and R$^{20}$ is C$_1$–C$_6$ alkyl or phenyl.

Preferred are compounds of formula I wherein R is R$^8$-phenyl or R$^8$-naphthyl, especially wherein R$^8$ is a single substituent, and especially wherein the R$^8$ substituent is in the 4-position. For R$^8$-phenyl, preferred R$^8$ substituents are —CF$_3$, —OCF$_3$, CH$_3$SO$_2$—, CH$_3$CO—, CH$_3$C(=NOCH$_3$)—, Br and I. For R$^8$-naphthyl, R$^8$ is preferably C$_1$–C$_6$ alkoxy. Also preferred are compounds of formula I wherein R$^3$ is hydrogen, (C$_1$–C$_6$) alkyl, R$^8$-phenyl. R$^8$-benzyl or R$^8$-pyridyl; more preferred definitions for R$^3$ are methyl, ethyl, phenyl, benzyl and pyridyl. R$^1$ is preferably hydrogen. For compounds of formula 1, R$^6$ is preferably hydrogen or methyl, especially methyl. R$^4$ is preferably methyl; R$^5$ and R$^7$ are each preferably hydrogen.

In compounds of formula 1, R$^2$ is preferably R$^9$, R$^{10}$, R$^{11}$-phenyl, R$^9$, R$^{10}$, R$^{11}$-pyridyl or an N-oxide thereof, or R$^9$, R$^{10}$, R$^{11}$-pyrimidyl. When R$^2$ is pyridyl, it is preferably 3- or 4-pyridyl, and when pyrimidyl, it is preferably 5-pyrimidyl. The R$^9$ and R$^{10}$ substituents are preferably attached to carbon ring members adjacent to the carbon joining the ring to the rest of the molecule and the R$^{11}$ substituent can be attached to any of the remaining unsubstituted carbon ring members, for example as shown in the following structures:

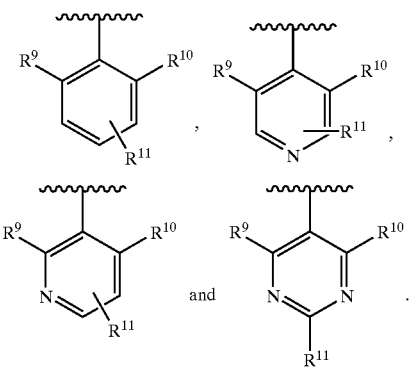

Preferred R$^9$ and R$^{10}$ substituents are: (C$_1$–C$_6$)alkyl, especially methyl; halogen, especially chloro or bromo, —OH and —NH$_2$. When R$^2$ is phenyl, R$^{11}$ is preferably hydrogen or —OH; when R$^2$ is pyridyl, R$^{11}$ is preferably hydrogen; and when R$^2$ is pyrimidyl, R$^{11}$ is preferably hydrogen, methyl or phenyl. Examples of particularly preferred R$^2$ groups are as follows:

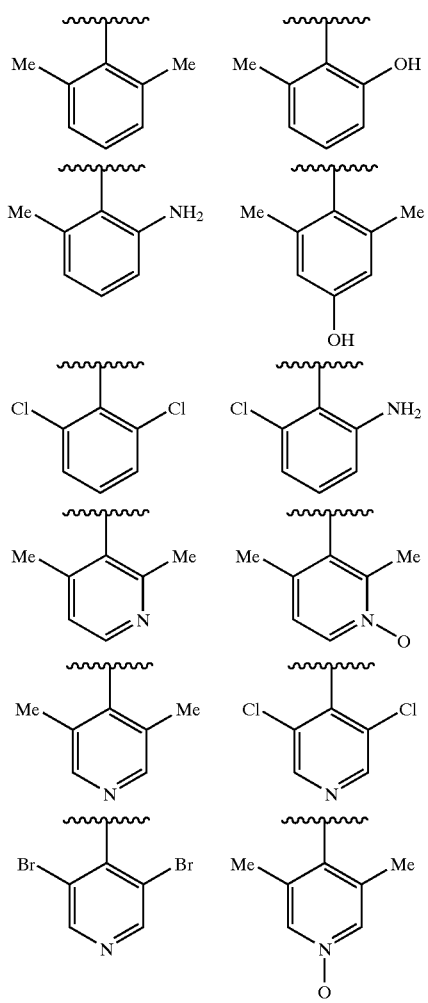

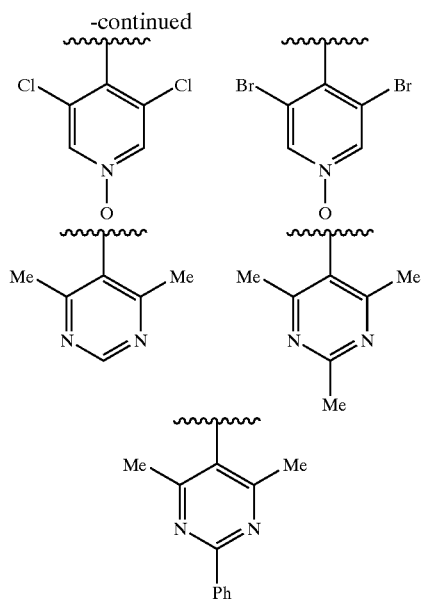

Also claimed are novel CCR5 antagonist compounds represented by the structural formula II

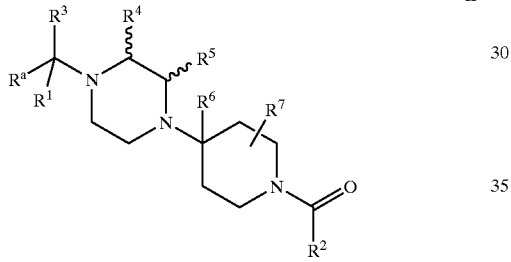

or a pharmaceutically acceptable salt thereof, wherein
(1) $R^a$ is $R^{8a}$-phenyl, $R^{8b}$-pyridyl, $R^{8b}$-thiophenyl or $R^8$-naphthyl;
$R^1$ is hydrogen or $C_1$–$C_6$ alkyl;
$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide; $R^{12}$, $R^{13}$-substituted 5-membered heteroaryl; naphthyl; fluorenyl; diphenylmethyl,

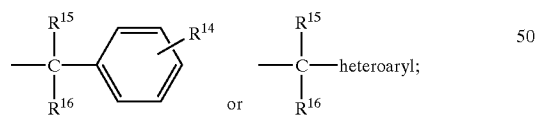

$R^3$ is hydrogen, $C_1$–$C_6$ alkyl, ($C_1$–$C_6$)alkoxy($C_1$–$C_6$) alkyl, $C_3$–$C_{10}$ cycloalkyl, $C_3$–$C_{10}$ cycloalkyl($C_1$–$C_6$) alkyl, $R^8$-phenyl, $R^8$-phenyl($C_1$–$C_6$)alkyl, $R^8$-naphthyl, $R^8$-naphthyl($C_1$–$C_6$)alkyl, $R^8$-heteroaryl or $R^8$-heteroaryl($C_1$–$C_6$)alkyl;
$R^4$, $R^5$, $R^7$ and $R^{13}$ are independently selected from the group consisting of hydrogen and ($C_1$–$C_6$)-alkyl;
$R^6$ is hydrogen, $C_1$–$C_6$ alkyl or $C_2$–$C_6$ alkenyl;
$R^8$ is 1 to 3 substituents independently selected from the group consisting of hydrogen, halogen, $C_1$–$C_6$ alkyl, $C_1$–$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$, $CH_3C(=NOCH_2CH_3)$,

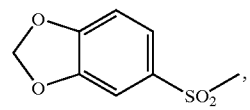

—$NH_2$, —$NHCOCF_3$, —$NHCONH(C_1$–$C_6$ alkyl), —$NHCO(C_1$–$C_6$ alkyl), —$NHSO_2(C_1$–$C_6$ alkyl), 5-membered heteroaryl and

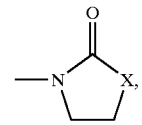

wherein X is —O—, —NH— or —N($CH_3$)—;
$R^{8a}$ is 1 to 3 substituents independently selected from the group consisting of hydrogen, halogen, —$CF_3$, $CF_3O$—, —CN, $CF_3SO_2$—, $R^{14}$-phenyl, —$NHCOCF_3$, 5-membered heteroaryl and

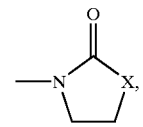

wherein X is as defined above;
$R^{8b}$ is 1 to 3 substituents independently selected from the group consisting of hydrogen, halogen, —$CF_3$, $CF_3O$—, $CH_3C(O)$—, —CN, $CF_3SO_2$—, $R^{14}$-benzyl, $CH_3C(=NOCH_3)$, $CH_3C(=NOCH_2CH_3)$,

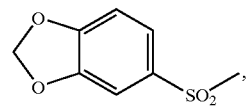

—$NHCOCF_3$, 5-membered heteroaryl and

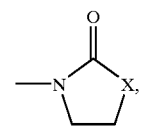

wherein X is as defined above;
$R^9$ and $R^{10}$ are independently selected from the group consisting of ($C_1$–$C_6$)alkyl, halogen, —$NR^{17}R^{18}$, —OH, —$CF_3$, —$OCH_3$, —O-acyl, —$OCF_3$ and —$Si(CH_3)_3$;
$R^{11}$ is $R^9$, hydrogen, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —N($R^{17}$) $CONR^{18}R^{19}$, —NHCONH(chloro-($C_1$–$C_6$)alkyl), —NHCONH(($C_3$–$C_1$)cycloalkyl($C_1$–$C_6$)alkyl), —NHCO($C_1$–$C_6$)alkyl, —$NHCOCF_3$, —$NHSO_2N$ (($C_1$–$C_6$)alkyl)$_2$, —$NHSO_2(C_{1-C6})$alkyl, —N($SO_2CF_3$)$_2$, —$NHCO_2(C_1$–$C_6$cycloalkyl, —$SR^{20}$, —SO ,—$SO_2R^{20}$,—$SO_2NH(C_1$–$C_6$ alkyl), —$OSO_2(C_1C_6)$alkyl, —$OSO_2CF_3$, hydroxy($C_1$–$C_6$) alkyl, —CON $R^{17}R^{18}$, —$CON(CH_2CH_2$—O—$CH_3)_2$, —$OCONH(C_1$–$C_6)$alkyl, —$CO_2R^{17}$, —$Si(CH_3)_3$ or —$B(OC(CH_3)_2)_2$;
$R^{12}$ is ($C_1$–$C_6$)alkyl, —$NH_2$ or $R^{14}$-phenyl;

$R^{14}$ is 1 to 3 substituents independently selected from the group consisting of hydrogen, ($C_1$–$C_6$) alkyl, —$CF_3$, —$CO_2R_{17}$, —CN, ($C_1$–$C_6$)alkoxy and halogen;

$R^{15}$ and $R^{16}$ are independently selected from the group consisting of hydrogen and $C_1$–$C_6$ alkyl, or $R^{15}$ and $R^{16}$ together are a $C_2$–$C_5$ alkylene group and with the carbon to which they are attached form a Spiro ring of 3 to 6 carbon atoms;

$R^{17}$, $R^{18}$ and $R^{19}$ are independently selected from the group consisting of H and $C_1$–$C_6$ alkyl; and $R^{20}$ is $C_1$–$C_6$ alkyl or phenyl; or (2) $R^a$ is $R^8$-phenyl, $R^8$-pyridyl or $R^8$-thiophenyl; $R^2$ is fluorenyl, diphenylmethyl,

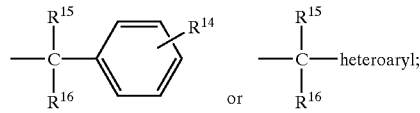

and $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are as defined in (1).

Preferred compounds of formula II are those defined in (1).

More preferred are those of formula II(1) wherein $R^a$ is $R^{8a}$-phenyl or $R^8$-naphthyl, wherein $R^{8a}$ is —$CF_3$, $CF_3O$— or halogen and $R^8$ is $C_1$–$C_6$ alkoxy. The $R^{8a}$ or $R^8$ substituent is preferably a single substituent; it is especially preferred that the $R^{8a}$ or $R^8$ substituent is in the 4-position. Also preferred are compounds of formula II(1) wherein $R^3$ is hydrogen, ($C_1$–$C_6$) alkyl, $R^8$-phenyl. $R^8$-benzyl or $R^8$-pyridyl; more preferred definitions for $R^3$ are methyl, ethyl, phenyl, benzyl and pyridyl. $R^1$ is preferably hydrogen. For compounds of formula II(1), $R^6$ is preferably hydrogen or methyl, especially methyl. $R^4$ is preferably methyl; $R^5$ and $R^7$ are each preferably hydrogen.

$R^2$ in formula II(1) is preferably as defined for formula 1, i.e., $R^9$, $R^{10}$, $R^{11}$-phenyl, $R^9$, $R^{10}$, $R^{11}$-pyridyl or an N-oxide thereof, or $R^9$, $R^{10}$, $R^{11}$-pyrimidyl, wherein the $R^9$, $R^{10}$, $R^{11}$-substitution is as defined above for preferred compounds of formula I.

Another aspect of the invention is a pharmaceutical composition for treatment of HIV comprising an effective amount of a CCR5 antagonist of formula If in combination with a pharmaceutically acceptable carrier. Another aspect of the invention is a pharmaceutical composition for treatment of solid organ transplant rejection, graft v. host disease, arthritis, rheumatoid arthritis, inflammatory bowel disease, atopic dermatitis, psoriasis, asthma, allergies or multiple sclerosis comprising an effective amount of a CCR5 antagonist of formula II in combination with a pharmaceutically acceptable carrier.

Yet another aspect of this invention is a method of treatment of HIV comprising administering to a human in need of such treatment an effective amount of a CCR5 antagonist compound of formula II. Another aspect of the invention is a method of treatment of solid organ transplant rejection, graft v. host disease, arthritis, rheumatoid arthritis, inflammatory bowel disease, atopic dermatitis, psoriasis, asthma, allergies or multiple sclerosis comprising administering to a human in need of such treatment an effective amount of a CCR5 antagonist compound of formula I or II.

Still another aspect of this invention is the use of a CCR5 antagonist of formula I or II of this invention in combination with one or more antiviral or other agents useful in the treatment of Human Immunodeficiency Virus for the treatment of AIDS. Still another aspect of this invention is the use of a CCR5 antagonist of formula I or II of this invention in combination with one or more other agents useful in the treatment of solid organ transplant rejection, graft v. host disease, inflammatory bowel disease, rheumatoid arthritis or multiple sclerosis. The CCR5 and antiviral or other agents which are components of the combination can be administered in a single dosage form or they can be administered separately; a kit comprising separate dosage forms of the actives is also contemplated.

DETAILED DESCRIPTION OF THE INVENTION

As used herein, the following terms are used as defined below unless otherwise indicated.

Alkyl represents straight and branched carbon chains and contains from one to six carbon atoms.

Alkenyl represents $C_2$–$C_6$ carbon chains having one or two unsaturated bonds, provided that two unsaturated bonds are not adjacent to each other.

Substituted phenyl means that the phenyl group can be substituted at any available position on the phenyl ring.

Acyl means a radical of a carboxylic acid having the formula alkyl-C(O)—, aryl-C(O)—, aralkyl-C(O)—, ($C_3$–$C_7$)cycloalkyl-C(O)—, ($C_3$–$C_7$)cycloalkyl-($C_1$–$C_6$) alkyl-C(O)—, and heteroaryl-C(O)—, wherein alkyl and heteroaryl are as defined herein; aryl is $R^{14}$-phenyl or $R^{14}$-naphthyl; and aralkyl is aryl-($C_1$–$C_6$)alkyl, wherein aryl is as defined above.

Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. For 6-membered heteroaryl rings, carbon atoms can be substituted by $R^9$, $R^{10}$ or $R^{11}$ groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings, carbon atoms can be substituted by $R^{12}$ or $R^{13}$ groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3-position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

Preferred points of substitution for 6-membered heteroaryl rings at $R^2$ are described above. When $R^2$ is a 5-membered heteroaryl group, the $R^{12}$ and $R^{13}$ substituents are preferably attached to carbon ring members adjacent to the carbon joining the ring to the rest of the molecule, and $R^{12}$ is preferably alkyl; however, if a heteroatom is adjacent to the carbon joining the ring to the rest of the molecule (i.e., as in 2-pyrrolyl), $R^{12}$ is preferably attached to a carbon ring member adjacent to the carbon joining the ring to the rest of the molecule.

Halogen represents fluoro, chloro, bromo and iodo.

One or more, preferably one to four, antiviral agents useful in anti-HIV-1 therapy may be used in combination with a CCR5 antagonist of the present invention. The antiviral agent or agents may be combined with the CCR5 antagonist in a single dosage form, or the CCR5 antagonist and the antiviral agent or agents may be administered simultaneously or sequentially as separate dosage forms. The antiviral agents contemplated for use in combination with the compounds of the present invention comprise nucleoside and nucleotide reverse transcriptase inhibitors, non-nucleoside reverse transcriptase inhibitors, protease inhibitors and other antiviral drugs listed below not falling within these classifications. In particular, the combinations known as HAART (Highly Active Antiretroviral Therapy) are contemplated for use in combination with the CCR5 antagonists of this invention.

The term "nucleoside and nucleotide reverse transcriptase inhibitors" ("NRTI" s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Wellcome Inc., Research Triangle, NC 27709; didanosine (ddI) available under the VIDEX tradename from Bristol-Myers Squibb Co., Princeton, N.J. 08543; zalcitabine (ddC) available under the HIVID tradename from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR tradename from Glaxo-Wellcome Research Triangle, NC 27709; abacavir (1592U89) disclosed in WO96/30025 and available under the ZIAGEN trademark from Glaxo-Wellcome Research Triangle, NC 27709; adefovir dipivoxil [bis(POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(-)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L-2', 3'-dideoxy-5-fluoro-cytidene) licensed by Yale University to Vion Pharmaceuticals, New Haven Conn. 06511; DAPD, the purine nucleoside, (-)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl) adenine, a acid stable purine-based reverse transcriptase inhibitor discovered by the NIH and under development by U.S. Bioscience Inc., West Conshohoken, Pa. 19428.

The term "non-nucleoside reverse transcriptase inhibitors" ("NNRTI's) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO94/03440 and available under the SUSTIVA tradename from DuPont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96 /10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2, 4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN(available from Merck) as well as nonpeptide protease inhibitors e.g., VIRACEPT (available from Agouron).

Typical suitable PIs include saquinavir (Ro 31-8959) available in hard gel capsules under the INVIRASE tradename and as soft gel capsules under the FORTOUASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK-639) available under the CRIXIVAN tradename from Merck & Co., Inc., West Point, Pa. 19486-0004; nelfnavir (AG-1343) available under the VIRACEPT tradename from Agouron Pharmaceuticals, Inc., LaJolla Calif. 92037-1020; amprenavir (141W94), tradename AGENERASE, a non-peptide protease inhibitor under development by Vertex Pharmaceuticals, Inc., Cambridge, Mass. 02139-4211 and available from Glaxo-Wellcome, Research Triangle, NC under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells, was discovered at the NCl is under development by Bristol-Myers Squibb; in preclinical studies, it was shown to have a synergistic effect on the activity of didanosine and has been studied with stavudine. IL-2 is disclosed in Ajinomoto EP-0142268 , Takeda EP-0176299, and Chiron U.S. Pat. Nos. RE 33653, 4530787, 4569790, 4604377, 4748234, 4752585, and 4949314 is available under the PROLEUKIN (aldesleukin) tradename from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3–100 mg /day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from, NNRTIs and PIs. Typical suitable HAART—multidrug combination therapies include:

(a) triple combination therapies such as two NRTIs and one PI; or (b) two NRTIs and one NNRTI ; and (c) quadruple combination therapies such as two NRTIs , one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The $CD4^+$ and HIV-1-RNA plasma levels should be monitored every 3–6 months. Should viral load plateau, a fourth drug, e.g., one PI or one NNRTI could be added. See the table below wherein typical therapies are further described:

ANTI-HIV-1 MULTI DRUG COMBINATION THERAPIES

A. Triple Combination Therapies

1. Two NRTIs[1]+one PI[2]
2. Two NRTIs[1]+one NNRTI[3]

B. Quadruple Combination Therapies[4]
 Two NRTIs+one PI+a second PI or one NNRTI
C. Alternatives:[5]
 Two NRTI[1]
 One NRTI[5]+one PI[2]
 Two PIs[6]±one NRTI[7] or NNRTI[3]
 One PI[2]+one NRTI[7]+one NNRTI[3]
 Footnotes to Table 1. One of the following: zidovudine+lamivudine; zidovudine+didanosine; stavudine+lamivudine; stavudine+didanosine; zidovudine+zalcitabine 2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p 193–197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Agents known in the treatment of rheumatoid arthritis, transplant and graft v. host disease, inflammatory bowel disease and multiple sclerosis which can be administered in combination with the CCR5 antagonists of the present invention are as follows:

solid organ transplant rejection and graft v. host disease: immune suppressants such as cyclosporine and Interleukin-10 (IL-10), tacrolimus, antilymphocyte globulin, OKT-3 antibody, and steroids;

inflammatory bowel disease: IL-10 (see US 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Certain compounds of the invention may exist in different isomeric forms (e.g., enantiomers, diastereoisomers, atropisomers and rotamers). The invention contemplates all such isomers both in pure form and in admixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention can be made by the procedures known in the art, for example by the procedures described in the following reaction schemes, by the methods described in the examples below, and by using the methods described in WO96/26196 and WO98/05292.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); 1-hydroxy-benzotriazole (HOBT); m-chloroperbenzoic acid (MCPBA); triethylamine ($Et_3N$); diethyl ether ($Et_2O$); dimethylsulfoxide (DMSO); and 1-(3-dimethylaminopropyl)-3-ethyl carbodiimide hydrochloride (DEC). RT is room temperature, and TLC is thin-layer chromatography. Me is methyl, Et is ethyl, Pr is propyl, Bu is butyl, Ph is phenyl, and Ac is acetyl.

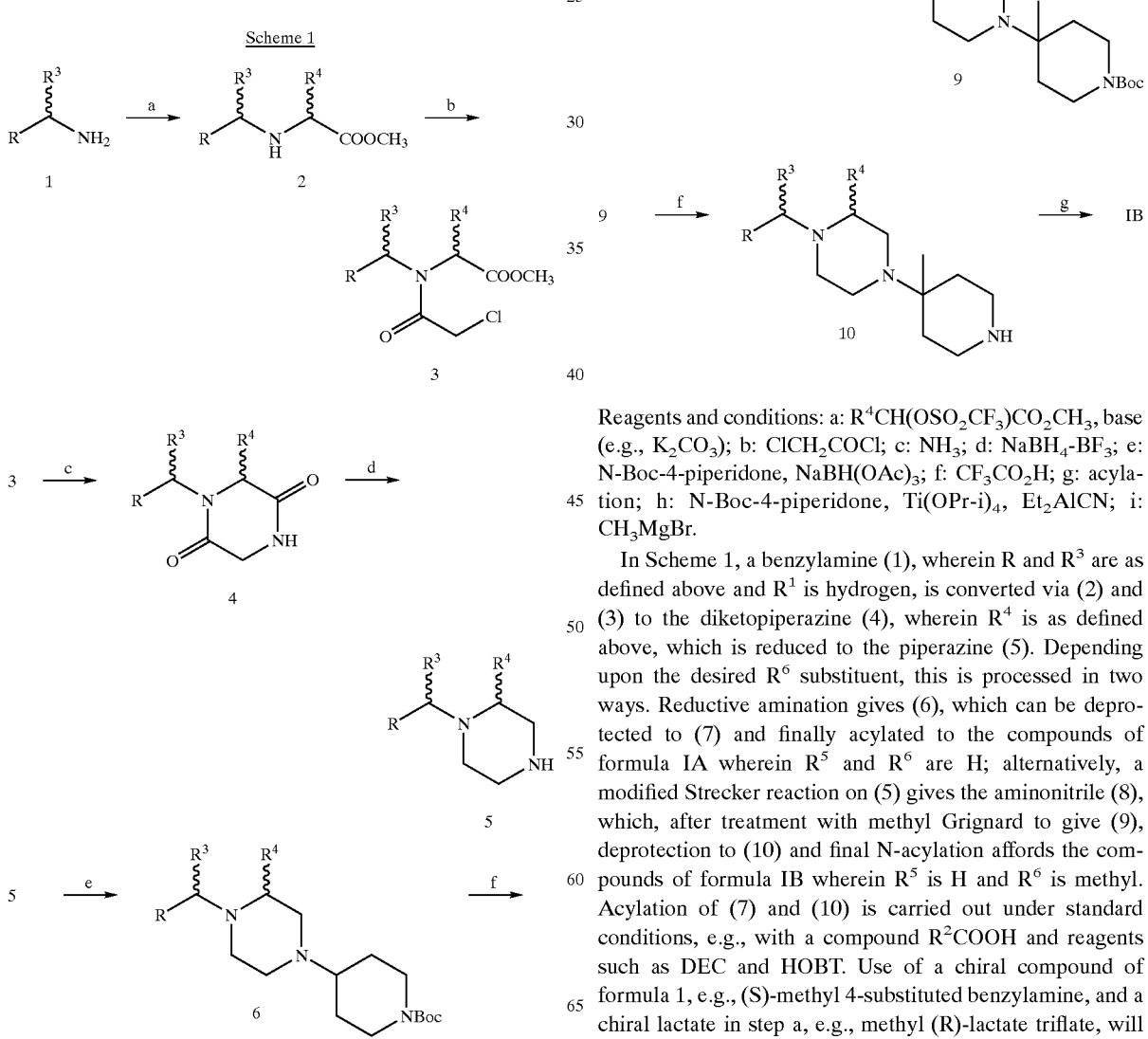

Reagents and conditions: a: $R^4CH(OSO_2CF_3)CO_2CH_3$, base (e.g., $K_2CO_3$); b: $ClCH_2COCl$; c: $NH_3$; d: $NaBH_4$-$BF_3$; e: N-Boc-4-piperidone, $NaBH(OAc)_3$; f: $CF_3CO_2H$; g: acylation; h: N-Boc-4-piperidone, $Ti(OPr-i)_4$, $Et_2AlCN$; i: $CH_3MgBr$.

In Scheme 1, a benzylamine (1), wherein R and $R^3$ are as defined above and $R^1$ is hydrogen, is converted via (2) and (3) to the diketopiperazine (4), wherein $R^4$ is as defined above, which is reduced to the piperazine (5). Depending upon the desired $R^6$ substituent, this is processed in two ways. Reductive amination gives (6), which can be deprotected to (7) and finally acylated to the compounds of formula IA wherein $R^5$ and $R^6$ are H; alternatively, a modified Strecker reaction on (5) gives the aminonitrile (8), which, after treatment with methyl Grignard to give (9), deprotection to (10) and final N-acylation affords the compounds of formula IB wherein $R^5$ is H and $R^6$ is methyl. Acylation of (7) and (10) is carried out under standard conditions, e.g., with a compound $R^2COOH$ and reagents such as DEC and HOBT. Use of a chiral compound of formula 1, e.g., (S)-methyl 4-substituted benzylamine, and a chiral lactate in step a, e.g., methyl (R)-lactate triflate, will result in chiral compounds of formulas IA and IB.

Scheme 2

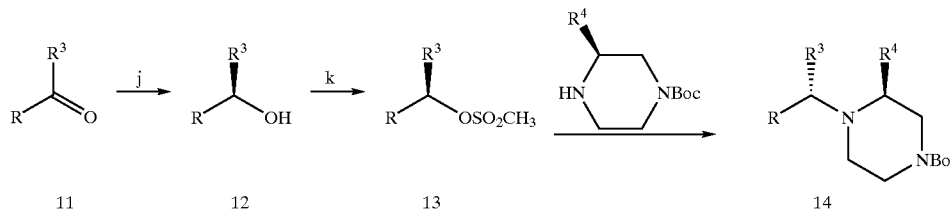

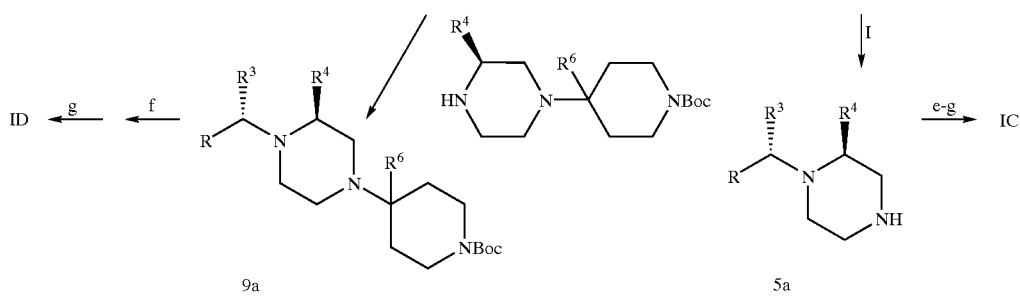

Reagents: j: oxaborazolidine, BH₃; k: CH₃SO₂Cl, base; l: CF₃CO₂H.

In Scheme 2, the compounds are prepared by an alkylation process on a pre-formed piperazine derivative. For example, preferred compounds with the S,S stereochemistry may be obtained in this way by chiral reduction of a ketone (11) to the alcohol (12), activation as the mesylate, and displacement with inversion by treatment with a suitable piperazine, which may either be mono-protected, in which case final elaboration requires deprotection followed by the steps described in (e)–(g) in Scheme 1 to obtain IC, or may be elaborated prior to the displacement step, in which case the final steps are (1) and (g) (deprotection and acylation) as in Scheme 1 to obtain ID.

Scheme 3

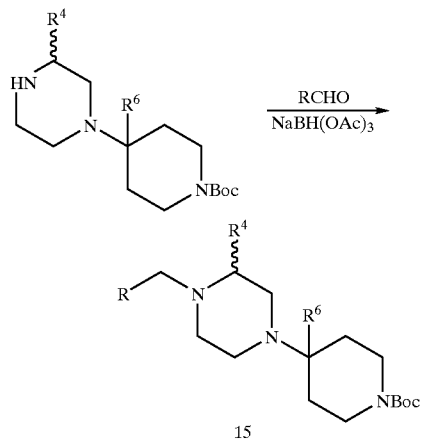

For compounds where $R^3$ and $R^1$ are each H, either the alkylation route of Scheme 2 or a reductive amination method as typified in Scheme 3 can be used.

Scheme 4

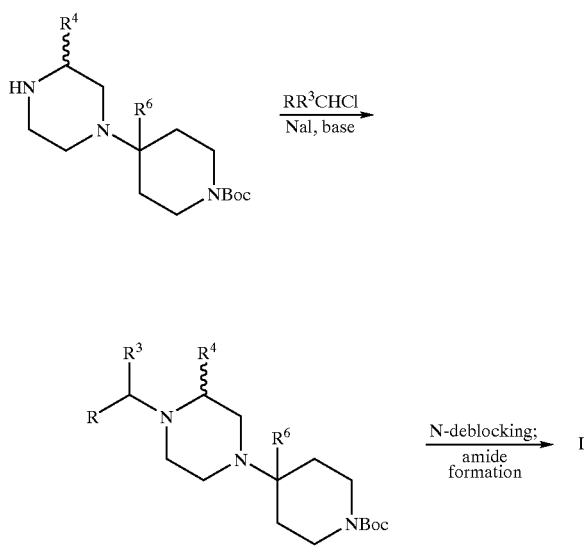

For diaryl compounds, wherein R and $R^3$ are each aryl, an alkylation method as typified in Scheme 4 is preferrred.

Scheme 5

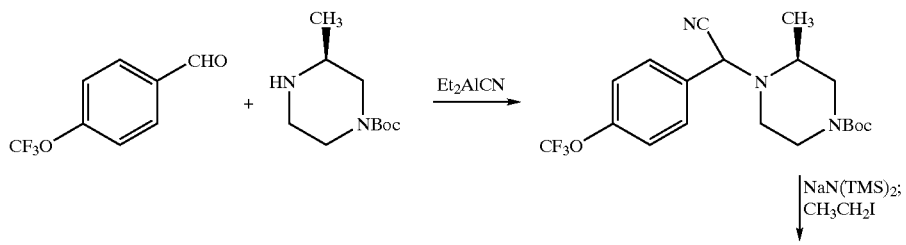

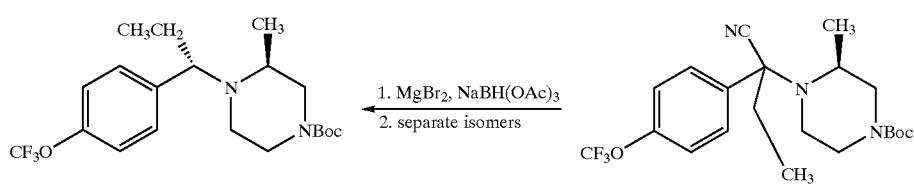

Piperazines of formula 14, especially those wherein $R^3$ is $C_2$–$C_6$ alkyl or benzyl, may also be obtained by a process wherein the

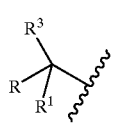

portion is introduced as shown above by an alkylation-decyanation sequence. The reaction is exemplified for compounds wherein R is $CF_3O$-phenyl, $R^1$ is hydrogen, $R^3$ is ethyl and $R^4$ is methyl, but using appropriate starting materials, other compounds of formula 14 can be similarly prepared.

Scheme 6

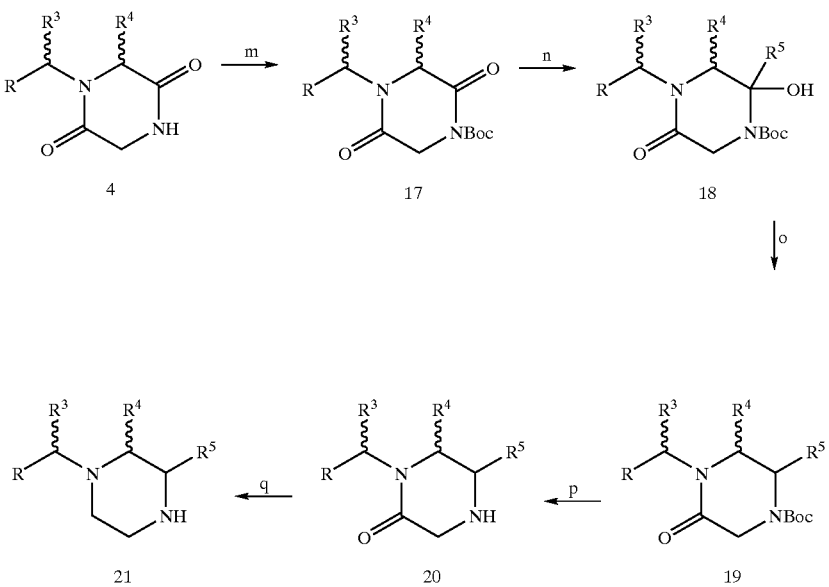

Reagents: m: $BOC_2O$, base; n: $R^6MgBr$; o: $CCl_3CO_2H$, $NaBH_3CN$; p: $CF_3CO_2H$; q: $NaBH_4$, $BF_3$.

As shown in Scheme 6, compounds bearing an additional alkyl group at $R^5$ on the piperazine ring may be prepared from the diketopiperazine intermediates (4) of Scheme 1. (4) is activated by conversion to the N(t-butoxycarbonyl) compound (17); addition of a Grignard reagent and sequential reduction, deprotection and lactam reduction provides (21), which can be used to prepare compounds of formula I in the manner described for intermediate (5) in Scheme 1.

Scheme 7

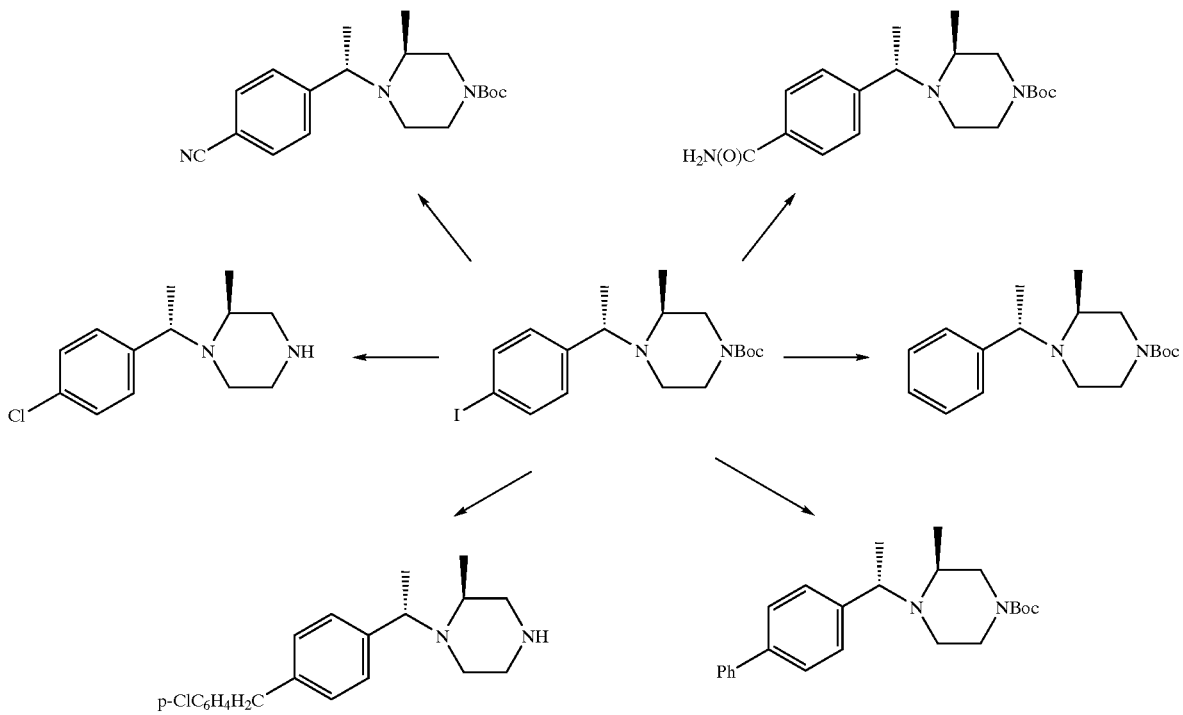

Many piperazines wherein R is R[8]-phenyl (or their Boc derivatives) shown in Scheme 1 can be obtained from a common intermediate, wherein R[8] is I. Several examples are shown in the above scheme, wherein R[8] is converted to Cl, CN, —C(O)NH$_2$, H, Ph and p-ClC$_6$H$_4$CH$_2$-. Detailed procedures for these conversions are provided in the examples below. The resultant piperazine or BOC-piperazine is then treated as shown in Scheme 1.

Some compounds of the invention may be obtained by a Mannich method, as shown in the specific example of Scheme 8.

Compounds useful in this invention are exemplified by the following preparative examples, which should not be construed to limit the scope of the disclosure. Alternative mechanistic pathways and analogous structures within the scope of the invention may be apparent to those skilled in the art.

Scheme 8

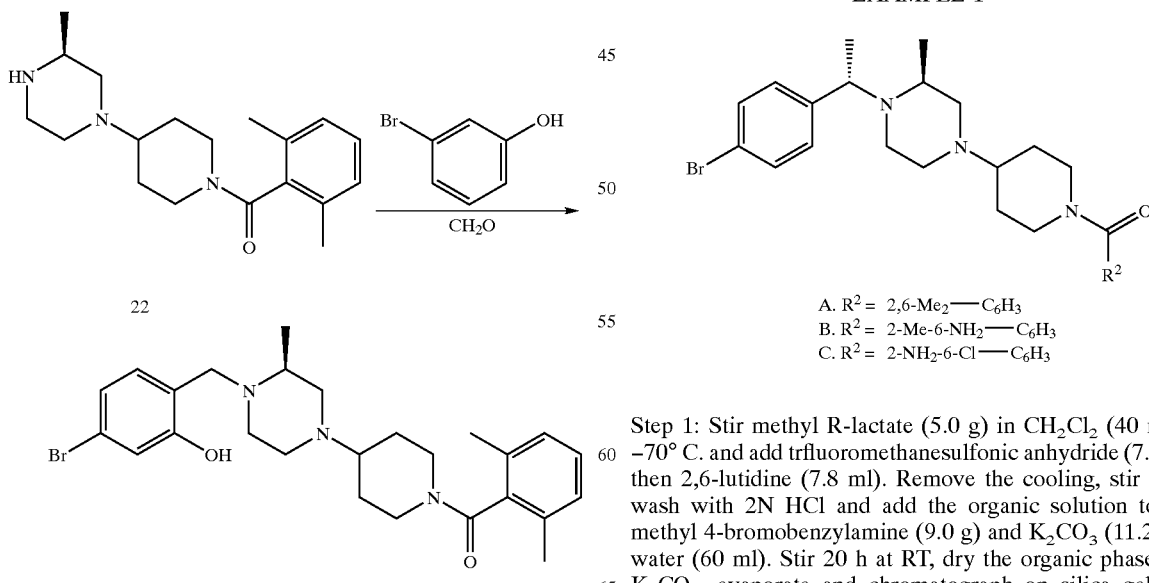

EXAMPLE 1

A. R$^2$ = 2,6-Me$_2$—C$_6$H$_3$
B. R$^2$ = 2-Me-6-NH$_2$—C$_6$H$_3$
C. R$^2$ = 2-NH$_2$-6-Cl—C$_6$H$_3$

Step 1: Stir methyl R-lactate (5.0 g) in CH$_2$Cl$_2$ (40 ml) at −70° C. and add trfluoromethanesulfonic anhydride (7.6 ml), then 2,6-lutidine (7.8 ml). Remove the cooling, stir 0.5 h, wash with 2N HCl and add the organic solution to (S)-methyl 4-bromobenzylamine (9.0 g) and K$_2$CO$_3$ (11.2 g) in water (60 ml). Stir 20 h at RT, dry the organic phase over K$_2$CO$_3$. evaporate and chromatograph on silica gel with Et$_2$O—CH$_2$Cl$_2$ to give the desired product (7.50 g) as a thick oil.

Step 2: Reflux the product of step 1 (7.5 g) in 1,2-dichloroethane (40 ml) and ClCH$_2$COCl (5.0 ml) for 5 h, then evaporate and use the resultant residue directly in the next step.

Step 3: Stir the product of step 2 in DMSO (80 ml), water (10 ml) and NaI (8 g), cool in ice, add conc. NH$_4$OH solution (15 ml) and stir to RT for 20 h. Add water (200 ml) dropwise, collect the solid, wash well with water and dry at 70° C./5 mm to give the diketopiperazine, suitable for the next step.

Step 4: Stir a mixture of the product of step 3 (6.8 g), 1,2-dimethoxyethane (60 ml) and NaBH$_4$ (3.4 g) under N$_2$, add BF$_3$.OEt$_2$ (6.8 ml) dropwise, then heat at 100° C. for 10 h. Cool and add CH$_3$OH (20 ml) dropwise, followed by conc. HCl (30 ml). Heat at 100° C. for 1 h., cool, basify with excess 2N NaOH and extract with EtOAc. Dry over K$_2$CO$_3$ and evaporate to obtain the piperazine (5.85 g), suitable for the next step.

Step 5: Stir for 20 h. at RT a mixture of the product of step 4 (5.48 g), N-Boc-4-piperidinone (4.32 g), HOAc (1.15 ml), CH$_2$Cl$_2$ (80 ml) and sodium triacetoxy-borohydride (NaBH(OAc)$_3$) (8.3 g). Add excess aqueous Na$_2$CO$_3$ solution slowly, stir for 0.5 h, separate and filter the organic phase through a pad of silca gel, washing with 10:1 CH$_2$Cl$_2$-Et$_2$O to elute all of the product. Evaporate and dissolve the residue in Et$_2$O (100 ml). Stir and add a 4M solution of HCl in 1,4-dioxane (10 ml) dropwise. Collect the solid, wash with Et$_2$O, and stir with CH$_2$Cl$_2$ and excess aqueous NaOH. Dry the organic phase over K$_2$CO$_3$ and evaporate to obtain the desired product (5.45 g).

Step 6: Stir at RT for 2 h a mixture of the product of step 5 (1.5 g) and TFA (4 ml). Evaporate, dissolve in CH$_2$Cl$_2$ and wash with excess 1N NaOH solution. Dry over K$_2$CO$_3$ and evaporate to obtain the product (1.15 g).

Compound 1A:

Following the standard procedure, react the product of step 6 with 2,6-dimethylbenzoyl chloride in CH$_2$Cl$_2$ and aqueous NaOH, and convert the product to the hydrochloride. Mp 185–192° C. (decomposition). HRMS found: 498.2130; MH$^+$ Calc: 498.2120.

Compound 1B:

Following the standard procedure, couple the product of step 6 with 2-amino-6-methylbenzoic acid using HOBT and DEC with diisopropylethylamine in DMF, purify the amide by preparative TLC and convert to the hydrochloride. Mp 188–196° C. (decomposition). HRMS found: 499.2069; MH$^+$ Calc: 499.2072.

Compound 1C:

Following the above method, couple the product of step 6 with 2-amino-6-chlorobenzoic acid and convert after purification to the hydrochloride. Mp 192–200° C. (decomposition). HRMS found: 519.1530; MH$^+$ Calc: 519.1526.

EXAMPLE 2

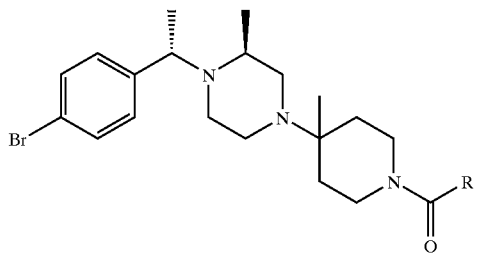

A. $R^2$ = 2,6-Me$_2$C$_6$H$_3$
B. $R^2$ = 2-NH$_2$-6-Cl—C$_6$H$_3$
C. $R^2$ = 2-Me-6-OH—C$_6$H$_3$
D. $R^2$ = 2-Me-6-NH$_2$C$_6$H$_3$

Step 1: Stir the product of Example 1, step 4 (1.00 g), N-t-butoxycarbonyl-4-piperidinone (0.77 g) and titanium (IV) isopropoxide (Ti(OiPr)$_4$) (1.00 g) for 20 h at RT in CH$_2$Cl$_2$ (15 ml), reflux for 3 h and cool to RT. Add diethylaluminum cyanide (Et$_2$AlCN) (4.2 ml of 1M toluene solution) and the stir for 5 days at RT under dry N$_2$. Workup in CH$_2$Cl$_2$-aq. NaOH, dry and evaporate the organic phase and chromatograph on silica gel with CH$_2$Cl$_2$—CH$_3$OH (100:1) to obtain the desired product (0.72 g).

Step 2: React the product of step 1 (0.70 g) in dry THF (15 ml) under N$_2$ with CH$_3$MgBr (4 ml of 3M Et$_2$O solution) at RT for 20 h. Workup in EtOAc-water and filter the organic phase through silica gel, washing with EtOAc. Evaporate to obtain the desired product (0.65 g).

Step 3: Deprotect the product of step 2 with TFA according to the procedure described in Example 1, step 6.

Compound 2A:

React the product of step 3 with dimethylbenzoyl chloride as described in Example 1 and convert to the HCl salt. Mp 180–187° C. (decomposition). HRMS Found: 512.2272; MH$^+$ Calc: 512.2276.

Compound 2B:

React the product of step 3 with 2-amino-6-chlorobenzoic acid as described in Example 1, purify the crude product by preparative TLC and convert to the HCl salt. Mp 195–200° C. (decomposition). HRMS Found: 535.1662; MH$^+$ Calc: 535.1652.

Compound 2C:

React the product of step 3 with 2-hydroxy-6-methylbenzoic acid as described in Example 1, purify the crude product by preparative TLC and convert to the HCl salt. Mp 206–210° C. (decomposition). HRMS Found: 514.2067; MH$^+$ Calc: 514.2069.

Compound 2D:

React the product of step 3 with 2-amino-6-methylbenzoic acid using a procedure similar to that described in Example 1, purify the crude product by preparative TLC and convert to the HCl salt. Mp 202-209° C. (decomposition). HRMS Found: 513.2227; MH$^+$ Calc: 513.2229.

EXAMPLE 3

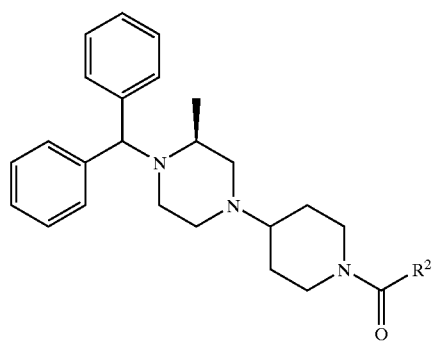

A. $R^2$ = 2,6-di-Me—C$_6$H$_3$
B. $R^2$ = 2-NH$_2$-6-Cl—C$_6$H$_3$
C. $R^2$ = 2,4-di-Me-3-pyridyl Step 1: Reflux and stir a mixture of S-alanine methyl ester hydrochloride (14 g), anhydrous Na$_2$CO$_3$ (60 g), dry CH$_3$CN (125 ml), chlorodiphenylmethane (22.3 g) and NaI (5 g) for 6 hr. Cool, add ice-H$_2$O and extract with Et$_2$O (350 ml, then 50 ml). Combine the Et$_2$O extracts and wash with portions of 1N aq. HCl: 200 ml, 100 ml, then 4×10 ml. Combine the aqueous acid extracts, stir and add excess Na$_2$CO3 in small poprtions until the mixture is basic. Extract with Et$_2$O, dry over MgSO$_4$ and evaporate to obtain the N-diphenylmethyl compound (23.2 g).

Step 2: Reflux all of the above compound with ClCH₂COCl (10 ml) in dichloroethane (60 ml) for 4 h. Evaporate, and co-evaporate with toluene (20 ml). Dissolve the residue in CH₂Cl₂ (200 ml), stir for 0.5 h with activated carbon (10 g), filter and evaporate. Stir the residue with ice cooling in DMSO (200 ml) and gradually add concentrated aqueous NH₃ (100 ml), then NaI (10 g). Stir at RT for 20 hr. Add iced water (500 ml), collect the solid, wash well with water, then with several small portions of a 10:1 hexane-Et₂O mixture, and dry at 50° C. with high vacuum to obtain the solid diketopiperazine (15.5 g). Recrystallise a small sample from CH₂Cl₂-hexanes: mp 186–188° C.; $[\alpha]_D^{20}$=+272.6°.

Step 3: Stir the product of step 2 (4.0 g) in dimethoxyethane (40 ml) and NaBH₄ (1.6 g) under N₂ and add BF₃.OEt₂ (3.2 ml) slowly. Reflux for 20 h. Cool and add CH₃OH (10 ml) dropwise, then conc. HCl (15 ml). Reflux for 2 h., and work up in excess 2N aq. NaOH and extract with CH₂Cl₂. Dry over K₂CO₃ and evaporate. Chromatograph on silica, eluting with CH₂Cl₂—CH₃OH mixtures, and finally with 5:1:0.1 v/v/v CH₂Cl₂:CH₃OH:NH₄OH. Combine and evaporate the product fractions to obtain the desired product (1.95 g) as a pale yellow gum.

Step 4: Stir a mixture of the product of step 3 (0.50 g), N-allyloxycarbonyl-4-piperidone (0.40 g), CH₂Cl₂ (5 ml) and NaBH(OAc)₃ (0. 70 g) at RT for 20 h. Work up in CH₂Cl₂ and excess aq. NaOH, dry over MgSO₄, evaporate and isolate the product by preparative TLC, eluting with 10% Et₂O in CH₂Cl₂, to obtain the desired compound (0.80 g) as an oil, contaminated with a small amount of starting ketone, but suitable for the next step.

Step 5: Stir a mixture of the product of step 4 (0.80 g), CH₃CN (20 ml), water (5 ml) and piperidine (1.5 ml). Add tri(4-sulfophenyl)phosphine (0.072 g) and palladium (II) acetate (0.02 g) and stir at RT under N₂ for 2 h. Work up with aqueous NaOH, extract with 5:1 v/v toluene:CH₂Cl₂, dry over K₂CO₃ and evaporate to obtain a yellow oil, suitable for acylation.

Compound 3A:

Stir and reflux a mixture of the product of step 5 (0.10 g), N-(2,6-dimethoxybenzoyl)-4-piperidinone (0.10 g), CH₂Cl₂ (2 ml) and NaBH(OAc)₃ (0.15 g) for 2.5 h., cool, and work up with CH₂Cl₂ and aqueous NaOH. Dry over MgSO₄, evaporate and isolate the major product by preparative TLC, eluting with 3:1 v/v Et₂O:CH₂Cl₂. Precipitate the hydrochoride to obtain the desired compound as the HCl salt (0.13 g). Mp 173–177° C. (decomposition). HRMS Found: 482.3175; MH⁺ Calc: 482.3171.

Compound 3B:

Couple the product of step 5 with 2-amino-6-chlorobenzoic acid using DEC-HOBT as described in Example 1, isolate the product by PTLC and precipitate the hydrochloride to give compound 3B. Mp 188–195° C. (decomposition). HRMS Found: 503.2567; MH⁺ Calc: 503.2578.

Compound 3C:

Couple the product of step 5 with 2,4-dimethyinicotinic acid using DEC-HOBt as described above, isolate the product by PTLC and precipitate the hydrochloride to give compound 3C. Mp 180–188° C. (decomposition). HRMS Found: 483.3114; MH⁺ Calc: 483.3124.

Using procedures similar to those described above, the following compounds were prepared:

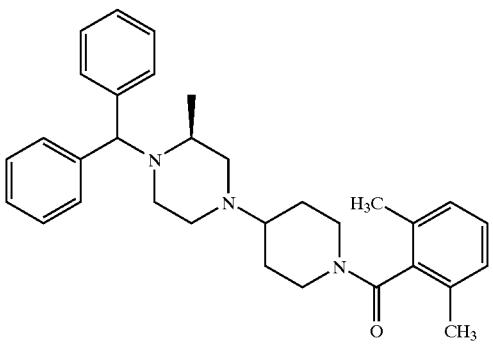

3D: Mp. 85–89° C.; HRMS (MH⁺) found: 496.3343

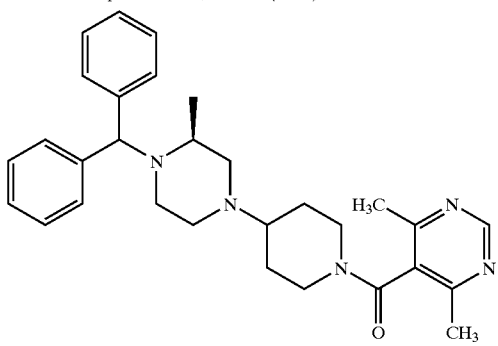

3E; Mp. 170–175° C.

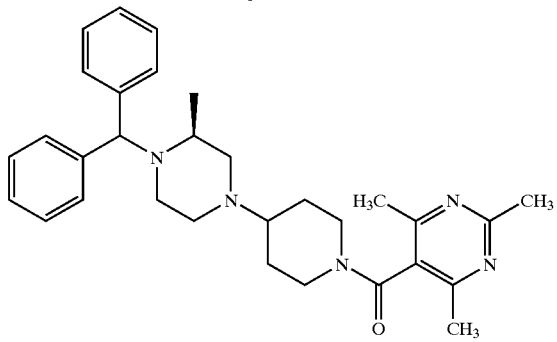

3F; Mp. 180–185° C.

EXAMPLE 4

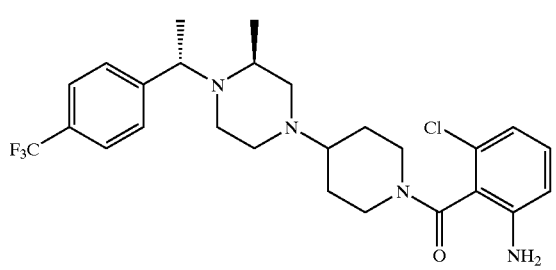

Step 1: A solution of 4-trifluoromethyl acetophenone (1.88 g; 10 mmol) in dry THF (10 ml) was cooled in an ice bath and treated with freshly prepared solid (S)-2-methyl oxaborolidine (0.54 g; 2 mmol). After 10 min., a solution of 2M borane-methyl sulfide complex (3 ml; 6 mmol) in THF was added dropwise over 5 min. TLC at the end of 30 min. showed that the starting material had been converted to a more polar product. The reaction was quenched with about 5 ml of CH₃OH carefully until effervescence stopped; volatiles were removed in vacuo. The residue was dissolved in CH₂Cl₂ and washed with 1N HCl, water, 10% NaHCO₃ solution and brine. Concentration in vacuo gave 2 g of a yellow gum. Flash silica gel chromatography (FSGC) using 10–20% EtOAc in hexanes furnished the desired chiral alcohol (1.6 g; 84%) as a colorless oil. TLC R$_f$=0.6 in 25% EtOAc:hexanes.

Step 2: To a solution of the product of step 1(1.55 g; 8.16 mmol) in 10 ml of CH₂Cl₂ cooled in an ice bath were added Et₃N (2.3 ml; 16.32 mmol) and CH₃SO₂Cl (0.87 ml; 10.6 mmol) to form a turbid white solution. The reaction was quenched with water and the organic product was extracted with CH₂Cl₂, washing with water, 1N HCl, 10% NaHCO₃ solution and brine. Concentration in vacuo gave the chiral mesylate (2.1 g; 96%) as a pale yellow oil. TLC R$_f$=0.6 in 25% EtOAc:hexanes.

Step 3: A solution of the product of step 2 (2.1 g; 7.8 mmol), the N-BOC protected 2(S)-methyl piperazine (1.56 g; 7.8 mmol-prepared from the reaction of commercial 2(S)-methyl piperazine with N-(tert-butoxy-carbonyloxy) phthalimide) and 2,2,6,6-tetramethyl piperidine (1.34 ml; 8 mmol) in 14 ml of dry CN₃CN were heated at reflux until TLC indicated complete disappearance of the mesylate (16 h). The reaction mixture was cooled to RT, diluted with CH₂Cl₂ (50 ml) and washed with water (3×100 ml) and brine. The organic extract was dried over solid MgSO₄ and then concentrated to obtain 2.8 g of a yellow gum. FSGC (20% EtOAc in hexanes) served to isolate the desired (S,S)-diastereomer (1.5 g; 52%) and its benzylic epimer, the (R,S)-diastereomer (0.5 g; 17%) for a combined 69% yield. TLC R$_f$=0.75 (S,S) and 0.56 (R,S) in 25% EtOAc:hexanes.

Step 4: TFA (6 ml) was added to a solution of the product of step 3 in 12 ml of CH₂Cl₂ and the resulting yellow-orange solution was stirred at RT for 8 h. The reaction was quenched by adding 1N NaOH solution to adjust the pH to 10. Extractive work up in CH₂Cl₂ gave 1.1 g of a yellow syrup. FSGC using 10% CH₃OH in CH₂Cl₂ removed the less polar impurity and gradient elution with 1% Et₃N in 10% CH₃OH:CH₂Cl₂ was needed to elute the desired free amine of the (S,S) diastereomer. Yield=0.9 g (75%). TLC R$_f$=0.5 in 10% CH₃OH:CH₂Cl₂.

Step 5: A colorless solution of the product of step 4 (0.9 g; 3.3 mmol), 4-piperidinone (0.86 g; 4.3 mmol), NaB(OAc)₃H (1.05 g; 4.95 mmol) and glacial AcOH (80 µl) in 8 ml of CH₂Cl₂ was stirred at ambient temperature for a day. TLC indicated absence of starting material. The reaction mixture was diluted with 50 ml of CH₂Cl₂, washed with 1N NaOH solution, water (2×) and brine. The CH₂Cl₂ extract was dried over anhydrous MgSO₄ and concentrated to obtain 1.7 g of yellow oil. FSGC (25% acetone in hexanes) was used to isolate the pure product (1.3 g; 86%) as a white foam. TLC R$_f$=0.6 in 25% acetone/hexanes.

Step 6: TFA (5 ml) was added to a solution of the product of step 5 (1.3 g; 2.87 mmol) in CH₂Cl₂ (10 ml) and the resulting yellow orange solution was stirrred at RT for 7 h. The reaction was quenched with 1N NaOH solution and the pH was adjusted to 10. The organic product was extracted into 50 ml of CH₂Cl₂ and washed with water, then brine and dried over MgSO₄. Concentration gave the free amine (0.98 g; 98%) as a yellow syrup. TLC R$_f$=0.1 in 25% acetone/hexanes.

Step 7: The product of step 6 (0.78 g; 2.21 mmol), DEC (0.65 g; 3.4 mmol), HOBT (0.46 g; 3.4 mmol) and 2-amino-6-chloro benzoic acid (0.51 g; 2.9 mmol) were dissolved in 8 ml of CH₂Cl₂ to which was added diisopropylethyl amine (0.7 ml) and the mixture was stirred at ambient temperature for 16 h. TLC analysis showed absence of starting material and formation of two over-lapping spots of medium polarity (rotomers of the hindered amide) as the major product. The crude product (1.3 g) was isolated by extractive work up and purified through FSGC using 25% acetone in CH₂Cl₂ as eluant to give the title compound (0.88 g; 80%) as a pale yellow foam. TLC R$_f$=0.45 and 0.5 in 25% acetone:CH₂Cl₂.

A solution of hydrogen chloride in Et₂O (1M; 3 ml) was added to a solution of the title compound free base (0.76 g; 1.54 mmol) in CH₂Cl₂ (5 ml) to obtain an instantaneous white precipitate. After stirring at RT for 2 h, the volatiles were removed on a rotary evaporator and the white residue was suspended in dry toluene (3×10 ml) and azeotroped. The white solid thus obtained was suspended in dry Et₂O containing 10% EtOAc, stirred for 30 min, filtered and washed with Et₂O (100 ml). The HCl salt of the title compound was dried under high vacuum to yield an off-white solid (0.88 g; 95%). Mp: 205–210° C.

The product of step 6 was converted to other amides (4A–4E) as described in step 7 using the appropriate carboxylic acids. Physical data for compounds 4–4E having the following structures is as follows:

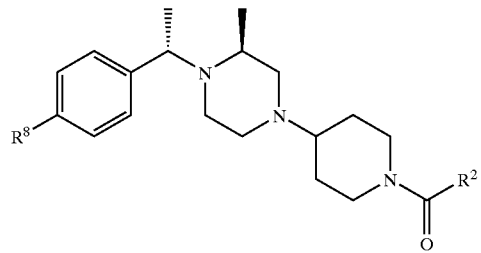

wherein R⁸ and R² are defined in the table:

| Ex. | R⁸ | R² | Mp (° C.) | HRMS (MH⁺) |
|---|---|---|---|---|
| 4 | CF₃ | Cl, NH₂ (substituted phenyl) | 205–210 | 509.2295 |
| 4A | CF₃ | NH₂ (substituted phenyl) | 192–195 | 489.2841 |
| 4B | CF₃ | OH (substituted phenyl) | 203–206 | 490.2681 |
| 4C | CF₃ | (substituted phenyl) | 186–190 | 488.2902 |

-continued

| Ex. | R⁸ | R² | Mp (° C.) | HRMS (MH⁺) |
|---|---|---|---|---|
| 4D | CF₃ | 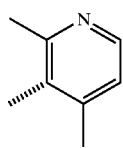 | 207–210 | 489.2851 |
| 4E | CF₃ | 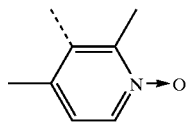 | 152 | 505 |
| 4F | CF₃ | 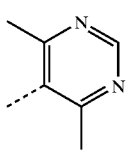 | — | 490.2796 |

EXAMPLE 5

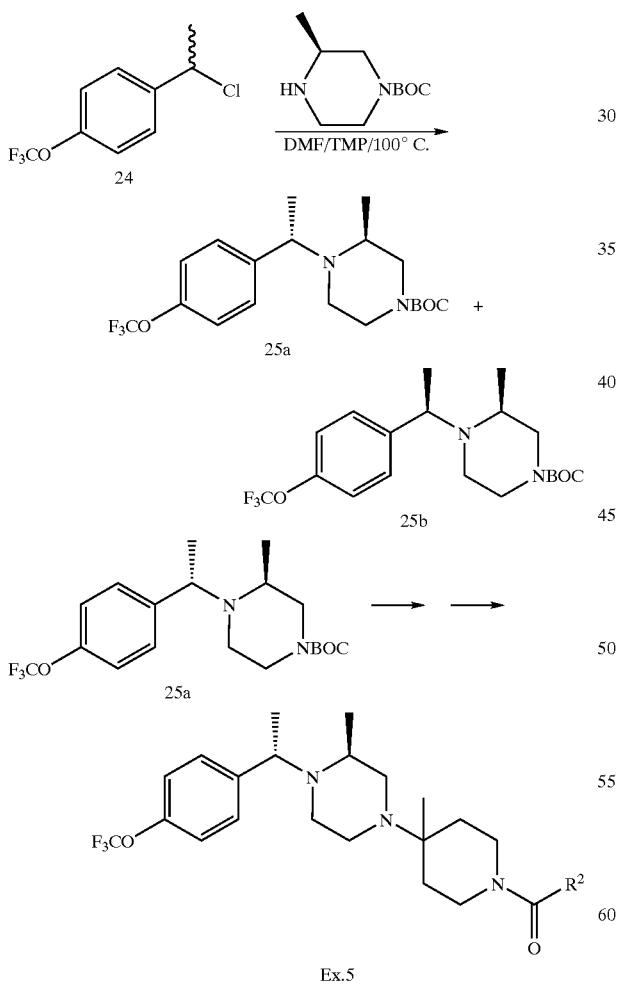

A solution of the racemic benzyl chloride 24 (1.26 g, 5.62 mmol) which was prepared freshly from the corresponding carbinol, the 2(S)-methyl piperazine (1.12 g, 5.62 mmol) and 2,2,6,6-tetramethyl piperidine (TMP) (1.9 ml, 11.2 mmol) were dissolved in dry DMF (2 ml) and heated to 100–110° C. (internal temp.) for 10 h. TLC analysis showed absence of 24 and formation of two well-separated products. The mixture was diluted with water and the organics were extracted into Et₂O. The organic extract was washed with saturated NH₄Cl and brine and concentrated in vacuo to obtain 2 g of crude product. Flash chromatography on silica gel and elution first with 25% Et₂O-hexane followed by 25% EtOAc-hexane gave ~0.5 grams of 25a and ~0.5 grams of 25b respectively (~45% combined yield). TLC R$_f$=0.6 (for 25a) and 0.4 (for 25b) in 25% EtOAc-hexanes. Purified 25a was treated as described previously to obtain the final products 5 to 5F having the formula .

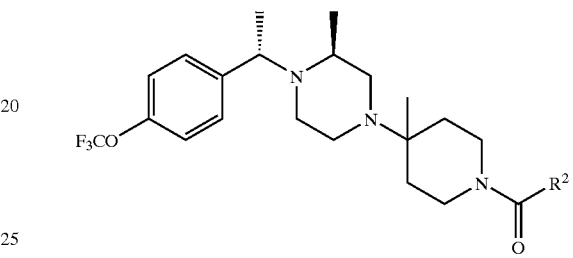

wherein R² is defined in the table:

| Ex. | R² | mp (° C.) | HRMS |
|---|---|---|---|
| 5 | 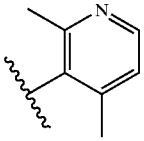 | 208–212 | 519.2958 |
| 5A | 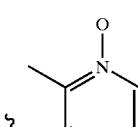 | 198–203 | 535.2913 |
| 5B | 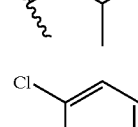 | 233 (sharp) | 539.2390 |
| 5C | 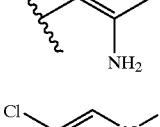 | 190 | 575.1800 |
| 5D | 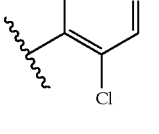 | 253 | 558.1887 |

-continued

| Ex. | R² | mp (° C.) | HRMS |
|---|---|---|---|
| 5E | 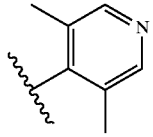 | 202 | 519.2964 |
| 5F | 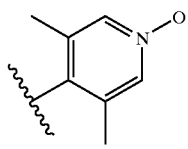 | 190 | 535.2901 |
| 5G | 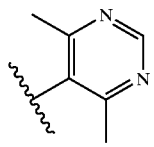 | 198–203 | — |
| 5H | 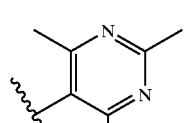 | 205–210 | — |

EXAMPLE 6

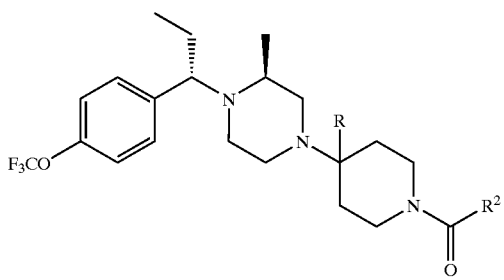

Step 1:

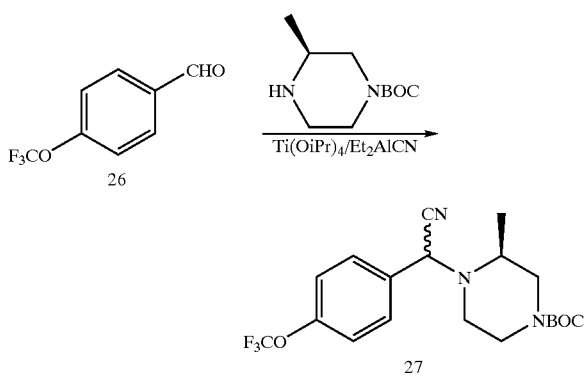

1) NaHMDS/Et-1
2) Na(OAc)₃BH
   MgBr₂:Et₂O/CH₃CN

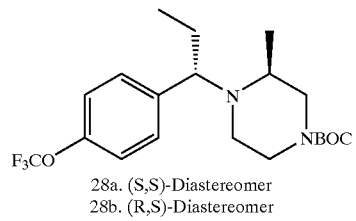

28a. (S,S)-Diastereomer
28b. (R,S)-Diastereomer

Step 1:

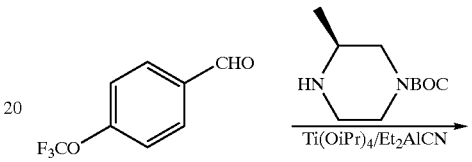

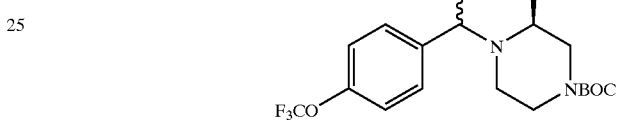

27  1) NaHMDS/Et-I
    2) Na(OAc)₃BH
       MgBr₂:Et₂O/CH₃CN

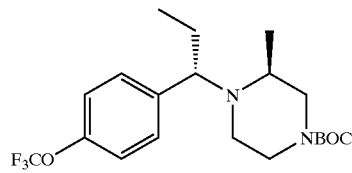

28a. (S,S)-Diastereomer
28b. (R,S)-Diastereomer

A mixture of the aldehyde 26 (3.9 g, 20.5 mmol), the 2(S)-methyl-N-BOC-piperazine (4.1 g, 20.5 mmol) and Ti(OiPr)₄ (6.1 mL; 20.5 mmol) in 40 ml of CH₂Cl₂ was stirred at RT for 24 h. Et₂AlCN was introduced and stirred for an additonal day. The reaction mixture was processed as described before to obtain 4.71 grams (58%) of the cyano amine 27 after FSGC (TLC $R_f$=0.45/0.5 for diastereomers seen with 25% Et₂O-hexanes as solvent).

Step 2: Sodium hexamethyldisilazide (1M; 3.1 ml) was added to a solution of 27 (1 g; 2.5 mmol) in dry THF cooled in a dry ice/acetone bath. The resulting bright yellow solution was treated with CH₃CH₂I (7.5 mmol; 0.6 ml). The dry ice bath was removed and the reaction was stirred at ambient temperature for 15 min. followed by gentle warming in a warm water bath (40° C.) for 30 min. TLC indicated two well-separated spots. Standard extractive work up and purification by FSGC gave two alkylated compounds (combined yield: 0.7 g; 70%). TLC $R_f$=0.6 and 0.4 (25% EtOAc/hexanes).

Step 3: The product of step 2 was stirred with NaBH(OAc)₃ (2x) and MgBr₂:OEt₂ (1x) in CH₃CN for a day. The reaction mixture was quenched with water, the organics were extracted into EtOAc and processed to obtain 0.8 grams of crude product. FSGC (25% EtOAc-hexanes) gave ~0.4 grams of each diastereomer (combined yield ~100%). TLC $R_f$=0.55 (28a) and 0.45 (28b) in 25% EtOAc-hexanes.

Step 4: Compound 28a (S,S-diastereomer) was processed through the usual 5 step sequence to complete the synthesis of compounds of Example 6, 6A and 6B with an ipso-methyl group as well as compounds 6C and 6D which lack the ipso-methyl group:

| Ex. | $R^6$ | $R^2$ | mp (° C.) | MS (MH$^+$) |
|---|---|---|---|---|
| 6 | CH$_3$ | 2,4-dimethylpyridine N-oxide | 204 | 549.5 |
| 6A | CH$_3$ | 3,5-dichloropyridine N-oxide | 253 | 589.4 |
| 6B | CH$_3$ | 4,6-dimethylpyrimidine | 260 | 534.4 |
| 6C | H | 4,6-dimethylpyrimidine | 225 | 520.4 |
| 6D | H | 3,5-dichloropyridine N-oxide | 215 | 575.4 |

EXAMPLE 7

The synthesis of compounds with an alkyl or arylsulfonyl $R^8$ group at the para position started with the corresponding para-substituted acetophenone which was treated as in Example 4, steps 1–6 to obtain the sulfone containing compounds of Example 7 havng the formula:

wherein $R^8$ and $R^2$ are defined in the table:

| Ex. | $R^8$ | $R^2$ | Mp (° C.) | HRMS (MH$^+$) |
|---|---|---|---|---|
| 7 | H$_3$CSO$_2$— | 2,6-dimethylphenyl | 220–225 | 498.2790 |

-continued
| Ex. | R⁸ | R² | Mp (° C.) | HRMS (MH⁺) |
|---|---|---|---|---|
| 7A | H₃CSO₂— | 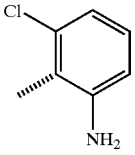 | 212–215 | 519.2197 |
| 7B | 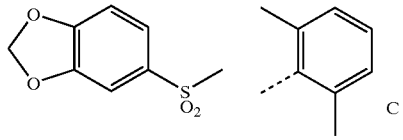 | 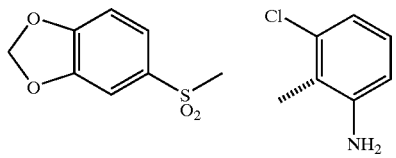 | 190 (dec.) | 604.2861 |
| 7C | 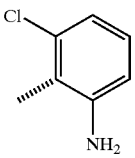 | 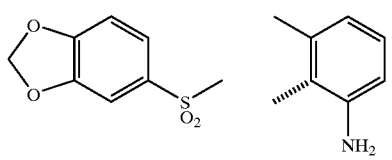 | 178 (dec.) | 625.2246 |
| 7D | 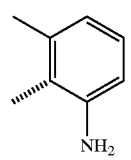 | 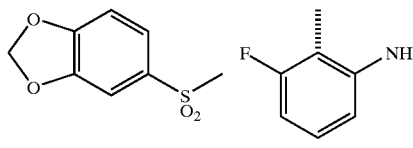 | 170 (dec.) | 605.2799 |
| 7E | 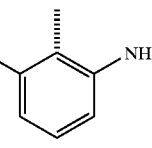 | 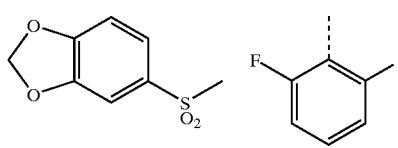 | 170 (dec.) | 609.2540 |
| 7F | 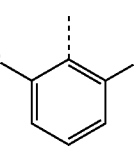 | 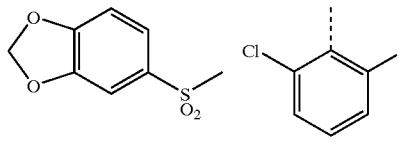 | 200 (dec.) | 612.2336 |
| 7G | 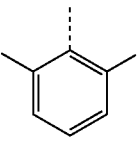 | 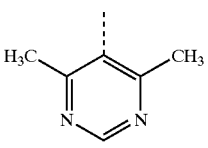 | 158 (dec.) | 644.1735 |
| 7H | H₃CSO₂— | 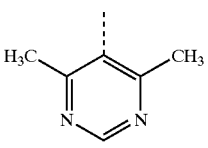 | 197 (dec.) | 514.2847 |

EXAMPLE 8

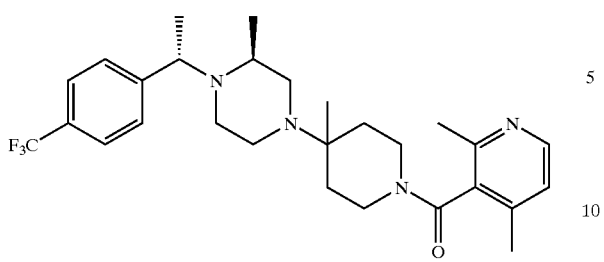

Step 1: A solution of the product of Example 4, step 4 (1.25 g; 4.6 mmol), N-BOC-4-piperidinone (0.91 g; 4.6 mmol) and (Ti(OiPr)$_4$) (1.4 ml; 4.6 mmol) in 10 ml of CH$_2$Cl$_2$ was stirred at ambient temperature for 24 h. The reaction mixture was then treated with Et$_2$AlCN (5.5 ml; 1M solution in toluene) and stirring continued for 20 h. The reaction mixture was diluted with EtOAc and stirred with saturated NaHCO$_3$ solution (10 min.) and the layers were separated as much as possible. The turbid (from inseparable aqueous layer) organic layer was treated with excess celite and filtered, washing the filtercake with EtOAc. The filtrate layers were separated and the organic layer was washed with water and brine, dried over anhydrous MgSO$_4$ and concentrated to obtain 2.16 g (98%) of an amber gum.

Step 2: The Strecker amine from step 1 (2.16 g) was dissolved in dry THF, cooled in an ice bath and treated with CH$_3$MgBr (7.5 ml of a 3M solution in Et$_2$O). After 1 h, the ice bath was removed and the yellow, heterogeneous reaction mixture was stirred at RT for 18 h. The reaction was quenched with saturated NH$_4$Cl solution, diluted with water and extracted with CH$_2$Cl$_2$. Concentration gave 2.2 g of a yellow gum which was purified by FSGC, eluting the major product away from more polar impurities using a 1:1 mixture of CH$_2$Cl$_2$:EtOAc. The ipso-methyl compound was isolated as a yellow gum (1.85 g; 88%). TLC R$_f$=0.5 in 1:1 Et$_2$O:hexanes.

Step 3: TFA (6 ml) was added to a solution of the product of step 2 (1.5 g; 3.2 mmol) in 10 ml of CH$_2$Cl$_2$ and stirred at 25° C. for 2 h. The reaction was quenched with 1N NaOH solution to a pH of 9–10 and processed by extraction into CH$_2$Cl$_2$ to obtain 1.2 g of crude product. FSGC using 1:1 CH$_2$Cl$_2$:EtOAc removed all the less polar impurities and gradient elution with 10% CH$_3$OH in CH$_2$Cl$_2$ and finally with 10% (ca. 7N—NH$_3$) CH$_3$OH in CH$_2$Cl$_2$ led to the isolation of the free piperidine as a yellow gum (1.07 g; 90%). TLC R$_f$=0.2 in 10% CH$_3$OH:CH$_2$Cl$_2$.

Step 4: A solution of the product of step 3 (1.03 g; 2.8 mmol), 2,4-dimethyl nicotinic acid (0.42 g; 2.8 mmol), DEC (0.8 g; 4.2 mmol), HOBT (0.57 g; 4.2 mmol) and diisopropyl ethyl amine (1 ml; 5.6 mmol) in CH$_2$Cl$_2$ (15 ml) was stirred at 25° C. for 24 h. The reaction mixture was diluted with CH$_2$Cl$_2$ (25 ml), washed with water, 10% NaHCO$_3$ solution and brine, then concentrated to obtain 1.6 g of crude oil. FSGC of this material using gradient elution with 10% acetone-CH$_2$Cl$_2$ followed by 2–5% CH$_3$OH in CH$_2$Cl$_2$ gave the title compound (1.1 g; 80%) as a white foam. TLC R$_f$=0.45 in 5% CH$_3$OH—CH$_2$Cl$_2$.

The free base of the title compound (1 g; 2 mmol) isolated above was dissolved in a 1:1 mixture of EtOAc:Et$_2$O (8 ml) and a fresh solution of hydrogen chloride in Et$_2$O (6.1 ml of a 1M solution) was added, instantly forming a white precipitate. After stirring at 25° C. for 1 h, the volatiles were removed in vacuo. The product was suspended in Et$_2$O and filtered, washing the filtrate with Et$_2$O. The HCl salt of the title compound thus obtained was dried in vacuo (1.1 g; mp. 213–215° C.). HRMS (MH$^+$) 503.2997.

The following amides 8A–8E were prepared in a similar manner from 10 the product of step 3 using appropriate acids, and compounds 8F–8H, wherein the R$^8$-substituent is a pmethyl sulfonyl group were similarly prepared.

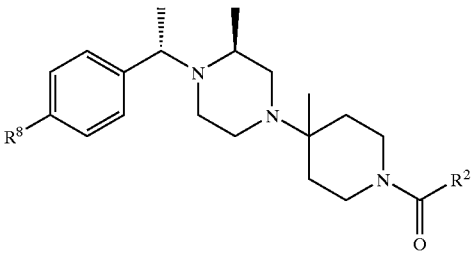

wherein R$^8$ and R$^2$ are defined in the table:

| Ex. | R$^8$ | R$^2$ | Mp (° C.) | HRMS (MH$^+$) |
|---|---|---|---|---|
| 8A | CF$_3$ | 2-methylaniline | 216 | 503.3021 |
| 8B | CF$_3$ | 2-methylphenol | 222–224 | 504.2850 |
| 8C | CF$_3$ | 2,6-dimethylphenyl | 262–263 | 502.3039 |
| 8D | CF$_3$ | 3-chloroaniline | 216–218 | 523.2466 |
| 8E | CF$_3$ | 2,4-dimethylpyridine N-oxide | 210–212 | 519.2970 |
| 8F | —SO$_2$CH$_3$ | 2,6-dimethylphenyl | 201–205 | 512.2955 |

-continued

| Ex. | R⁸ | R² | Mp (° C.) | HRMS (MH⁺) |
|---|---|---|---|---|
| 8G | —SO₂CH₃ | 3-chloro-2-aminophenyl | 217–221 | 533.2355 |
| 8H | —SO₂CH₃ | 2-methyl-6-hydroxyphenyl | 216–219 | 514.2736 |
| 8I | —CF₃ | 3,5-dimethylpyridine N-oxide | 195–198 | — |
| 8J | —CF₃ | 2,6-dichlorophenyl | 250–255 | 528.1791 |
| 8K | —CF₃ | 2,4,6-trichlorophenyl | 223–226 | 576.1562 |
| 8L | —CF₃ | 2,4,6-trifluorophenyl | >245 | 528.2439 |
| 8M | —CF₃ | 2-bromo-6-fluorophenyl | 176–181 | 570.1739 |
| 8N | —CF₃ | 2,6-dibromophenyl | 218–223 | 708.0040 |
| 8O | —CF₃ | 2-methyl-6-chlorophenyl | 215–220 | 522.2507 |
| 8P | —CF₃ | 2-methyl-6-bromophenyl | 208–212 | 566.1987 |
| 8Q | —CF₃ | 4-chloro-2-bromophenyl | 190–194 | 586.1442 |
| 8R | —CF₃ | 2-chloro-6-fluorophenyl | 255–257 | 526.2243 |

Using procedures described following the table, compounds 8S–8EE of the structure:

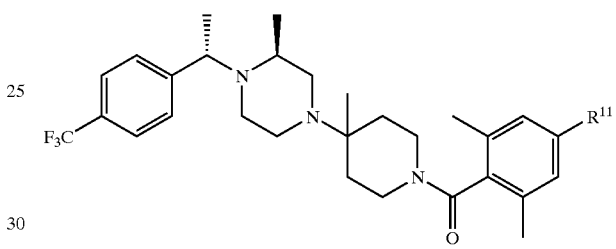

were prepared, wherein R¹¹ is defined in the table:

| Ex. | R¹¹ | Mp (° C.) | HRMS (MH⁺) |
|---|---|---|---|
| 8S | —OH | 210–220 (2 × HCl salt) | 518.2997 |
| 8T | —OC(O)NHCH₂CH₃ | 205–210 (2 × HCl salt) | 589.3374 |
| 8U | —OSO₂CH₃ | 165–171 (2 × HCl salt) | 596.2757 |
| 8V | 4-pyridyl N-oxide | 199–204 (2 × HCl salt) | 595.3254 |
| 8W | —CHO | 88–92 | 530.2985 |
| 8X | —CH=NH—OCH₃ | 202–205 (2 × HCl salt) | 559.3260 |
| 8Y | —CHF₂ | >245 (dec) (2 × HCl salt) | 552.3020 |
| 8Z | —NH—C(O)—NH—CH₂CH₃ | 214–219 (2 × HCl salt) | 588.3521 |
| 8AA | —NH₂ | 92–98 | 517.3154 |
| 8BB | —NHSO₂CH₂CH₃ | 205–211 (2 × HCl salt) | 609.3078 |
| 8CC | —F | 212–217 (2 × HCl salt) | 520.2949 |
| 8DD | —Cl | 235–238 (2 × HCl salt) | 536.2663 |
| 8EE | —Br | 237–240 (2 × HCl salt) | 580.2141 |

8S: The tri-hydrochloride salt of the product of Example 8, step 3 (75 mg, 0.16 mmol), EDC (61 mg, 0.32 mmol), HOBT (49 mg, 0.32 mmol), iPr₂NEt (0.16 ml, 0.96 mmol), and 2,6-dimethyl-4-hydroxy-benzoic acid (53 mg, 0.32 mmol) were taken up in CH₂Cl₂ and stirred at 25° C. for 20 h. The solution was concentrated. Purification via preparative TLC (EtOAc, SiO$_2$) gave the title compound as a yellow oil. m.p. (2×HCl salt) 210–220° C. HRMS (MH+) calcd. for C$_{29}$H$_{39}$O$_2$N$_3$F$_3$, 518.2994; Found, 518.2997.

8T: 8S (100 mg, 0.19 mmol), ethyl isocyanate (0.05 ml, 0.58 mmol), and Et$_3$N (0.13 ml, 0.95 mmol) were taken up in CH$_2$Cl$_2$ and stirred at 25° C. for 10 16 h. The solution was diluted with CH$_2$Cl$_2$ and washed with 1N NaOH. The organic layer was dried (Na$_2$SO$_4$), filtered, and concentrated. Purification via preparative TLC (2/1 EtOAc/hexanes, SiO$_2$) gave the title compound as a yellow oil.

8U: 8S (250 mg, 0.48 mmol), methane sulfonyl anhydride (250 mg, 1.44 mmol), and NaH (38 mg, 60 wt % in oil) were taken up in THF and stirred at 25° C. for 20 h. The solution was diluted with EtOAc and washed with sat'd NaHCO$_3$. The organic layer was dried (Na$_2$SO$_4$), filtered, and concentrated.

Purification via preparative TLC (1/1 EtOAc/hexanes, SiO$_2$) gave the title compound as a yellow oil (280 mg, 98%).

8V: The tri-hydrochloride salt of the product of Example 8, step 3 (50 mg. 0.1 mmol), EDC (38 mg, 0.2 mmol), HOBT (27 mg, 0.2 mmol), iPr$_2$NEt (0.07 ml, 0.4 mmol), and 2,6-dimethyl-4-(4-pyridyl-N-oxide)-benzoic acid (73 mg. 0.3 mmol) (see preparation below) were taken up in CH$_2$Cl$_2$ and stirred at 25° C. for 19 h. The solution was concentrated. Purification via preparative TLC (2/1 acetone/hexanes, SiO$_2$) gave 8V as a yellow oil (23 mg, 39%).

Preparation of 2,6-dimethyl-4-(4-pyridyl-N-oxide) Benzoic Acid

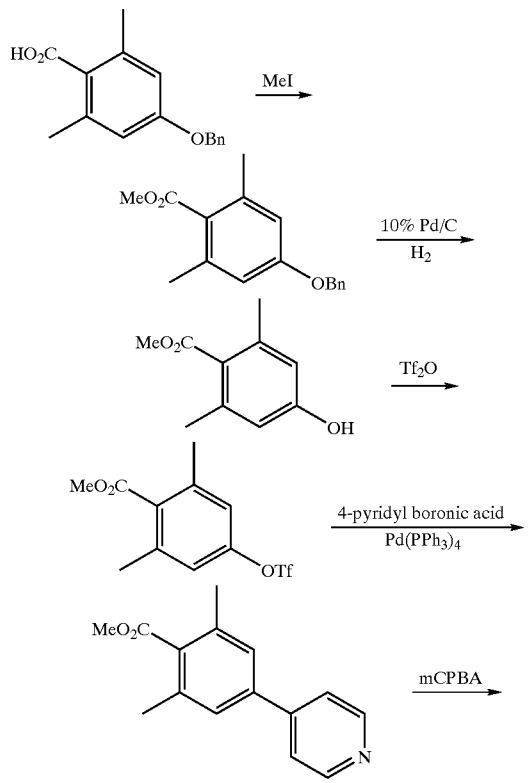

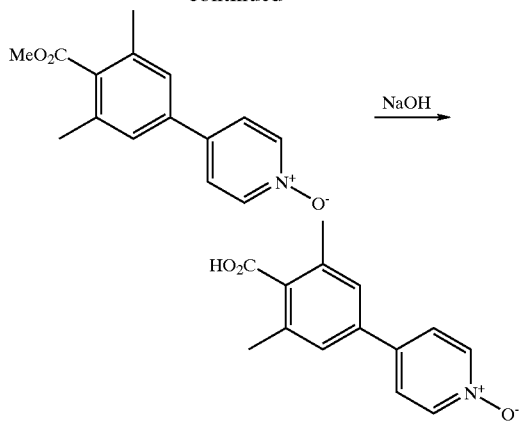

Step A: 4-Benzyloxy-2,6-dimethyl benzoic acid (8.7 g, 34 mmol; Thea, S. et al *Journal of the American Chemical Society* 1985, 50,1867), MeI (3.2 ml, 51 mmol), and Cs$_2$CO$_3$ (17 g, 51 mmol) were allowed to stir in DMF at 25° C. for 17 h. The solution was filtered and partitioned between Et$_2$O and water. The aqueous layer was extracted with Et$_2$O. The combined Et$_2$O layers were washed with H$_2$O and brine. The organic layer was dried (MgSO$_4$), filtered, and concentrated. Purification via flash chromatography (10/1 hexanes/Et$_2$O, SiO$_2$) gave 8.6 g (94%) of the methyl ester as a colorless oil.

Step B: The benzyl protected phenol (8.5 g, 32 mmol) and Pd/C (750 mg, 10 wt % Pd) were taken up in CH$_3$OH. The solution was charged with 50 psi H$_2$ and shaken in a Parr apparatus at 25° C. for 17h. The solution was filtered (Celite). Concentration gave 5.6 g (98%) of the phenol as a white solid.

Step C: The phenol (3.5 g, 19.4 mmol) and iPr$_2$NEt (3.76 g, 29.1 mmol) were dissolved in CH$_2$Cl$_2$ at 0° C. Triflic anhydride (Tf$_2$O) (4.2 ml, 25.2 mmol) was added dropwise to the solution at 0° C. The solution was warmed to 25° C. and stirred at that temperature for 4.5 h. The solution was diluted with CH$_2$Cl$_2$ and washed with sat NaHCO$_3$. The aqueous layer was extracted with CH$_2$Cl$_2$. The combined organic layers were dried over Na$_2$SO$_4$. Filtration and concentration gave the crude aryl triflate. Purification via flash chromatography (10/1, hexanes/EtO, SiO$_2$) gave 5.7 g (94%) of the triflate as a yellow oil.

Step D: The triflate (1 g, 3.2 mmol), 4-pyridyl boronic acid (1.2 g, 9.6 mmol), Pd(PPh$_3$)$_4$ (370 mg, 0.32 mmol), and Na$_2$CO$_3$ (1 g, 9.6 mmol) were taken up in DME/H$_2$O (4/1, 25 ml). The solution was heated to 90° C. (oil bath) under N$_2$ for 18 h. The solution was partitioned between EtOAc and H$_2$O. The aqueous layer was extracted with EtOAc. The combined EtOAc layers were dried (Na$_2$SO$_4$). Filtration and concentration gave a dark brown oil. Purification via flash chromatography (3/1 hexanes/EtOAc, SiO$_2$) gave 770 mg (100%) of the pyridyl derivative as an orange oil.

Step E: The pyridyl derivative (390 mg, 1.6 mmol) and mCPBA (550 mg, 3.2 mmol) were dissolved in CH$_2$Cl$_2$. The solution was stirred at 25° C. for 18 h. The solution was diluted with CH$_2$Cl$_2$ and washed with 1 N NaOH. The organic layer was dried (Na$_2$SO$_4$). Filtration and concentration gave 400 mg (97%) of the N-oxide as an orange oil. HRMS (MH$^+$) calcd. for C$_{15}$H$_{16}$O$_3$N, 258.1130; Found, 258.1131.

Step F: The methyl ester (400 mg, 1.6 mmol) was taken up in 5 ml of 3 N NaOH and 2 ml of EtOH. The solution was heated at reflux for 20 h. The solution was concentrated. The residue was treated with conc. HCl. The resulting solid was filtered and washed with water and brine. After drying under high vacuum, the free acid (377 mg, 100%) was obtained as a tan solid. m.p. >225° C. (decomp). HRMS (MH+) calcd. for $C_{14}H_{14}O_3N$, 244.0974; Found, 244.0981.

8W: The tri-hydrochloride salt of the product of Example 8, step 3 (1.34 g, 2.8 mmol), 2,6-dimethyl-4-formyl benzoic acid (500 mg, 2.8 mmol) (see preparation below), EDC (1.1 g, 5.6 mmol), HOBT (760 mg, 5.6 mmol) and iPrNEt (2 ml, 11 mmol) were subjected to the standard coupling conditions. Purification via flash chromatography (2/1 hexanes/EtOAc, SiO$_2$) gave 898 mg (61%) of 8W as a yellow foam.

Preparation of 2,6-dimethyl-4-formyl Benzoic Acid

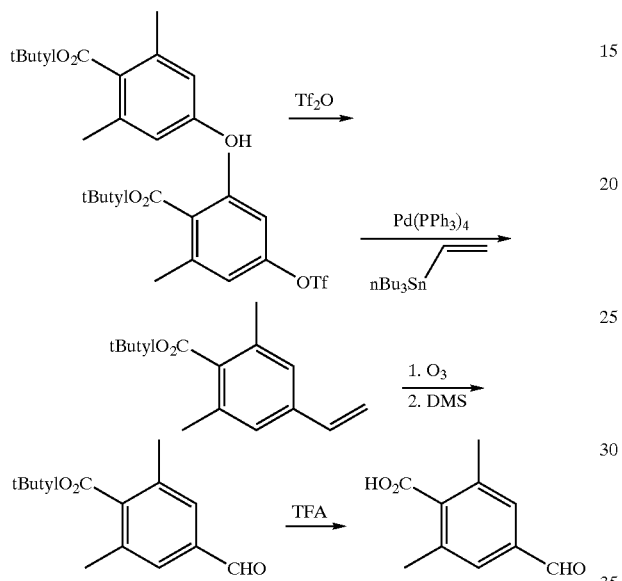

Step A: 4-Hydroxy-2,6-dimethyl-benzoic acid, tert-butyl ester (6.4 g, 29 mmol) and iPr$_2$NEt (5.6 g, 43 mmol) were taken up in CH$_2$Cl$_2$ and cooled to 0° C.. Tf$_2$O (5.8 ml, 34 mmol) was added slowly to the solution at 0° C. The solution was stirred at 0° C. for 3 h. The solution was partitioned between sat. NaHCO$_3$ and CH$_2$Cl$_2$. The aqueous layer was extracted with CH$_2$Cl$_2$. The combined organic layers were dried (Na$_2$SO$_4$). Filtration and concentration gave a brown oil. Purification via flash chromatography (20/1 hexanes/Et$_2$O, SiO$_2$) gave 7.99 g (82%) of the triflate as a yellow solid.

Step B: The triflate (5 g, 15 mmol), LiCl (1.25 g, 30 mmol), Pd(PPh$_3$)$_4$ (340 mg, 0.3 mmol), and vinyl tributyl tin (4.5 ml, 16 mmol) were taken up in THF under N$_2$. The solution was heated at 70° C. for 16 h. The solution was partitioned between EtOAc and sat. KF. The mixture was filtered. The organic layer was separated, and the aqueous layers were extracted with EtOAc. The combined organic layers were dried (MgSO$_4$). Filtration and concentration gave a yellow oil. Purification via flash chromatography (20/1 hexanes/Et$_2$O, SiO$_2$) gave 1.96 g (57%) of the olefin as a yellow oil.

Step C: The olefin (0.6 g, 2.6 mmol) was taken up in CH$_2$Cl$_2$/MeOH (1/1). The solution was cooled to −78° C. Ozone was bubbled through the solution until a dark blue color persisted. The reaction was quenched with dimethyl sulfide. The reaction was concentrated to furnish the aldehyde as an oil.

Step D: The tert-butyl ester (650 mg, 2.8 mmol) and TFA (3 ml) were taken up in CH$_2$Cl$_2$ and stirred at 25° C. for 19 h. Concentration of the solution gave the acid as a beige solid.

8X: 8W (100 mg, 0.19 mmol), H$_2$NOMe—HCl (28 mg, 0.34 mmol), NaOAc (32 mg, 0.46 mmol) were taken up in MeOH. The solution was stirred at 25° C. for 17 h. The solution was concentrated. The residue was partitioned between CH$_2$Cl$_2$ and 1 N NaOH. The aqueous layer was extracted with CH$_2$Cl$_2$. The combined organic layers were dried (Na$_2$SO$_4$). Filtration and concentration gave the crude product. Purification via preparative TLC (1/1 hexanes/EtOAc, SiO$_2$) gave 85 mg (84%) of 8X.

8Y: The tri-hydrochloride salt of the product of Example 8, step 3 (75 mg, 0.16 mmol) and 4-difluoromethyl-2,6-dimethyl benzoic acid (32 mg, 0.16 mmol) were subjected to the standard coupling conditions (EDC/HOBT/iPr$_2$NEt). Purification via preparative TLC (2/1 hexanes/EtOAc, SiO$_2$) gave 64 mg (73%) of 8Y.

Preparation of 4-difluoromethyl-2,6-dimethyl Benzoic Acid

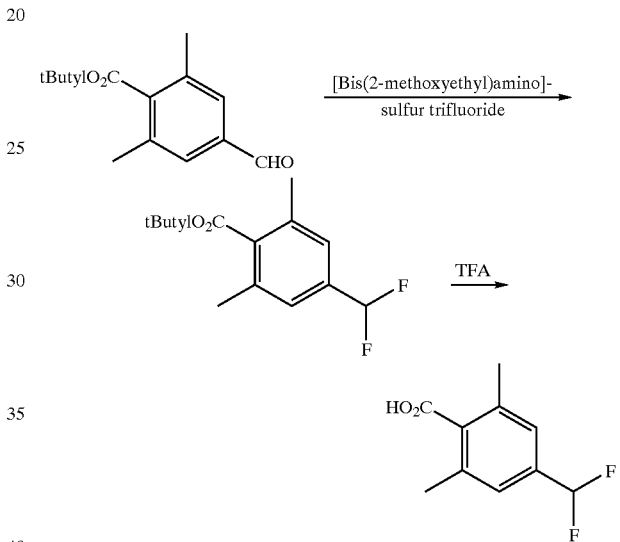

Step A: The aldehyde (400 mg, 1.7 mmol), [bis(2-methoxyethyl)amino]-sulfur trifluoride (640 mg, 2.9 mmol), and EtOH (0.02 ml, 0.34 mmol) were taken up 1,2-dichloroethane and stirred at 65° C. for 6 h and at 25° C. for 19 h. The solution was quenched with sat. NaHCO$_3$. The aqueous layer was extracted with CH$_2$Cl$_2$. The combined organic layers were dried (NaSO$_2$). Filtration and concentration gave the crude product. Purification via preparative TLC (10/1 hexanes/Et$_2$O, SiO$_2$) gave 210 mg (50%) of the difluoro derivative.

Step B: The tert-butyl ester (210 mg, 0.82 mmol) and HCl (2.1 ml of 4 M in dioxane, 8.2 mmol) were taken up in MeOH. The solution was stirred at 45° C. for 20 h. The solution was concentrated to obtain the acid as a white solid.

8Z: The tri-hydrochloride salt of the product of Example 8, step 3 (811 mg, 1.7 mmol) and 4-[(ethylamino)carbonylamino]-2,6-dimethyl benzoic acid (400 mg, 1.7 mmol) (see preparation below) were subjected to the standard coupling conditions (EDC/HOBT/iPr$_2$NEt). Purification via flash chromatography (1/1 hexanes/acetone, SiO$_2$) gave 803 mg (81%) of 8Z as a foam.

Preparation of 4-[(ethylamino)carbonylamino]-2,6-dimethyl Benzoic Acid

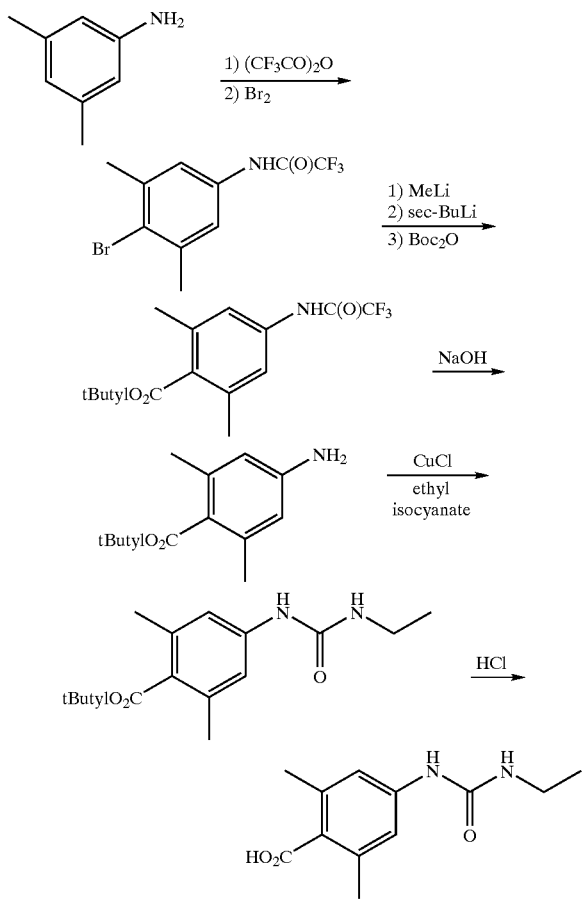

Step A: 3,5-Dimethyl aniline (18.5 ml, 149 mmol) was taken up in CH$_2$Cl$_2$. The solution was cooled in a water bath. Trifluoroacetic anhydride (29.5 ml, 209 mmol) was added slowly to the solution. After the addition, the solution was stirred at 25° C. for 15 minutes. Bromine (7.3 ml, 142 mmol) was added slowly to the solution while maintaining the RT water bath. The solution was stirred at 25° C. for 3.5 h. The solution was quenched with 10% Na$_2$S$_2$O$_3$. The aqueous layer was extracted with CH$_2$Cl$_2$. The combined organic layers were dried (MgSO$_4$), treated with activated carbon and filtered. Concentration gave an orange solid. Purification via recrystallization (hexanes/Et$_2$O) gave two crops (34 g total, 77%) of the brominated derivative as a white solid.

Step B: The aryl bromide (17 g, 57 mmol) was taken up in THF and cooled to −78° C. under N$_2$. Methyllithium/LiBr (54 ml of a 1.5 M solution in Et$_2$O, 80 mmol) was added slowly to the solution at −78° C. After 5 min of stirring, sec-BuLi (62 ml of a 1.3 M in cyclohexane, 80 mmol) was added slowly to the reaction solution at −78° C. After 5 min, di-t-butyl dicarbonate (22.5 g, 103 mmol) in THF was added to the solution at −78° C. The solution was warmed to 25° C. After 30 min, the reaction mixture was partitioned between water and CH$_2$Cl$_2$. The aqueous layer was extracted with CH$_2$Cl$_2$. The combined organic layers were dried (MgSO$_4$). Filtration and concentration gave a yellow solid.

Purification via flash chromatography (1/1 to 1/4 hexanes/CH$_2$Cl$_2$, SiO$_2$) gave 13.1 g (72%) of the tert-butyl ester as an off-white solid.

Step C: The trifluoro-acetamide (10 g, 31 mmol) and NaOH (2.5 g, 62 mmol) were taken up in MeOH/H$_2$O (3/1) and heated at 60° C. for 3 h. The solution was partitioned between CH$_2$Cl$_2$ and water. The aqueous layer was extracted with CH$_2$Cl$_2$. The combined organic layers were washed with water and dried (Na$_2$SO$_4$). Filtration and concentration gave 6.4 g (93%) of the aniline as an orange solid.

Step D: The aniline (1 g, 4.5 mmol), ethyl isocyanate (0.4 ml, 5 mmol), and CuCl (90 mg, 0.9 mmol) were taken up in DMF at 0° C. The solution was warmed to 25° C. and stirred at that temperature for 2 h. The solution was partitioned between EtOAc and 10% NH$_4$OH. The aqueous layer was extracted with EtOAc. The combined layers were washed with brine and dried (MgSO$_4$). Filtration and concentration gave a yellow solid. Purification via flash chromatography (3/1 to 1/1 hexanes/EtOAc, SiO$_2$) gave 904 mg (69%) of the urea as a yellow solid.

Step E: The tert-butyl ester (900 mg, 3.1 mmol) and 4 M HCl in dioxane (3 ml) were taken up in iPrOH and heated at 45° C. for 3.5 h and at 25° C. for 16.5 h. The solution was concentrated under reduced pressure. The residue was partitioned between Et$_2$O and 1 N NaOH. The aqueous, basic layer was extracted with Et$_2$O. The aqueous layer was cooled to 0° C. and acidified with conc. HCl (pH=1–2). The aqueous layer was extracted with EtOAc. The combined EtOAc layers were dried (Na$_2$SO$_4$). Filtration and concentration gave the 400 mg (55%) of the acid as a white solid.

8AA: The tri-hydrochloride salt of the product of Example 8. step 3 (2 g, 4.3 mmol) and 4-amino-2,6-dimethyl benzoic acid (710 mg, 4.3 mmol) (see preparation below) were subjected to the standard coupling conditions (EDC/HOBT/iPr$_2$NEt). Purification via flash chromatography (2/1 hexanes/acetone, SiO$_2$) gave 1.16 g (52%) of 8AA as a yellow foam.

Preparation of 4-amino-2,6-dimethyl Benzoic Acid

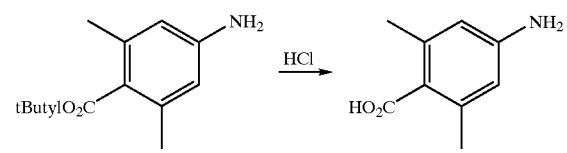

The tert-butyl ester (950 mg, 4.3 mmol) and HCl (11 ml, 4 M in dioxane) were taken up in MeOH at heated at 45° C. for 20 h. The solution was concentrated to obtain the acid (710 mg) in quantitative yield.

8BB: 8AA (100 mg, 0.19 mmol) and ethane sulfonyl chloride (0.02 ml, 0.21 mmol) were taken up in pyridine and stirred at 25° C. for 19 h. The solution was concentrated. The residue was partitioned between 1 N NaOH and CH$_2$Cl$_2$. The aqueous layer was extracted with CH$_2$Cl$_2$. The combined organic layers were dried (Na$_2$SO$_4$). Filtration and concentration gave a brown oil. Purification via preparative TLC (2/1 hexanes/acetone, SiO$_2$) gave 100 mg (86%) of 8BB as a colorless oil.

8CC: The trihydrochloride salt of the product of Example 8, step 3 (127 mg, 0.27 mmol) and 4-fluoro-2,6-dimethyl benzoic acid (58 mg, 0.35 mmol) (see preparation below) were coupled according to the general procedure (EDC/HOBT/iPr₂NEt). Purification via preparative TLC (2/1 hexanesl EtOAc, SiO₂) gave 8CC as a colorless oil (87 mg bis-HCl salt, 54%).

Preparation of 4-fluoro-2.6-dimethyl Benzoic Acid

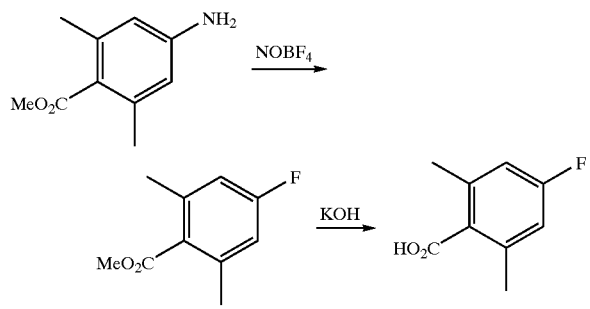

4-Amino-2,6-dimethyl benzoic acid (200 mg, 1.1 mmol) and NOBF₄ (196 mg, 1.7 mmol) were heated in 1,2-dichlorobenzene at 100° C. for 30 min. The solution was cooled and diluted with MeOH and water. A few pellets (2–3) of KOH were added, and the solution was heated at reflux for 16 h. The solution was concentrated. The residue was partitioned between Et₂O and 1 N NaOH. The aqueous layer was extracted with Et₂O. The aqueous layer was cooled to 0° C. and acidified with conc. HCl (pH=1–2). The aqueous layer was extracted with CH₂Cl₂. The organic layers were dried (Na₂SO₄). Filtration and concentration gave 58 mg (31%) of the acid as a tan solid.

8DD: The trihydrochloride salt of the product of Example 8, step 3 (150 mg, 0.31 mmol) and 4-chloro-2,6-dimethyl benzoic acid (76 mg, 0.41 mmol) (see preparation below) were coupled according to the general procedure (EDC/HOBT/iPr₂NEt). Purification via preparative TLC (4/1 hexanes/acetone, SiO₂) gave 8DD as a colorless oil.

Preparation of 4-chloro-2,6-dimethyl Benzoic Acid

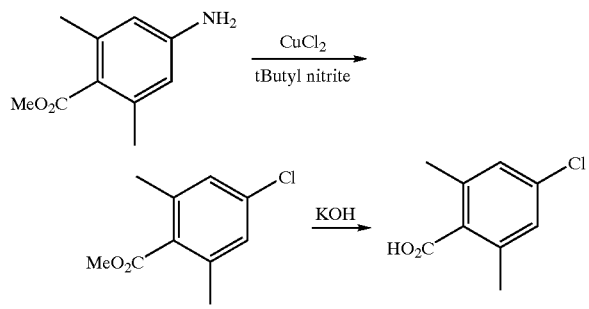

4-Amino-2,6-dimethyl benzoic acid (172 mg, 0.96 mmol) and CuCl₂ (155 mg, 1.15 mmol) were taken up in CH₃CN at 0° C. Tert-butyl nitrite (0.17 ml, 1.4 mmol) was added to the solution at 0° C. The solution was warmed to 25° C. and then at 65° C. for 45 min. The solution was partitioned between Et₂O and water. The aqueous layer was extracted with Et₂O. The combined organic layers were washed with brine and dried (MgSO₄). Filtration and concentration gave the methyl ester. The methyl ester was hydrolyzed as described above for the fluoro derivative (KOH). After extractive workup, 4-chloro-2,6-dimethyl benzoic acid (158 mg, 89%) was obtained as a yellow solid.

8EE: The trihydrochloride salt of the product of Example 8, step 3 (180 mg, 0.38 mmol) and 4-bromo-2,6-dimethyl benzoic acid (95 mg, 0.41 mmol) (see preparation below) were coupled according to the general procedure (EDC/HOBT/iPr₂NEt). Purification via preparative TLC (4/1 hexanes/acetone, SiO₂) gave 8EE as a colorless oil (140 mg bis-HCl salt, 56%).

Preparation of 4-bromo-2,6-dimethyl Benzoic Acid

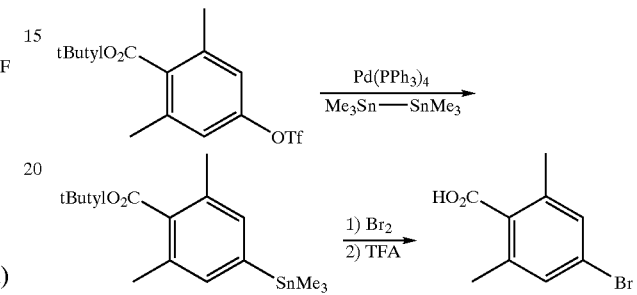

Step A: The triflate (500 mg, 1.48 mmol), hexamethyiditin (0.31 mmol, 1.48 mmol), LiCl (377 mg, 8.9 mmol), and Pd(PPh₃)₄ (171 mg, 0.15 mmol) were heated in THF (70° C.) under N₂ for 21 h. The solution was partitioned between Et₂O and pH=7 buffer (NH₄OAc). The aqueous layer was extracted with Et₂O. The combined Et₂O layers were washed with brine and dried (Na₂SO₄). Filtration and concentration gave the crude aryl stannane as a yellow semi-solid.

Step B: The aryl stannane (0.74 mmol) was taken up in CH₂Cl₂ at 0° C. Bromine (0.7 ml of 1 M Br₂ in CH₂Cl₂) was added to the solution. The solution was stirred at 0° C. for 30 min. The solution was diluted with CH₂Cl₂ and washed with 10% Na₂S₂O₃. The aqueous layer was extracted with CH₂Cl₂. The combined organic layers were dried (Na₂SO₄). The solution was filtered. TFA (2 ml) was added to the solution, and the solution was stirred at 25° C. for 17 h. The solution was concentrated. The residue was partitioned between Et₂O and 1 N NaOH. The aqueous layer was extracted with Et₂O. The aqueous layer was cooled to 0° C. and acidified with conc. HCl (pH=1–2). The aqueous layer was extracted with CH₂Cl₂. The combined organic layers were dried (Na₂SO₄). Filtration and concentration gave 100 mg (59%) of the acid as a white solid.

Using procedures described following the table, compounds 8FF–8HH of the structure:

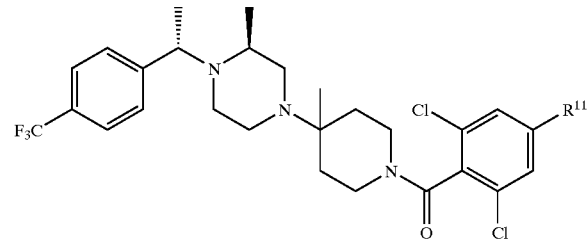

were prepared, wherein R[11] is defined in the table:

| Ex. | R[11] | Mp (° C.) | HRMS (MH+) |
|---|---|---|---|
| 8FF | —OCH$_3$ | 217–220 (2 × HCl salt) | 572.2048 |
| 8GG | —OH | 198–204 (2 × HCl salt) | 558.1898 |
| 8HH | (pyridyl-N-oxide group) | 200–205 (2 × HCl salt) | 635.2172 |

8FF: The trihydrochloride salt of the product of Example 8, step 3 (100 mg, 0.21 mmol) and 2,6-dichloro-4-methoxy-benzoic acid (140 mg, 0.63 mmol) were coupled according to the general procedure (EDC/HOBT/iPr$_2$NEt). Purification via preparative TLC (3/1 hexanes/EtOAc, SiO$_2$) gave 8FF as a colorless oil (27 mg, 23%).

8GG: The trihydrochloride salt of the product of Example 8, step 3 (330 mg, 0.7 mmol) and 2,6-dichloro-4-hydroxy-benzoic acid (290 mg, 1.4 mmol) (see preparation below) were coupled according to the general procedure (EDC/HOBT/iPr$_2$NEt). Purification via preparative TLC (1/1 hexanes/EtOAc, SiO$_2$) gave 8GG as a colorless oil (75 mg, 19%).

Preparation of 2,6-dichloro-4-hydroxy-benzoic Acid

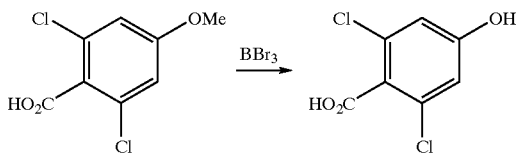

2,6-Dichloro-4-methoxy-benzoic acid (500 mg, 2.3 mmol) was taken up in CH$_2$Cl$_2$ and cooled to −78° C. BBr$_3$ (6.9 ml of a 1 M solution in CH$_2$Cl$_2$) was added to the solution at −78° C. The solution was warmed to 25° C. and stirred at that temperature for 16 h. The solution was quenched with 3 N NaOH. The aqueous layer was extracted with CH$_2$CO$_2$. The aqueous layer was cooled (0° C.) and acidified with conc. HCl (pH=1–2). The aqueous layer was extracted with CH$_2$Cl$_2$. The combined organic layers were dried (Na$_2$SO$_4$). Filtration and concentration gave the crude phenol which was used without further purification.

8HH: The trihydrochloride salt of the product of Example 8, step 3 (96 mg, 0.2 mmol) and 2,6-dichloro-4-(4-pyridyl-N-oxide)-benzoic acid (55 mg, 0.2 mmol) (see preparation below) were coupled according to the general procedure (EDC/HOBT/iPr$_2$NEt). Purification via preparative TLC (1/5 hexanes/acetone, SiO$_2$) gave 8HH as a colorless oil (54 mg, 43%).

Preparation of 2,6-dichloro-4-(4-pyridyl-N-oxide) Benzoic Acid

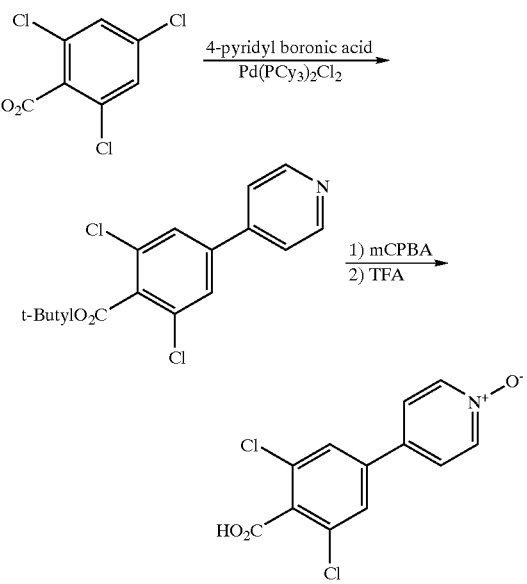

2,4,6-Trichloro benzoic acid, tert-butyl ester (500 mg, 1.8 mmol), 4-pyridyl boronic acid (270 mg, 2.16 mmol), Pd(PCy$_3$)$_2$Cl$_2$ (130 mg, 0.18 mmol), and CsF (540 mg, 3.6 mmol) were taken up in NMP and heated at 100° C. under N$_2$ (16 h). The solution was partitioned between EtOAc and water. The aqueous layer was extracted with EtOAc. The combined organic layers were washed with water and brine and dried (Na$_2$SO$_4$). Filtration and concentration gave the crude product. Purification via preparative TLC (1/1 hexanes/EtOAc, SiO$_2$) gave 68 mg (12%) of the pyridyl ester. The tert-butyl ester was converted into the acid as done previously for the dimethyl derivative (a. mCPBA /b. TFA).

Using suitable starting materials and the procedures described for examples 8S to 8HH, the compounds of the following structure were prepared:

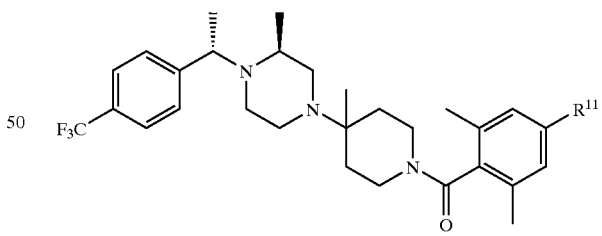

wherein R[11] is defined in the table

| Ex. | R[11] | m.p. (° C.) | HRMS (MH+) calc. | HRMS (MH+) found |
|---|---|---|---|---|
| 8II | —OCH$_3$ | 236–240 | 532.3151 | 532.3166 |
| 8JJ | —CH$_3$ | >260 | 516.3202 | 516.3213 |

-continued

| Ex. | R11 | m.p. (° C.) | HRMS (MH+) calc. | HRMS (MH+) found |
|---|---|---|---|---|
| 8KK | isopropyl carbamate | 186–190 | 603.3522 | 603.3513 |
| 8LL | 4-pyridyl | 202–208 | 579.3311 | 579.3303 |
| 8MM | 3-pyridyl | 210–216 | 579.3311 | 579.3311 |
| 8NN | 3-pyridyl N-oxide | 196–203 | 595.3260 | 595.3256 |
| 8OO | phenyl | >230 (dec) | 578.3358 | 578.3368 |
| 8PP | t-butyl carbamate | 135–140 | 617.3679 | 617.3671 |
| 8QQ | t-butyl urea | 205–215 | 602.3682 | 602.3722 |
| 8RR | CH2OH | >235 (dec) | 532.3151 | 532.3124 |
| 8SS | 2-pyrimidyl | 206–212 | 580.3263 | 580.3258 |
| 8TT | 2-pyridyl | 198–204 | 579.3311 | 579.3315 |
| 8UU | 2-pyrazinyl | 231–236 | 580.3263 | 580.3252 |

-continued

| Ex. | R¹¹ | m.p. (° C.) | HRMS (MH⁺) calc. | HRMS (MH⁺) found |
|---|---|---|---|---|
| 8VV | −NHC(O)CF₃ | 201–207 | 613.2977 | 613.2981 |
| 8WW | −OS(O)₂CF₃ | 215–220 | 650.2487 | 650.2497 |
| 8XX | −CH=NOH | 198–201 | 545.3103 | 545.3098 |
| 8YY | −NHS(O)₂CH₃ | 210–214 | 595.2930 | 595.2921 |
| 8ZZ | CH₂F | >245 | 534.3108 | 534.3117 |
| 8AB | −NHS(O)₂NMe₂ | 202–205 | 624.3195 | 624.3204 |
| 8AC | −NHC(O)CH₃ | 208–213 | 559.3260 | 559.3263 |
| 8AD | −NHC(O)NH₂ | 215–220 | 560.3212 | 560.3220 |
| 8AE | −C(O)NHEt | 215–220 | 573.3416 | 573.3424 |
| 8AF | −C(O)NHMe | 215–220 | 559.3260 | 559.3257 |
| 8AG | −NHC(O)NH-propyl | 205–209 | 602.3682 | 602.3672 |
| 8AH | −NHC(O)NHMe | 186–192 | 574.3369 | 574.3378 |
| 8AI | −NHC(O)NH-tBu | 200–206 | 616.3838 | 616.3844 |

-continued

| Ex. | R¹¹ | m.p. (° C.) | HRMS (MH⁺) calc. | HRMS (MH⁺) found |
|---|---|---|---|---|
| 8AJ | ⟲–C(O)–N(CH₂CH₂OMe)₂ | 165–173 | 661.3941 | 661.3949 |
| 8AK | CN | 240–250 | 527.2998 | 527.2991 |
| 8AL | ⟲–NH–C(O)–NH–CH₂CH₂Cl | 211–215 | 622.3136 | 622.3129 |
| 8AM | ⟲–NH–C(O)–NH–butyl | 170–174 | 616.3838 | 616.3836 |
| 8AN | ⟲–NH–C(O)–NH–CH₂–cyclopropyl | 192–196 | 614.3682 | 614.3690 |

All melting points were done on the bis hydrochloride salts (2 × HCl) except 8PP was performed on the free base Using derivatives of the triflate intermediate described in 8Z in procedures similar to those described above and following the table for 8AO–8AQ, the compounds of the following structure were prepared:

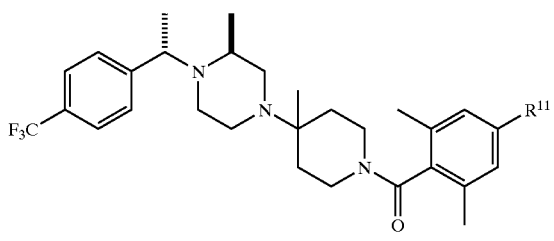

wherein R¹¹ is defined in the table

| Ex. | R¹¹ | m.p. (° C.) |
|---|---|---|
| 8AO | —CN | 240–250 |
| 8AP | —CONHEt | 215–220 |
| 8AQ | —N(CH₃)CONHEt | 186–203 |
| 8AR | —CONH₂ | 200–208 |
| 8AS | —CONHCH₃ | 215–220 |
| 8AT | —CON(CH₂CH₂OCH₃)₂ | 165–173 |
| 8AU | —CON(Et)₂ | 170–180 |
| 8AV | —N(CH₃)CONHCH₃ | 198–210 |
| 8AW | —NHCH₃ | 190–200 |
| 8AX | —N(CH₃)CONH₂ | 190–220 |

8AO:

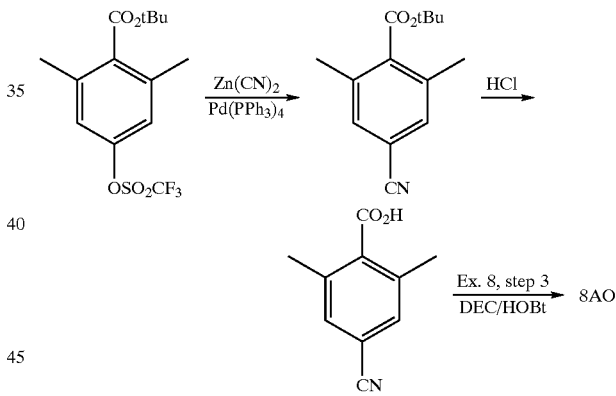

Step 1: The triflate intermediate (see 8W) (0.4 g), Zn(CN)₂ (0.2 g), Pd(PPh₃)₄ (0.3 g) and DMF (1.5 ml) were heated at 80° C. for 17 h. The 10 reaction was cooled to RT, diluted with EtOAc and saturated aqueous NaHCO₃. The EtOAc layer was removed, washed with water, dried with brine and evaporated to give a crude oil which was purified by preparative plate chromatography (2000 μM silica plates; 8:1 hexanes:EtOAc eluant), to give, after isolation of the appropriate band, the cyano intermediate (0.2 g) in 77% yield.

Step 2: The product of Step 1 (0.2 g) was dissolved in MeOH (1.5 ml) and HCl (4M solution in 1,4-dioxane; 2 ml) was added. The resulting solution was stirred at 50° C. for 3 h and evaporated. This crude intermediate (0.038 g) and the product of Example 8, Step 3 (65 mg; trihydrochloride form) were treated in the same fashion as Example 8, Step 4, using DMF (2 ml), HOBt (45 mg), DEC (60 mg) and diisopropyl ethyl amine (0.1 ml) to give, after isolation and purification, the free base form of 8AO, which was converted to its HCl salt (45 mg) in 95% yield.

8AP:

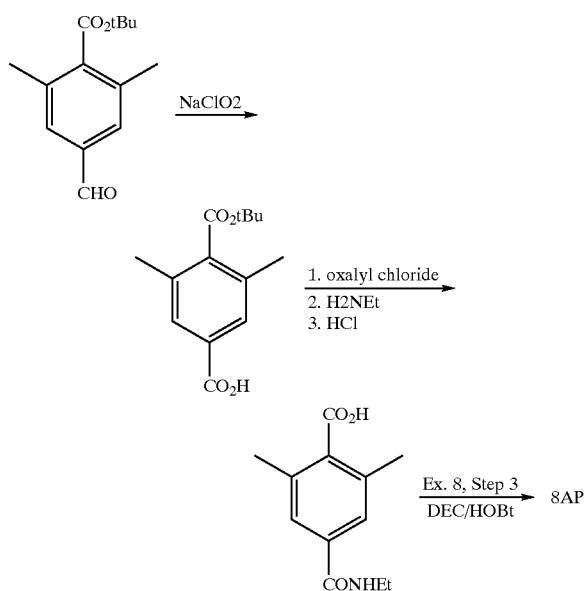

Step 1: 2,6-Dimethyl-4-formyl benzoic acid (1.96 g) (see 8W) was dissolved in t-butanol (94 ml) and 2-methyl-2-butene (24 ml). A solution of $NaClO_2$ (6.89 g), $NaH_2PO_4$ monohydrate (8.17 g) and water (45 ml) was added dropwise to the first solution. After complete addition, the pH was adjusted to 3 and two layers resulted. The organic layer was removed and evaporated to give intermediate acid (1.80 g) as a white crystalline solid, which was used without purification.

Step 2: To a solution of the product of Step 1 (0.62 g), $CH_2Cl_2$ (5 ml) and DMF (1 drop) was added oxalyl chloride (0.31 ml) and the resulting solution was stirred for 10 min, at which time a second portion of oxalyl chloride (0.30 ml) was added. The reaction was stirred for 10 min, toluene was added and the mixture was evaporated to dryness. $CH_2Cl_2$ (10 ml) and $EtNH_2$ (1 ml) were added and the reaction was stirred for 2 days, then partitioned between brine and $CH_2Cl_2$. The $CH_2Cl_2$ layer was evaporated and HCl (4 ml of a 4 M solution in 1,4-dioxane) was added. The resulting solution was stirred for 3 h and evaporated to give a solid which was washed with $Et_2O$ and collected to give the amide intermediate (0.13 g) in 24% yield.

Step 3: The product of Example 8, Step 3 (60 mg; trihydrochloride form) and the product of step 2 (35 mg) were treated in the same fashion as Example 8, Step 4 to give, after work up and purification, BAP as the free base form, which was converted to the HCl salt (50 mg) in 62% yield.

8AQ:

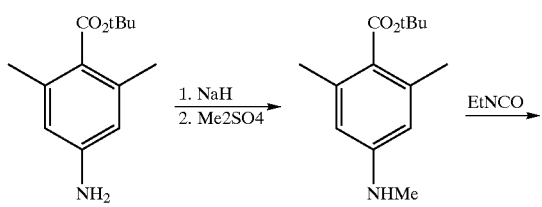

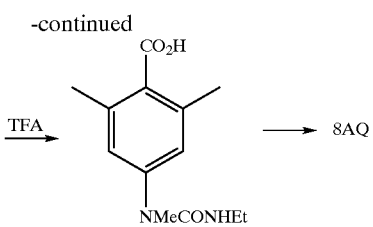

Step 1: To a solution of the amine intermediate (2 g) (see 8Z) was added NaH (0.4 g of a 60% oil dispersion). The resulting suspension was stirred for 15 min and $Me_2SO_4$ was added. After heating at reflux for 1.5 h, the reaction was cooled to RT, poured into saturated $NH_4Cl$ aqueous solution and extracted with $Et_2O$. After evaporation, the crude reaction mixture was chromatographed on silica gel, eluting with 4:1 hexanes:EtOAc, to give, after evaporation of the appropriate fractions, the methylamine intermediate (0.8 g) in 38% yield.

Step 2: The product of Step 1 (0.12 g), THF (5 ml) and EtNCO (54 mg) were heated at reflux for 17 h. EtNCO (54 mg) and 1,4-dioxane (2 ml) were added and the resulting solution was heated in a sealed tube at 65° C. for 17 h. The solution was cooled, evaporated and purified by preparative plate chromatography (silica gel; 25% EtOAc:$CH_2Cl_2$), to give the desired product (0.1 g) as a crystalline solid in 64% yield.

Step 3: The product of Step 2 (0.1 g) was treated in the same fashion as Example 8, Step 3 (p 28) to give the desired intermediate (0.08 g) which was used directly in the next step.

Step 4: The product of Example 8, Step 3(75 mg; trihydrochloride form) and the product of Step 3 (0.04 g) were treated in the same fashion as Example 8, Step 4, to give, after work up and purification, 8AQ as the free base form, which was converted to the HCl salt (65 mg) in 62% yield.

Using procedures described above and employing commercially available acids, compounds 8AY–8BT of the structure:

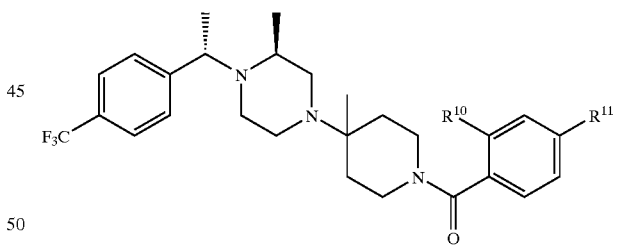

were prepared, wherein $R^{10}$ and $R^{11}$ are defined in the table:

| Ex. | $R^{10}$ | $R^{11}$ | Mp (° C.) |
|---|---|---|---|
| 8AY | —$CH_3$ | H | 205–208 |
| 8AZ | F | H | 250–255 |
| 8BA | Cl | H | 215–217 |
| 8BC | —$CH_3$ | Br | 228–231 |
| 8BD | —$CH_3$ | ![4-pyridyl] | 194–198 |

-continued

| Ex. | R¹⁰ | R¹¹ | Mp (° C.) |
|---|---|---|---|
| 8BE | Cl | Cl | 240–241 |
| 8BF | Cl | F | 268–270 |
| 8BG | Br | H | 210–213 |
| 8BH | Cl | Br | 213–217 |
| 8BI | Br | F | 176–181 |
| 8BJ | I | H | 184–190 |
| 8BK | —CF₃ | F | 204–209 |
| 8BL | F | F | 268–270 |
| 8BM | Cl | NH₂ | 215–220 |
| 8BN | H | F | 258–260 |
| 8BO | H | Br | 238–240 |
| 8BP | H | Cl | 235–240 |
| 8BQ | Br | Cl | 190–194 |
| 8BR | CH₃CH₂— | H | 211–214 |
| 8BS | —Si(CH₃)₃ | H | 230–240 |
| 8BT | Cl | NO₂ | 275–280 |

Using procedures similar to those described above, the following compounds were prepared:

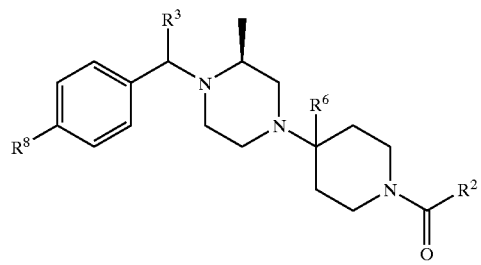

wherein R⁸, R³, R⁶ and R² are defined in the table:

| Ex. | R⁸ | R³ | R⁶ | R² | Mp (° C.) |
|---|---|---|---|---|---|
| 8BU | —CF₃ | CH₃ | —CH₃ | 4-methylpyrimidin-5-yl | 195–220 |
| 8BV | —CF₃ | CH₃ | —CH₃ | 4-(trifluoromethyl)pyrimidin-5-yl | 80–85 |
| 8BW | —CF₃ | CH₃ | —CH₃ | 4-fluoro-2,6-dimethylphenyl | 212–217 |
| 8BX | —CF₃ | CH₃ | —CH₃ | 4-chloro-2,6-dimethylphenyl | 235–238 |
| 8BY | —CF₃ | CH₃ | —CH₃ | 4-[B(OC(CH₃)₂)₂]-2,6-dimethylphenyl | 195–200 |
| 8BZ | —CF₃ | CH₃ | —CH₃ | 4-bromo-2,6-dimethylphenyl | 237–240 |

-continued

| Ex. | R⁸ | R³ | R⁶ | R² | Mp (° C.) |
|---|---|---|---|---|---|
| 8CA | —CF₃ | CH₃ (dashed) | —CH₂CH₃ | 4,6-dimethylpyrimidin-5-yl | 179–181 |
| 8CB | —CF₃ | isopropyl (dashed) | —CH₂CH₃ | 4,6-dimethylpyrimidin-5-yl | 200–202 |
| 8CD | —CF₃ | isopropyl (dashed) | —CH₂CH₃ | 2,6-dimethyl-4-(NHCONHEt)phenyl | 199–205 |
| 8CE | F₃C-C(O)-NH-CH₂- | CH₃ (dashed) | —CH₃ | 2,6-dimethylphenyl | 206–210 |
| 8CF | —CF₃ | cyclopropylmethyl (dashed) | —CH₃ | 4,6-dimethylpyrimidin-5-yl | 235–239 |

EXAMPLE 9

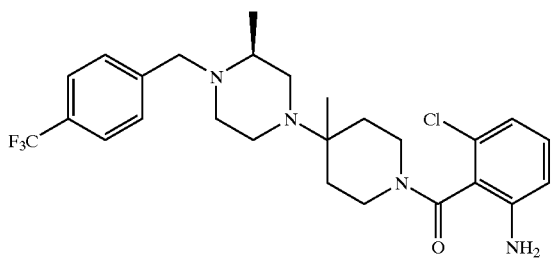

Step 1: A solution of 4-N-BOC-2(S)-methyl piperazine (1.5 g; 7.5 mmol), 4-methoxy-benzyl chloride (1.1 ml; 8.1 mmol) and diisopropyl ethyl amine (1.5 ml) in dry CH₃CN were heated at reflux for 5 h. The reaction mixture was cooled to RT and volatiles were removed in vacuo. The residue was dissolved in CH₂Cl₂ (30 ml) and washed with water and brine. Concentration gave the crude product, which was purified by FSGC (10% EtOAc-hexanes) to obtain 2.1 g (88%) of product as a pale yellow liquid.

TFA (6 ml) was added to a solution of the above compound (2.1 g; 6.56 mmol) in 12 ml of CH₂Cl₂ and the mixture stirred at 25° C. for 1.5 h. The reaction was quenched with 1N NaOH and adjusted to pH 10. Extractive work-up in CH₂Cl₂ furnished the desired product (1.4 g; 97%) as a colorless gum.

Step 2: A mixture of the product of step 1 (1.4 g; 6.36 mmol), N-BOC-4-piperidinone (1.27 g; 6.4 mmol) and Ti(OiPr)₄ (1.9 ml; 6.4 mmol) was stirred at 25° C. for 24 h. A 1M solution of Et₂AlCN in toluene (7.6 ml) was added to the reaction mixture and the mixture stirred at ambient temperature for another day. The Strecker amine thus formed was worked-up and isolated (2.7 g; 100%) as described in Example 8, step 2. TLC R_f=0.3 in 25% EtOAc-CH₂Cl₂.

The Strecker amine (2.7 g; 6.3 mmol) was dissolved in 15 ml of dry THF at 0° C. and CH₃MgBr (3M in Et₂O; 10.5 ml) was added to it. After 1 h, the ice bath was removed and the reaction allowed to proceed at RT for 15 h. TLC analysis of the heterogeneous reaction mixture showed no change from the starting material; the mixture was warmed at 60° C. for 5 h with no observed change in TLC behavior. The reaction mixture was quenched with saturated NH₄Cl and organic products extracted into CH₂Cl₂. FSGC of the crude product (2.7 g) using 15% acetone-hexanes as the eluant provided the desired ipso-methyl compound as a colorless gum (2.3 g; 87%).

Step 3: The product of step 2 (1.7 g; 4.08 mmol), ammonium formate (1.4 g; 22 mmol) and 10% palladium on carbon (0.4 g) were mixed in 20 ml of CH₃OH and heated at reflux for 5 h. The reaction mixture was filtered through celite and volatiles were removed. The residue was dissolved in CH₂Cl₂ and washed with 10% NaOH solution, water and brine. Concentration in vacuo gave 1.1 g (92%) of pale yellow gum.

Step 4: A solution of the product of step 3 (0.12 g; 0.4 mmol), p-trifluoromethyl benzyl bromide (0.1 g; 0.4 mmol) and diisopropyl ethyl amine (0.1 ml) in dry CH₃CN was gently warmed (60–70° C.) for 16 h. The mixture was cooled and organic product isolated via extractive work-up in CH₂Cl₂. FSGC (10–30% Et₂O-CH₂Cl₂; R_f=0.4) yielded the major product as a colorless film (0.12 g; 68%).

Treatment of the above product (in CH₂Cl₂) with TFA (1 ml) for 1 h followed by basification and standard work-up provided the desired compound (0.09 g; 96%) as a colorless film.

Step 5: The product of step 4 (0.045 g; 0.13 mmol) and 6-chloro anthranilic acid (0.022 g; 0.13 mmol) were coupled as described in Example 1 and after work-up and FSGC (5% CH₃OH in CH₂Cl₂) the title compound was isolated as a colorless film (0.058 g; 90%).

The HCl salt of the title compound was prepared in the usual manner by the reaction of the free base with 1M HCl-Et₂O and processing the precipitate to obtain a beige solid (0.066 g).

Using a similar procedure, the product of step 3 was converted to other compounds, first by alkylation of the piperazine nitrogen with the appropriate halide, followed by deprotection and coupling of the piperidinyl portion with the appropriate acid to form the amides of general structure:

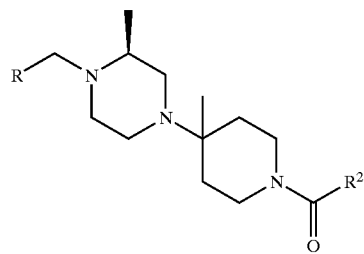

wherein R and R² are as defined in the table:

| Ex. | R | R² | Mp (° C.) | HRMS (MH⁺) |
|---|---|---|---|---|
| 9A | 4-CF₃-phenyl | 3-Cl-2-NH₂-phenyl | 246–249 | 509.2293 |
| 9B | 4-CF₃-phenyl | 2,3-dimethyl-phenyl | 204–208 | 488.2895 |
| 9C | 4-I-phenyl | 2,3-dimethyl-phenyl | 247–249 | 546.1978 |
| 9D | 4-I-phenyl | 3-Cl-2-NH₂-phenyl | 249–251 | 567.1407 |
| 9E | 4-CF₃O-phenyl | 2,3-dimethyl-phenyl | 206–209 | 504.2848 |
| 9F | 4-CF₃O-phenyl | 3-Cl-2-NH₂-phenyl | 244–247 | 525.2242 |
| 9G | 4-CH₃SO₂-phenyl | 2,3-dimethyl-phenyl | 201–204 | 484.2630 |

-continued

| Ex. | R | R² | Mp (° C.) | HRMS (MH⁺) |
|---|---|---|---|---|
| 9H | 4-(methylsulfonyl)phenyl | 3-chloro-2-aminophenyl | 222–226 | 505.2039 |
| 9I | 6-methoxypyridin-3-yl | 2,6-dimethylphenyl | 226–229 | 451.3060 |
| 9J | 6-methoxypyridin-3-yl | 3-chloro-2-aminophenyl | 229–232 | 472.2474 |
| 9K | 6-chloropyridin-3-yl | 2,6-dimethylphenyl | 268–271 | 455.2577 |
| 9L | 6-chloropyridin-3-yl | 3-chloro-2-aminophenyl | 212–216 | 476.1975 |
| 9M | 4-methoxyphenyl | 2,6-dimethylphenyl | 229–232 | 450.3126 |
| 9N | 4-methylphenyl | 2,6-dimethylphenyl | 246–251 | 434.3168 |
| 9O | 4-(trifluoromethyl)phenyl | 3,5-dimethyl-4-(pyridin-3-yl N-oxide)phenyl | 192–205 | — |
| 9P | 4-(trifluoromethoxy)phenyl | 3,5-dimethyl-4-(pyridin-3-yl N-oxide)phenyl | 185–196 | — |

-continued

| Ex. | R | R² | Mp (° C.) | HRMS (MH⁺) |
|---|---|---|---|---|
| 9Q | 4-(F₃CO)phenyl | 3,5-dimethyl-4-hydroxyphenyl | 202–210 | — |
| 9R | 4-(F₃C)phenyl | 3,5-dimethyl-4-hydroxyphenyl | 203–206 | — |
| 9S | 4-(F₃C)phenyl | 4,6-dimethylpyrimidin-5-yl | 190–205 | — |
| 9T | 4-(F₃CO)phenyl | 4,6-dimethylpyrimidin-5-yl | 180–205 | — |
| 9U | 4-(F₃C)phenyl | 2,4,6-trichlorophenyl | 258–262 | — |

Using a similar procedure described below, compounds wherein R is 4-ethoxynaphthyl were also prepared:
Steps 1–3: See Example 9.
Step 4A: 4-Hydroxynaphthaldehyde (0.86 g) and K₂CO₃ (1.38 g, 2 equiv.) in CH₃CN (35 ml) were treated with CH₃CH₂I (0.80 ml, 2 equiv.), and the resulting mixture was stirred at RT for 20 h. The reaction mixture was concentrated in vacuo, the residue treated with EtOAc, and the mixture filtered. The filtrate was partitioned with H₂O. The dried (MgSO₄) EtOAc was concentrated in vacuo to give an orange-brown residue (0.89 g). This residue was placed on preparative thin layer plates (10, 1000μ), and eluted with CH₂Cl₂ to give the title compound (0.82 g).
Step 4: Under argon, the products of step 3 (0.270 g; 0.95 mmol) and step 4A (0.571 g; 2.9 mmol) in CH₂Cl₂ (25 ml) were stirred at RT for 30 min. Na(OAc)₃BH (0.506 g; 3.4 mmol) was added. After 19 h, the reaction mixture was quenched with dilute NaOH. The aqueous layer was washed with CH₂Cl₂ (3×). The combined CH₂Cl₂ solution was washed with H₂O (3×) and then brine. The dried (MgSO₄) CH₂Cl₂ solution was concentrated to ~50 ml. Amberlyst 15 (4.5 meq/g: 2.4 g; 11.025 mmeq) was added. After 19 h, additional Amberlyst 15 (2.3 g) was added. After 7 h, the resin was washed with CH₂Cl₂ (5×), THF (5×), THF:H₂O (5×), H₂O (5×), CH₃OH (5×) and CH₂Cl₂ (5×). The resin was eluted with 2M NH₃ in CH₃OH (300 ml) (3×), followed by concentration in vacuo to give an amber oil (0.215 g). The crude material was placed on preparative thin layer plates (4, 1000μ), and eluted with CH₂Cl₂:2M NH₃ in CH₃OH (9:1) to give an amber oil (0.125 g, 36%).

Step 5: Using the appropriate carboxylic acid in the procedure of Example 9, step 5, the following compounds were prepared:

9V

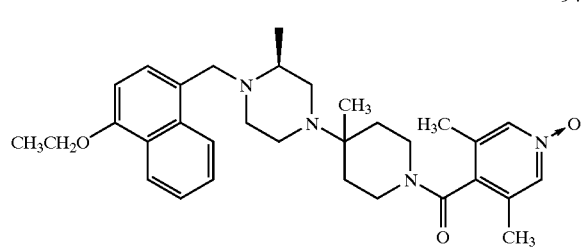

LCMS found M+H=531: HPLC* Retention time 5.52 min.

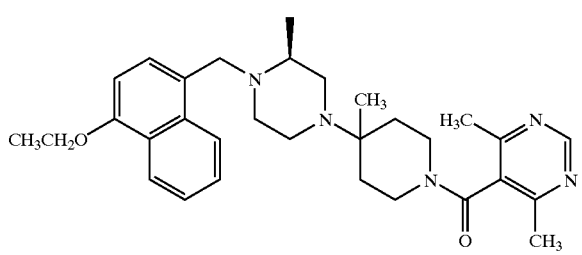

9W

LCMS found M+H=516; HPLC* Retention time 5.66 min. HPLC: VYDAC 218TP5405 column; gradient 5–95% B over 10 min hold 2 min; Soln A 0.1% TFA/H$_2$O, Soln B 0.1% TFA/CH$_2$CN at 245 nm.

Using a similar procedure wherein the starting piperazine does not have the methyl substituent, the following compound was prepared:

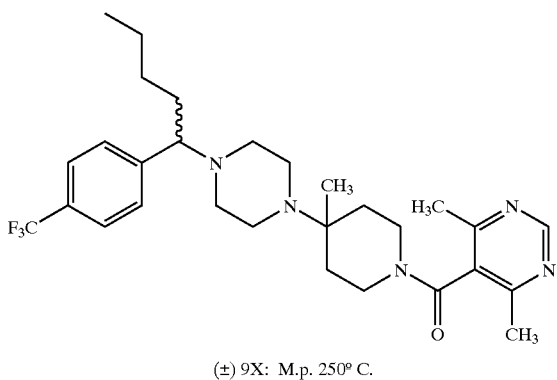

(±) 9X: M.p. 250° C.

EXAMPLE 10

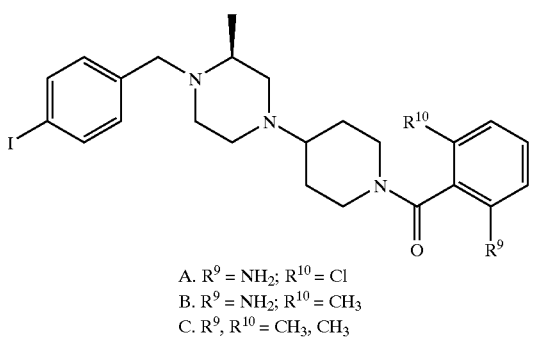

A. R$^9$ = NH$_2$; R$^{10}$ = Cl
B. R$^9$ = NH$_2$; R$^{10}$ = CH$_3$
C. R$^9$, R$^{10}$ = CH$_3$, CH$_3$

Step 1: A solution of 4-N-BOC-2(S)-methyl piperazine (0.4 g; 2 mmol), p-iodobenzaldehyde (0.46 g; 2 mmol) and NaBH(OAc)$_3$ (0.65 g; 3 mmol) in 6 ml of CH$_2$Cl$_2$ was heated at gentle reflux for 14 h. The contents were cooled, diluted with 30 ml of CH$_2$Cl$_2$ and washed with 1 N NaOH solution, water and brine to isolate an yellow oil (0.8 g). FSGC (25% EtOAc-hexane) afforded the desired product (0.66 g; 79%) as a colorless film. TLC R$_f$=0.6 in 25% EtOAc-hexane The BOC protecting group was removed from the product (0.66 g; 1.58 mmol) by treatment with TFA (1 ml) in CH$_2$Cl$_2$ (2 ml). Following standard work up, the mono-alkylated piperazine (0.5 g; 100%) was obtained as a colorless gum.

Step 2: NaBH(OAc)$_3$ (0.63 g; 3 mmol) and two drops of AcOH were added to a solution of the product of step 1 (0.5 g; 1.58 mmol) and N-BOC-piperidinone (0.6 g; 3 mmol) in 5 ml of CH$_2$Cl$_2$ and the resulting solution was stirred at ambient temperature for 16 h. After the usual work up and FSGC, the desired product (0.6 g; 76%) was obtained as a colorless oil. TLC R$_f$=0.4 in 25% acetone-CH$_2$Cl$_2$.

The free piperidine (0.38 g; 79%) was prepared from the N-BOC protected compound (0.6 g; 1.2 mmol) by treatment with TFA (2 ml) in CH$_2$Cl$_2$ (5 ml).

Compound 10A:

The coupling of 6-chloro anthranilic acid (0.065 g; 0.38 mmol) with the product of step 2 (0.127 g; 0.32 mmol) in the presence of DEC (0.092 g; 0.48 mmol), HOBT (0.065 g; 0.48 mmol) and diisopropylethyl amine (0.1 ml), followed by product isolation, were carried out as described previously. This procedure furnished the compound 10A (0.13 g; 73%) as a colorless film. TLC R$_f$=0.5/0.45 for a pair of rotomers in 2% CH$_3$OH—CH$_2$Cl$_2$.

The HCl salt of the title compound was prepared in the usual manner. Mp: 198–202° C.; HRMS (MH$^+$)=553.1231.

Compound 10B:

Coupling the product of step 2 with 6-methyl anthranilic acid gave compound 10B (HCl salt) in 73% yield. Mp: 197–200° C.; HRMS (MH+)=533.1774.

Compound 10C:

2,6-Dimethyl benzoic acid was coupled to the product of step 2 to obtain the amide 10C (HCl salt) in 50% yield. Mp: 202–205° C.; HRMS (MH$^+$)=532.1826.

EXAMPLE 11

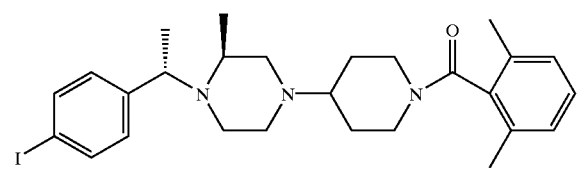

Step 1: (S)-Methylbenzylamine (27 ml, 0.2 mol) in CH$_2$Cl$_2$ (50 ml) was dropped into ice-cold trifluoroacetic anhydride (40 ml) in CH$_2$Cl$_2$ (200 ml) within 15 min. The mixture was stirred at RT for 1 h, then cooled in an ice water bath, iodine was added (27 g, 0.106 mol) and then [bis(trifluoroacetoxy)iodo]-benzene (25 g, 0.058 mol). After being stirred at RT overnight in the dark, more [bis(trifluoroacetoxy)iodo]benzene (24 g, 0.056 mol) was added and the mixture was stirred at RT for one more day. The mixture was diluted with CH$_2$Cl$_2$ (500 ml) and ice-cold Na$_2$SO$_3$ (10% aqueous, 500 ml) and stirred for 0.5 h. The organic layer was separated and washed with NaHCO$_3$, filtered through a short silica gel column and washed with CH$_2$Cl$_2$ (500 ml). After CH$_2$Cl$_2$ was evaporated, Et$_2$O (125 ml) was added and the mixture stirred for 10 min. Hexanes (600 ml) was added gradually to the Et$_2$O solution and the mixture was stirred for 0.5 h. The precipitate was collected and washed with hexanes. The white solid was dried at RT and iodo compound (36.5 g, 53% yield, R$_f$=0.7, EtOAc/hexanes, 1:3) was obtained.

Step 2: The product of step 1 (11.2 g, 0.033 mol) was dissolved in CH$_3$OH (200 ml) and NaOH (15 g, 0.375 mol) in water (100 ml) was added dropwise. The mixture was stirred at RT for 2.5 h. After the CH$_3$OH was evaporated, the aqueous layer was extracted with Et$_2$O (3×100 ml) and the combined organic portion was washed with brine, dried over Na$_2$SO$_4$, filtered and concentrated to give a free amine.

Methyl-R-lactate (4.08 g, 0.039 mol) was dissolved in CH$_2$Cl$_2$ (40 ml) and the mixture was stirred and cooled in acetone-CO$_2$ to −78° C. under N$_2$ atmosphere. Trifluoromethane sulfonic anhydride (10.2 g, 0.036 mmol) and then 2,6-lutidine (6.27 g, 0.059 mol) were added and the mixture was stirred for 5 min at −78° C. The mixture was warmed to RT and stirred for 30 min. More CH$_2$Cl$_2$ was added to the mixture and the solution was washed with 2N HCl. The freshly prepared amine from above was added to the triflate solution followed by K$_2$CO$_3$ (18 g, 0.132 mol) in water (20 ml). The mixture was stirred at RT overnight. Extractive work-up with CH$_2$Cl$_2$ followed by silica gel column chromatography gave a secondary amine (8.27 g, 75% yield, R$_f$=0.65, hexanes/EtOAc, 3:1) as a yellow syrup.

Step 3: The amine of step 2 (17.3 g, 0.052 mol) was dissolved in dichloroethane (100 ml) and ClCH$_2$COCl (117.2 g, 82 ml, 1.04 mol). The mixture was stirred under reflux condition for 3 h. Both the solvent and ClCH$_2$COCl were removed under vacuum. The remaining yellow syrup was dissolved in DMSO (40 ml) at 0° C. and NaI (5.2 g, 0.035 mol) and NH$_4$OH (56 ml, 1.04 mol) were added. The reaction mixture was stirred 0° C. for 30 min., warmed up to RT and stirred overnight. Water (100 ml) was added to the mixture and the precipitate was filtered and washed with water. The white solid obtained was dried in air to give the diketopiperazine (14.3 g, 77% yield, R$_f$=0.56, hexanes/EtOAc, 3:1).

Step 4: The diketopiperazine of step 3 (14.3 g, 0.04 mol) was dissolved in dimethoxy ethane (200 ml) and NaBH$_4$ (15.1 g, 0.4 mol) and BF$_3$.OEt$_2$ (34 g, 29.5 ml, 0.24 mol) were added to the solution. The mixture was stirred under reflux conditions for 3 h and then cooled to about 0° C. on a ice bath. CH$_3$OH (500 ml) and then concentrated HCl (300 ml) were added slowly to the mixture. The solution was stirred for 20 min. at RT and then under reflux conditions for 45 min. The mixture was concentrated and NaOH was added until the pH was more than 10. Extractive work up with EtOAc gave the desired piperazine as a yellow syrup (12.9 g, 98% yield).

Step 5: The product of step 4 (1.9 g, 5.79 mmol), N-BOC-4-piperidone (5.73 g, 28.8 mmol), NaBH(OAc)$_3$ (6.1 g, 28.8 mmol) and 2M AcOH (5.76 ml, 11.52 mmol) were combined in CH$_2$Cl$_2$ (150 ml) and the mixture was stirred overnight. After the solvent was removed, NaOH (3N) was added and extractive work up with EtOAc followed by silica gel chromatography afforded pure piperazino-piperidine (2.21 g, 75% yield, R$_f$=0.18, hexanes/EtOAc, 1:1) as a syrup.

Step 6: The product of step 5 (1.9 g, 3.7 mmol) was dissolved in CH$_2$Cl$_2$ (10 ml) and TFA (10 ml) was added. The mixture was stirred at RT for 2 h. After the removal of the solvent and TFA under reduced pressure, NaOH solution (3N) was added to the remaining syrup and extractive work up with EtOAc gave the free piperazino-piperidine (1.3 g, 85% yield) as a yellow syrup. To a solution of the free piperazino-piperidine (200 mg, 0.484 mmol) in CH$_2$Cl$_2$ (2 ml) were added 2,6-dimethylbenzoic acid (150 mg, 0.99 mmol), DEC (191 mg, 0.99 mmol) and HOBT (135 mg, 0.99 mmol). The mixture was stirred at RT overnight and then the solvent was removed under reduced pressure. NaOH solution (3N) was added to the remaining syrup and extractive work up with EtOAc followed by column chromatography afforded the title compound (210 mg, 80% yield, R$_f$=0.37, CH$_2$Cl$_2$/CH$_3$OH, 20:1). HRMS (as the HCl) calcd for C$_{27}$H$_{37}$N$_3$OI (M+H$^+$) 546.1981, found 546.1965. Mp: 190° C. (dec.).

Using a similar procedure, compounds of the formula

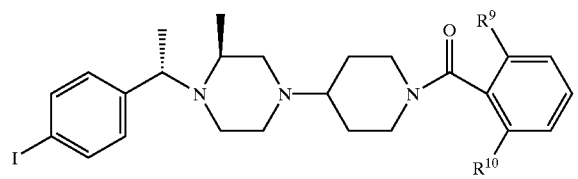

were prepared, wherein R$^9$ and R$^{10}$ are as defined in the table:

| Ex | R$^9$ | R$^{10}$ | Mp (° C.) | HRMS |
| --- | --- | --- | --- | --- |
| 11A | —CH$_3$ | —NH$_2$ | 198 (dec.) | 547.1928 |
| 11B | —Cl | —NH$_2$ | 203 (dec.) | 567.1395 |
| 11C | —OH | —OH | 200 (dec.) | 550.1555 |
| 11D | —OCH$_3$ | —OCH$_3$ | 200 (dec.) | 578.1860 |

EXAMPLE 12

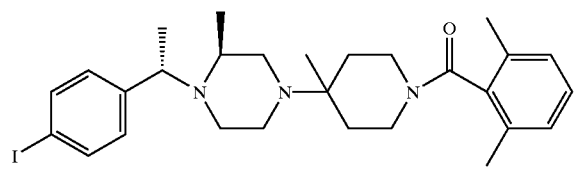

Step 1: To the solution of the product of Example 11, step 4 (1.4 g, 4.2 mmol) and 1-tert-butoxycarbonyl-4-piperidone (0.93 g, 4.67 mmol) in CH$_2$Cl$_2$ was added Ti(OiPr)$_4$ (1.19 g, 4.2 mmol) and the mixture was stirred at RT overnight. 1M Et$_2$AlCN (5.04 ml, 5.04 mmol) was added, the mixture was stirred overnight at RT and the solvent was evaporated. Saturated NaHCO$_3$ was added to the residue and extractive work up with EtOAc gave the Strecker amine as a yellow syrup. The syrup was dissolved in THF (40 ml) and 3M CH$_3$MgBr (7 ml, 21 mmol) was added to the solution. The mixture was stirred at RT overnight, then cooled to 0° C. and saturated NH$_4$Cl and water was added. Extractive work up with EtOAc followed by silica gel chromatography gave the piperazino-piperidine product (1.78 g, 81% yield, R$_f$=0.52, hexanes/EtOAc, 2:1).

Step 2: Treat the product of step 1 in the manner described in Example 11, Step 6, to obtain the title compound. Mp. 190° C. (dec.); HRMS (as the HCl salt): found 560.2145.

Using a similar procedure, compounds of the formula

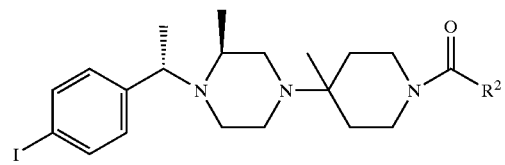

were prepared, wherein $R^2$ is defined in the table:

| Ex | $R^2$ | mp (° C.) | HRMS |
|---|---|---|---|
| 12A | H$_2$N— / —Cl (phenyl) | 145 (dec.) | 581.1537 |
| 12B | H$_2$N— / —CH$_3$ (phenyl) | 150 (dec.) | 561.2083 |
| 12C | H$_3$C— / —CH$_3$ (pyridyl) | 208 (dec.) | 561.2096 |
| 12D | HO— / —CH$_3$ (phenyl) | 206 (dec.) | 562.1944 |
| 12E | H$_3$C— / —CH$_3$ (pyridyl N-oxide) | 190 (dec.) | 577.2029 |
| 12F | Cl— / —Cl (pyridyl) | 245 (dec.) | 601.1006 |
| 12G | H$_3$C— / —CH$_3$ (2-OH pyridyl) | 218 (dec.) | 577.2029 |
| 12H | Cl— / —Cl (pyridyl N-oxide) | 195 (dec.) | 617.0945 |
| 12I | H$_3$C— / —CH$_3$ (pyrimidyl) | 116 (dec.) | 562.2048 |

EXAMPLE 13

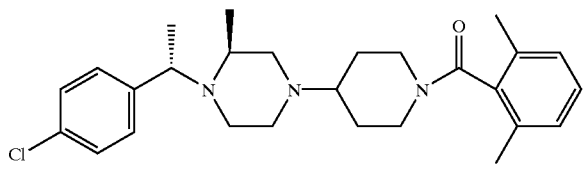

Step 1: To a solution of the N-BOC protected product of Example 11, step 4 (250 mg, 0.581 mmol) in DMF (2.5 ml), CuCl (1 g, 10.1 mmol) was added. The suspension was stirred under N$_2$ at 110° C. for 24 h. After the mixture was cooled to RT, NH$_4$OH was added and the solution gradually turned bright blue. Extractive work up with EtOAc gave a mixture of the chloro-substituted piperazine and its BOC derivative. After treating the mixture with TFA (5 ml) in CH$_2$Cl$_2$ (2 ml) for 2 h, the solvent was evaporated and NaOH (3N) was added. Extractive work up with EtOAc afforded the pure piperazine (110 mg, 79%) as a yellow syrup.

Step 2: The product of step 1 was treated in a manner similar to Example 11, steps 5 and 6, to obtain the title compound. Mp. 180° C. (dec.); HRMS (as the HCl salt): found 454.2617.

Using a similar procedure, compounds of the formula:

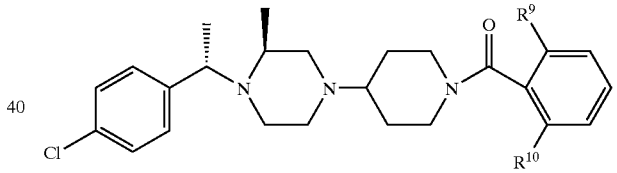

were prepared wherein $R^9$ and $R^{10}$ are defined in the table:

| Ex | $R^9$ | $R^{10}$ | Mp (° C.) | HRMS |
|---|---|---|---|---|
| 13A | —CH$_3$ | —NH$_2$ | 200 (dec.) | 455.2577 |
| 13B | —Cl | —NH$_2$ | 200 (dec.) | 475.2023 |
| 13C | —Cl | —Cl | 187 (dec.) | 494.1536 |

Using the product of step 1 in the procedure of Example 12, compounds of the formula:

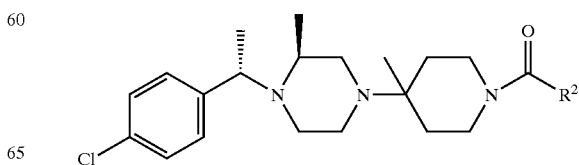

were prepared, wherein R² are defined in the table:

| Ex | R² | Mp (° C.) | HRMS |
|---|---|---|---|
| 13D | 2,6-dimethylphenyl | 197 (dec.) | 468.2779 |
| 13E | 2-amino-6-chlorophenyl | 205 (dec.) | 489.2184 |
| 13F | 2-amino-6-methylphenyl | 210 (dec.) | 469.2734 |
| 13G | 4,6-dimethylpyrimidinyl | 195 (dec.) | 470.2689 |
| 13H | 3,5-dichloropyridinyl | 260 (dec.) | 509.1634 |
| 13I | 2,4-dimethylpyridine N-oxide | 200 (dec.) | 485.2688 |

EXAMPLE 14

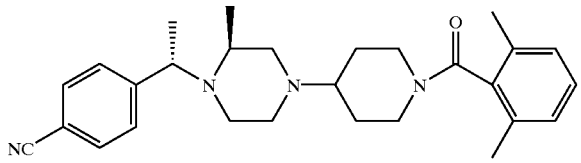

Step 1: To a solution of the N-BOC protected product of Example 11, step 4 (5 g, 0.012 mol) in DMF (20 ml), CuCN (20.8 g, 0.23 mol) was added. The suspension was stirred under N₂ at 110° C. for 22 h. After the mixture was cooled to RT, NH₄OH was added and the solution gradually turned bright blue. Extractive work up with EtOAc followed by silica gel column chromatography gave the cyano derivative (2.29 g, 60% yield, R$_f$=0.5, hexanes/EtOAc, 4:1), the carboxamide derivative (0.95 g, 23.6% yield, R$_f$=0.2, CH₂Cl₂/CH₃OH, 10:1) and the unsubstituted derivative (85 mg, 2.4% yield, R$_f$=0.75, hexanes/EtOAc, 2:1).
Step 2: The BOC group on the cyano compound of step 1 was first removed under acidic conditions and the resultant amine was converted to the title compound following the procedure of Example 11, steps 5 and 6. HRMS (as the HCl salt): found 445.4970.

EXAMPLE 15

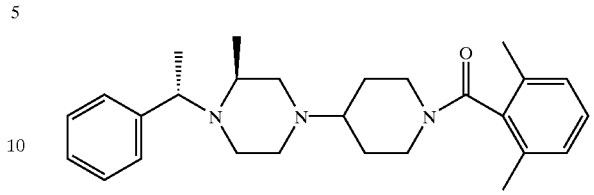

Step 1: To a solution of the N-BOC protected product of Example 11, step 4 (1.4 g, 3.26 mmol) and CuCl (1.61 g, 16.3 mmol) in CH₃OH at 0° C. was added NaBH₄ (3.69 g, 97.6 mmol) slowly. A black precipitate was formed. The mixture was warmed to RT and stirred overnight. The precipitate was removed by celite filtration and CH₃OH was removed under vacuum. Extractive work up with EtOAc afforded the desired compound (1 g, 100% yield, R$_f$=0.55, hexanes/EtOAc, 5:1) as a syrup.
Step 2: The BOC group on the product of step 1 was removed under acidic conditions and the resultant amine was converted to the title compound following the procedure of Example 11, steps 5 and 6. Mp. 195° C.; HRMS (as the HCl salt): found 420.3016.

Using a similar procedure, the following compound is prepared:

15A

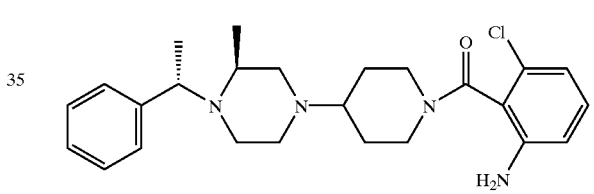

HRMS (as the HCl salt): found 441.2426

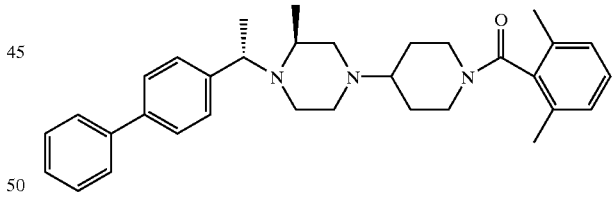

EXAMPLE 16

Step 1: To a solution of the N-BOC protected product of Example 11, step 4 (2.5 g, 5.8 mmol) in benzene were added phenyl boric acid (1.68 g, 13.8 mmol), 2M Na₂CO₃ (14 ml) and tetrakis(tri-phenyl phosphine) palladium (0.67 g, 0.58 mmol). The mixture was stirred under reflux overnight. Extractive work up with EtOAc followed by silica gel column chromatography gave the phenyl derivative (1.37 g, 62% yield, R$_f$=0.5, hexane/EtOAc, 5:1) as a syrup.
Step 2: The BOC group on the product of step 1 was removed under acidic conditions and the resultant amine was converted to the title compound following the procedure of Example 11, steps 5 and 6. Mp. 190° C.; HRMS (as the HCl salt): found 496.3319.

Using a similar procedure, compounds of the formula:

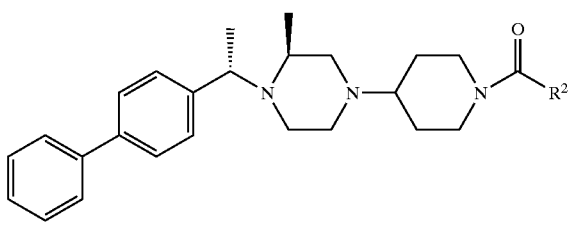

were prepared, wherein R² are defined in the table:

| Sch | Ex | R² | Mp (° C.) | HRMS |
|---|---|---|---|---|
| 223254 | 16A | 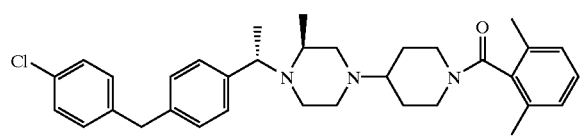 (H₂N, Cl) | 190 (dec.) | 517.2754 |
| 223255 | 16B | (H₂N, CH₃) | 65–70* | 497.3287 |
| 2?5666 | 16C | (H₃C, CH₃, pyrimidine) | 190 (dec.) | 498.3225 |

*free base

EXAMPLE 17

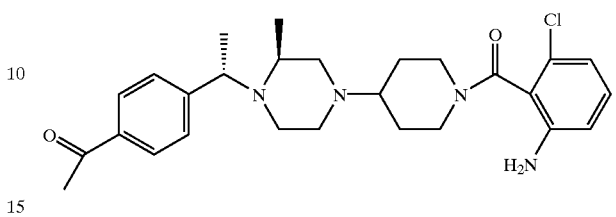

Step 1: The N-BOC protected product of Example 11, step 4 (800 mg, 1.88 mmol) was dissolved in dry THF and the temperature was brought to −780 C. under N₂. Butyl lithium (2.5 M solution, 0.832 ml, 2 mmol) was added and the mixture was stirred at −78° C. for 10 min. The solution then was dropped into p-chlorobenzyl aldehyde (234 mg, 2.07 mmol) in THF at −78° C. The mixture was stirred for 30 min. at −78° C., then gradually warmed up to RT. Saturated NH₄Cl was added to the mixture and extractive work up with EtOAc followed by silica gel column chromatography gave the desired alcohol (30 mg, 3.6% yield, $R_f$=0.5, hexanes/EtOAc, 2:1) as a yellow syrup.

Step 2: A solution of alcohol of step 1 (40 mg, 0.090 mmol), triethylsilane (52 mg, 0.45 mmol) and TFA (5 ml) in CH₂Cl₂ (5 ml) was stirred under reflux conditions for 2 h. After CH₂Cl₂, triethylsilane and TFA were removed under reduced pressure, NaOH solution (3N) was added to the remaining syrup. Extractive work up with EtOAc afforded the chlorobenzyl derivative (20 mg, 68% yield) as a yellow syrup.

Step 3: The product of step 2 was converted to the title compound following the procedure of Example 11, steps 5 and 6. Mp. 170° C. (dec.); HRMS (as the HCl salt): found 544.3101.

EXAMPLE 18

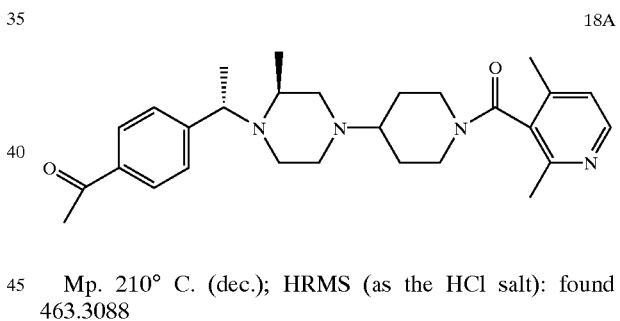

Step 1: To a solution of the N-BOC protected 4-piperidinyl derivative of the cyano compound of Example 14, step 1 (510 mg, 1.24 mmol) in Et₂O (4 ml) was added 3M CH₃MgBr (4 ml) in a dropwise manner. The mixture was stirred under reflux overnight. After the solution was cooled on ice-bath, 12N HCl (4 ml) was added and the mixture was stirred on a steam bath for 2 h. The solution was cooled to RT and solid NaOH pellets were added until the pH was more than 10. Extractive work up with EtOAc/CH₃OH (3:1) afforded the desired methyl ketone (249 mg, 61% yield) as a syrup.

Step 2: The product of step 1 was treated according to the standard DEC peptide coupling procedures of Example 11, step 6, to obtain the title compound. Mp. 210° C.; HRMS (as the HCl salt): found 483.2522.

Using a similar procedure, the following compound is prepared:

18A

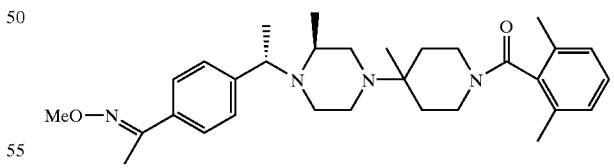

Mp. 210° C. (dec.); HRMS (as the HCl salt): found 463.3088

EXAMPLE 19

Step 1: To a solution of the product of Example 22 (140 mg, 0.29 mmol) in CH₃OH (10 ml) and EtOH (1 ml) were added NH₂OCH₃.HCl (738 mg, 8.84 mmol) and NaOAc (725 mg, 8.84 mmol). The suspension was stirred at 40° C. overnight, the solvents were evaporated and water was added to the residue. Extractive work up with EtOAc followed by silica gel chromatography generated the title compound (99 mg, 68% yield, $R_f$=0.38, CH₂Cl₂/CH₃OH, 20:1). HRMS (as the tartrate) calc'd. for $C_{31}H_{45}N_4O_2$ (M+H⁺) 505.3543; found 505.3542.

Using a similar procedure, compounds of the formula

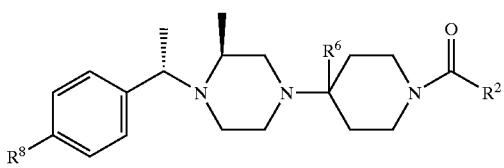

were prepared, wherein $R^8$, $R^6$ and $R^2$ are defined in the table:

of 0.15 g (~0.14 mmol) of resin bound cardodiimide (prepared by reacting Argopore-Cl resin with 1-(3-dimethylaminopropyl)3-ethyl carbodiimide in DMF at 100° C. in DMF (1.5 ml) in a polyethylene SPE cartridge. To this mixture add 75 μl of a 1 M solution of 5-methyl-3-phenylisoxazole-4-carboxylic acid in DMF (0.075 mmol), and HOBT (24 ul of a 1M solution in DMF). Shake this mixture for 14 h, filter and add 0.1 g of Amberlyst-15 resin (0.47 mmol) to the filtrate. Shake for 1 to 2 h, filter and wash the resin twice with each of the following solvents THF, $CH_2Cl_2$ and $CH_3OH$, then wash with THF and $CH_2Cl_2$. Treat the resin with 2M $NH_3$ in $CH_3OH$ (1 time for 30 min,

| Ex. | $R^8$ | $R^6$ | $R^2$ | mp (° C.) | HRMS |
|-----|-------|-------|-------|-----------|------|
| 19A | $H_3C-C(=NOCH_3)-$ | H | 2-amino-6-chlorophenyl | 194 (dec.) | 512.2785 |
| 19B | $H_3C-C(=NOCH_3)-$ | H | 2,4-dimethylpyridin-3-yl | 150 (dec.) | 492.3344 |
| 19C | $H_3C-C(=NOCH_2CH_3)-$ | H | 2,4-dimethylpyridin-3-yl | — | 506.3494 |
| 19D | $H_3C-C(=NOH)-$ | —$CH_3$ | 2,4-dimethylpyridin-3-yl N-oxide | 180 (dec.) | 508.3296 |
| 19E | $H_3C-C(=NOH)-$ | —$CH_3$ | 4,6-dimethylpyrimidin-5-yl | 195 (dec.) | 493.3291 |

EXAMPLE 20

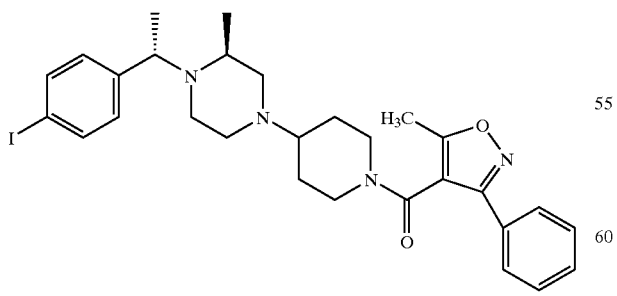

Dissolve the free piperazino-piperidine of Example 11, step 6 (1.7 g, 3.3 mmol) in $CHCl_3$ (30 ml:=Stock solution A). Add 250 μl of stock solution A (0.027 mmol) to a slurry and 1 time for 5 min). Combine and concentrate the filtrates under reduced pressure to afford the title compound. LCMS found $MH^+$=599.1 (calculated MW 598); TLC $R_f$=0.74 ($CH_2Cl_2$/$CH_3OH$/$NH_4OH$ (95/5/0.5)).

Using the procedure above with the appropriate carboxylic acids gave the following compounds:

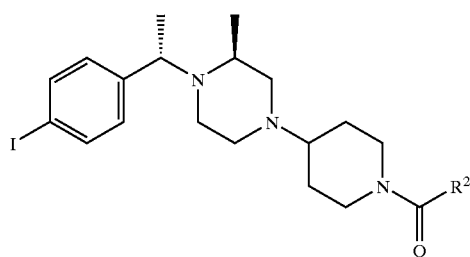

were prepared, wherein R² are defined in the table:

| Ex. | R² | LCMS results | TLC R$_f$ values |
|---|---|---|---|
| 20A | (2-F, 6-I phenyl) | MH⁺ = 600.1<br>R$_t$ = 6.56 min. | 0.92 |
| 20B | (2,6-dichloro-3-amino phenyl) | MH⁺ = 601.1<br>R$_t$ = 5.69 min. | 0.63 |
| 20C | (2,4,6-trimethyl phenyl) | MH⁺ = 560.1<br>R$_t$ = 5.77 min. | 0.60 |
| 20D | (2,2-dimethyl indan) | MH⁺ = 588.1<br>R$_t$ = 6.61 min. | 0.66 |
| 20E | (2-CF₃, 6-F phenyl) | MH⁺ = 604.1<br>R$_t$ = 5.60 min. | 0.87 |
| 20F | (2-Br, 3-OMe, 6-OMe phenyl) | MH⁺ = 658.2<br>R$_t$ = 5.69 min. | 0.86 |
| 20G | (fluorenyl) | MH⁺ = 606.1<br>R$_t$ = 6.17 min. | 0.43 |
| 20H | (naphthyl) | MH⁺ = 568.1<br>R$_t$ = 5.67 min. | 0.57 |
| 20I | (1-phenylcyclopentyl) | MH⁺ = 586.1<br>R$_t$ = 6.02 min. | 0.63 |
| 20J | (1-phenylcyclopropyl) | MH⁺ = 558.1<br>R$_t$ = 5.35 min. | 0.33 |
| 20K | (1-phenylethyl) | MH⁺ = 546.1<br>R$_t$ = 5.37 min. | 0.52 |

EXAMPLE 21

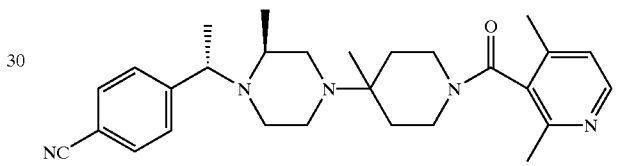

Step 1: The BOC group on the cyano compound of Example 14, step 1, was first removed under acidic conditions and the resulting amine (1.59 g. 6.96 mmol), 1-tert-butoxycarbonyl-4-piperidone (1.66 g, 8.35 mmol) and Ti(OiPr)$_4$ (2.18 g, 7.66 mmol) in CH$_2$Cl$_2$ were stirred at RT overnight. 1M Et$_2$AlCN (8.35 ml, 8.35 mmol) was added, the mixture was stirred overnight at RT and the solvent was evaporated. Saturated NaHCO$_3$ was added to the residue and extractive work up with EtOAc followed by column chromatography gave the Strecker amine as a yellow syrup (1.76 g, 58% yield, R$_f$=0.70, Hexanes/EtOAc, 2:1).

Step 2: The amine of Step 1 (200 mg, 0.46 mmol) was dissolved in anhydrous THF (2 ml) and 3M CH$_3$MgBr (0.76 ml, 2.29 mmol) was added dropwise. The mixture was stirred at RT overnight and then cooled to 0° C. Saturated NH$_4$Cl (10 ml) was added and a precipitate appeared. Water (40 ml) was addded and the precipitate disappeared. Extractive work up with EtOAc followed by column chromatography gave the desired ipso-methyl derivative (169 mg, 86% yield, R$_f$=0.53, Hexanes/EtOAc, 2:1).

Step 3: The product of step 2 was treated in the manner described in Example 11, Step 6, to obtain the title compound. Dec. 198° C.; HRMS (as the HCl salt): found 460.3079.

Using a similar procedure, compounds of the formula:

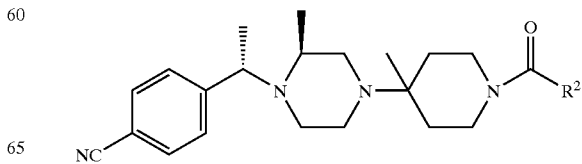

were prepared, wherein $R^2$ are defined in the table:

| Ex | $R^2$ | Mp (° C.) | HRMS |
|---|---|---|---|
| 21A | H_2N—C_6H_3—Cl (2-amino-6-chlorophenyl) | 205 (dec.) | 480.2532 |
| 21B | 2,4-dimethylpyridine N-oxide-3-yl | 65–75* | 476.3033 |
| 21C | 3,5-dichloropyridin-4-yl | 250 (dec.) | 500.1992 |
| 21D | 4,6-dimethylpyrimidin-5-yl | 195 (dec.) | 461.3019 |

*Mp for the free amine

EXAMPLE 22

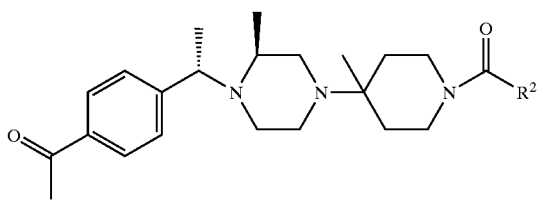

Step 1: The Strecker amine from Example 21, step 1 (380 mg, 0.87 mmol) was treated with CH$_3$MgBr (2.9 ml, 8.7 mmol) in Et$_2$O (5 ml) under reflux conditions overnight. The mixture was cooled on ice and water (5 ml) was added dropwise. 12N HCl (6 ml) was added and the mixture was stirred on a steam bath for 2 h. After the mixture was cooled on ice, NaOH was added until the pH of the solution was above 10. Extractive work up with EtOAc afforded a free amine as a syrup (307 mg, 100% yield).

Step 2: The product of step 1 was converted to the title compound following the peptide coupling procedure described in Example 1 1, step 6.

Mp. 80–85° C.; HRMS found 476.3271.

Using a similar procedure, compounds of the formula

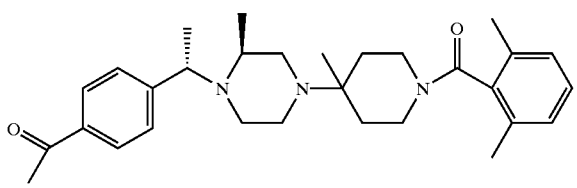

were prepared, wherein $R^2$ are defined in the table:

| Ex. | $R^2$ | Mp (° C.) | HRMS |
|---|---|---|---|
| 22A | 2,4-dimethylpyridine N-oxide-3-yl | 195 (dec.) | 493.3172 |
| 22B | 4,6-dimethylpyrimidin-5-yl | 200 (dec.) | 478.3178 |

EXAMPLE 23

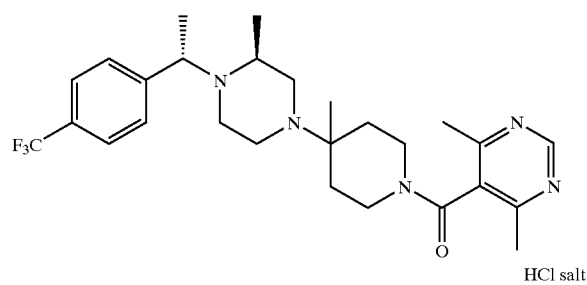

HCl salt

Steps 1–3:

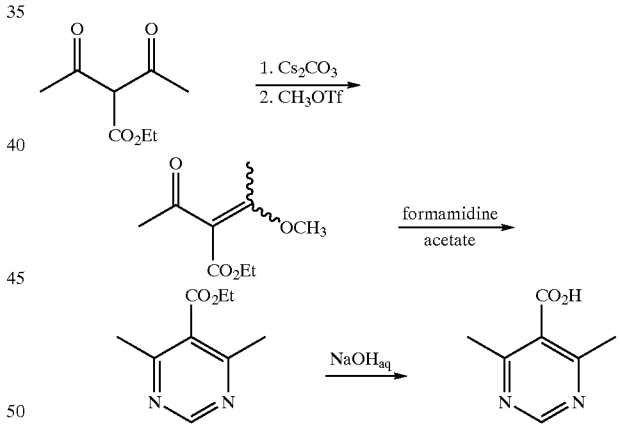

Step 1: Ethyl diacetoacetate (93.4 g), CS$_2$CO$_3$ (185 g) and CH$_3$CN (550 ml) were mixed together, using an overhead mechanical stirrer. CH$_3$CN (50 ml) was added and the resulting mixture was cooled to 0° C. Methyl trifluoromethane sulfonate (88.6 g) was added dropwise and after addition, the cooling bath was removed. The mixture was stirred for 1 h at RT, filtered, and the salts were washed with Et$_2$O (2×50 ml). The organic extracts were combined and Et$_2$O (300 ml) was added. The resulting mixture was filtered, the filter cake was washed with Et$_2$O (2×100 ml), the Et$_2$O extracts were combined and evaporated to half volume. The solution was cooled in an ice bath and washed once with cooled (0° C.) 2 N NaOH (pH=11). The Et$_2$O layer was dried over MgSO$_4$, filtered and evaporated to give the desired product as a yellow liquid (64.7 g) in 65% yield, which was used directly in the next step.

Step 2: The product of step 1 (64.2 g), sodium ethoxide in ethanol (commercial solution; 21 wt %; 113 g) ethanol (587 ml) and formamidine acetate (36.2 g) were mixed together at RT. After refluxing for 4 h, the mixture was cooled to RT, the resulting precipitate was filtered off and the ethanol was removed under vacuum. The resulting liquid was partitioned between water and $CH_2Cl_2$ and the aqueous layer was extracted with $CH_2Cl_2$ (3×150 ml). The $CH_2Cl_2$ extracts were dried over $MgSO_4$, filtered and evaporated to give a dark crude liquid (50.7 g) which was purified by silica gel chromatography (980 g; 4:1 hexanes:EtOAc as eluant). After evaporation of the appropriate fractions, the desired product (28.5 g) was isolated in 46% yield and used directly in the next step.

Step 3: The product of step 2 (28.1 g), NaOH (6.72 g), water (65 ml) and EtOH (130 ml) were mixed together at RT and heated at reflux for 1 h. The resulting solution was cooled to RT and the volatile materials were removed in vacuo until a thick paste resulted. Water (20 ml) was added, the mixture was cooled to 0° C. and conc. HCl (14.3 ml) was added dropwise with stirring. The resulting white precipitate was collected by filtration, washed with ice water (2×10 ml) and air dried with suction for 30 min. The resulting white solid was treated with toluene (2×20 ml), the solvent was removed in vacuo at 50° C. and dried under vacuum (1 mm Hg) for 18 h. The desired product (14.9 g) was isolated as a white solid in 63% yield, mp: 176–178° C. Elemental analysis of $C_7H_8N_2O_2$: calc'd C 55.26%, H 5.30%, N 18.41%; found: C 55.13%, H 5.44%, N 18.18%.

A second crop of product was isolated by evaporation of the aqueous filtrate (from above) to dryness and addition of water (20 ml). The resulting mixture was stirred at RT for 5 min, cooled in an ice bath and the precipitate formed was collected by filtration. The resulting solid was washed with ice water (2×5 ml) and dried as described above to give the product (4.68 g) as a cream colored solid to give a combined yield of 83%.

Step 4: The product of Example 4, step 6 (trihydrochloride form; 5.4 g), DMF (11.3 ml), HOBt (3.07 g), diisopropyl ethyl amine (12.3 ml) and the product of step 3 (3.45 g) were mixed together and DEC (4.35 g) was added in portions over 15 min. The resulting mixture was heated at 45° C. for 18 h, cooled to RT, diluted with EtOAc (80 ml) and washed with 2 N NaOH (25 ml). The aqueous layer was extracted with EtOAc (3×25 ml), the organic extracts were combined, washed with brine, dried over $Na_2SO_4$, filtered and evaporated. The resulting crude oil was purified by silica gel chromatography (170 g; 76:19:5 hexanes:EtOAc:$Et_3N$ as eluant). After evaporation of the appropriate fractions, the free base form of the title compound (5.21 g) was isolated as a light colored foam in 91% yield.

Step 5: To a cooled (0° C.) solution of the free base of step 4 (2.00 g) and EtOAc (20 ml) was added HCl (3.0 ml of a 4.0 M solution in 1,4-dioxane). The resulting mixture was warmed to RT, diluted with $Et_2O$ (20 ml), filtered, washed with $Et_2O$ (2×20 ml), air dried with suction for 10 min and then under vacuum (1 mm Hg) at 90° C. for 5 h to give the title compound (2.30 g) as a white solid in 97% yield. mp: 159–162° C.

Elemental analysis of $C_{27}H_{36}N_5OF_3 \cdot 2HCl \cdot 0.5H_2O$: calc'd: C 55.38%, H 6.71%, N 11.96%, Cl 12.11%; found: C 55.19%, H 6.69%, N 11.75%, Cl 11.45%.

Additional pyrimidine derivative-compounds were made using similar procedures:

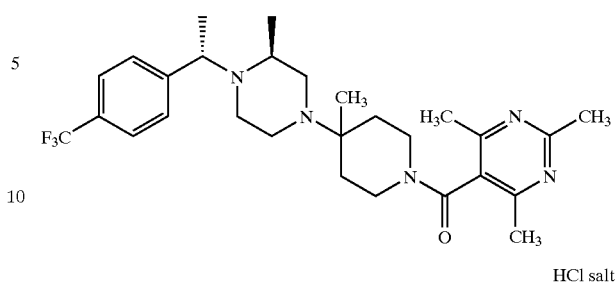

23A

HCl salt

Steps 1–2:

Step 1: The product of Example 23, step 1 was treated in the same manner as in Example 23, step 2, substituting acetamidine hydrochloride (2.03 g) for formamidine acetate. The amounts of the reagents were: product of Example 23, step 1 (4.0 g), ethanol (20 ml) and sodium ethoxide in ethanol (commercial solution; 21 wt %; 8.03 g). After extraction and purification as described above, the product was isolated (1.7 g) as a colorless liquid in 41% yield, which was used directly in the next step.

Step 2: The product of step 1 (1.7 g) was treated in the same manner as Example 23, step 3, using ethanol (5 ml), water (5 ml) and NaOH (1.0 g). After extraction and purification as described above, the product was isolated (0.12 g) as a white solid in 8% yield, which was used directly in the next step.

Step 3: The product of Example 4, step 6 (0.05 g), and the product of step 2 (immediately above) (0.028 g) were subjected to the same reaction conditions as in Example 23, step 4, using HOBt (20 mg), DEC (45 mg), diisopropyl ethylamine (40 mg) and DMF (1.5 ml). After extraction and purification as described above, the product was converted to its HCl salt using the procedure outlined for Example 23, step 5 to give the title compound (77 mg) as a white solid in 97% yield over the two steps. mp: 185–190° C.

23B

HCl salt

Steps 1–2:

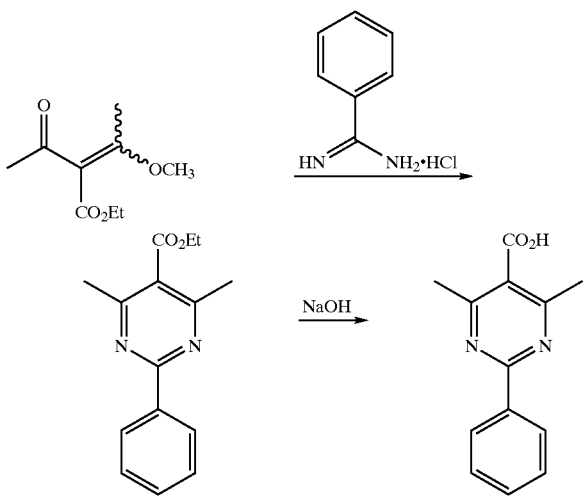

Step 1: The product of Example 23, step 1 was treated in the same as in Example 23, step 2, substituting benzamidine hydrochloride (3.35 g) for formamidine acetate. The amounts of the reagents were: product of Example 23, step 1 (4.0 g), ethanol (20 ml) and sodium ethoxide in ethanol (commercial solution; 21 wt %; 8.03 g). After extraction and purification as described above, the product was isolated (4.5 g) as a liquid in 82% yield which was used directly in the next step.

Step 2: The product of step 1 (4.5 g) was treated in the same manner as Example 23, step 3, using ethanol (10 ml), water (10 ml) and NaOH (2.0 g). After extraction and purification as described above, the product was isolated (3.0 g) as a white solid in 77% yield which was used directly in the next step.

Step 3: The product of Example 4, step 6 (75 mg), and the product of step 2 (immediately above) (39 mg) were subjected to the same reaction conditions as in Example 23, step 4, using HOBt (35 mg), DEC (53 mg), diisopropyl ethylamine (100 mg) and DMF (2 ml). After extraction and purification as described above, the product was converted to its HCl salt using the procedure outlined for Example 23, step 5 to give the title compound (98 mg) as a white solid in 96% yield over the two steps. mp:250–253° C.

23C

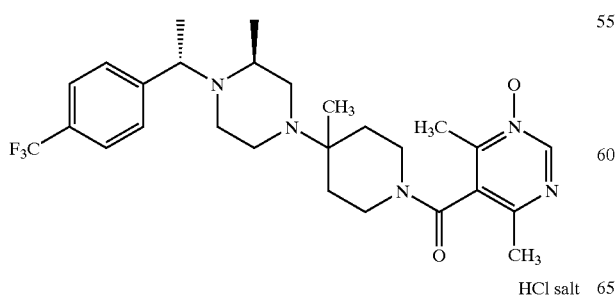

HCl salt

Steps 1–2:

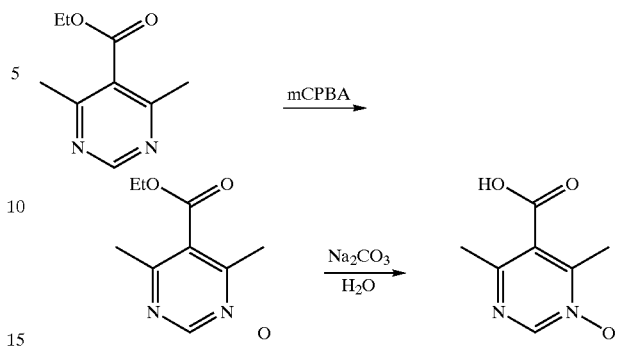

Step 1: The product of Example 23, step 2 (528 mg) was dissolved in $CH_2Cl_2$ (5.0 ml) and meta-chloroperbenzoic acid (mCPBA) (600 mg) was added in three portions at RT. The resulting mixture was stirred at RT for 24 h and $CH_2Cl_2$ (2 ml) and mCPBA (200 mg) were added. After 3 h, the mixture was poured onto a silica gel column (40 g) and eluted with 1:1 hexanes:EtOAc and then 10:1 $CH_2Cl_2$:$CH_3OH$. After evaporation of the appropriate fractions, the product was isolated (512 mg) as a waxy white solid in 89% yield, which was used directly in the next step.

Step 2: The product of step 1 was dissolved in $CH_3OH$ (1.8 ml) and a solution of 1.0 M $Na_2CO_3$ (1.5 ml) was added. After stirring at RT for 36 h, the resulting mixture was evaporated to dryness, toluene (2 ml) was added and the mixture was evaporated to dryness. The resulting crude solid (153 mg) was used directly in the next step without purification.

Step 3: The product of Example 4, step 6 (94 mg), and the product of step 2 (immediately above) (76 mg) were subjected to the same reaction conditions as in Example 23, step 4, using HOBt (92 mg), DEC (130 mg), diisopropyl ethylamine (0.14 ml) and DMF (0.25 ml). After extraction and purification by preparative thin layer chromatography (1000 $\mu$M silica plate; 95:5 EtOAc:$Et_3N$ eluant), the free base form of the title compound was isolated (52 mg) as a foam in 40% yield. HRMS: calc'd: $M+H^+$: $C_{27}H_{37}N_5O_2F_3$: 520.2899; measured: 520.2908.

Step 4: The product of step 3 (52 mg) was subjected to the reaction conditions in Example 23, step 5, using EtOAc (1.0 ml) and HCl (4.0 M solution in 1,4-dioxane; 75 $\mu$l) to give, after work up, the title compound (44.5 mg) as a white solid in 76% yield. mp: decompostion above 161° C.

Using similar procedures, the compounds of the formula:

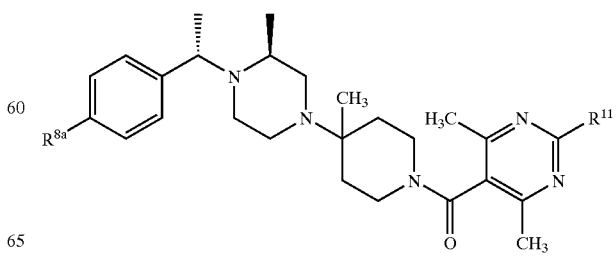

were prepared, wherein $R^{8a}$ and $R^{11}$ are defined in the table:

| Ex. | $R^{8a}$ | $R^{11}$ | m.p. (° C.) |
| --- | --- | --- | --- |
| 23D | —CF$_3$ | —OH | 175–185 |
| 23E | —CF$_3$ | —OCH$_3$ | 169–173 |
| 23F | —CF$_3$ | —NH$_2$ | 200–210 |
| 23G | —CF$_3$ | —NHCONHEt | 184–190 |
| 23H | —CF$_3$ | —CF$_3$ | 83–86 |
| 23I | —CF$_3$ |  | 154–159 |
| 23J | —CF$_3$ | —SCH$_3$ | >176 (dec) |
| 23K | —OCF$_3$ | —CH$_3$ | 205–210 |
| 23L | —OCF$_3$ | Ph | 239–242 |
| 23M | —OCF$_3$ | —OCH$_3$ | 200–210 |
| 23N | —OCF$_3$ | —OH | 185–191 |

EXAMPLE 24

Arylcyclopropylamides

Method A:

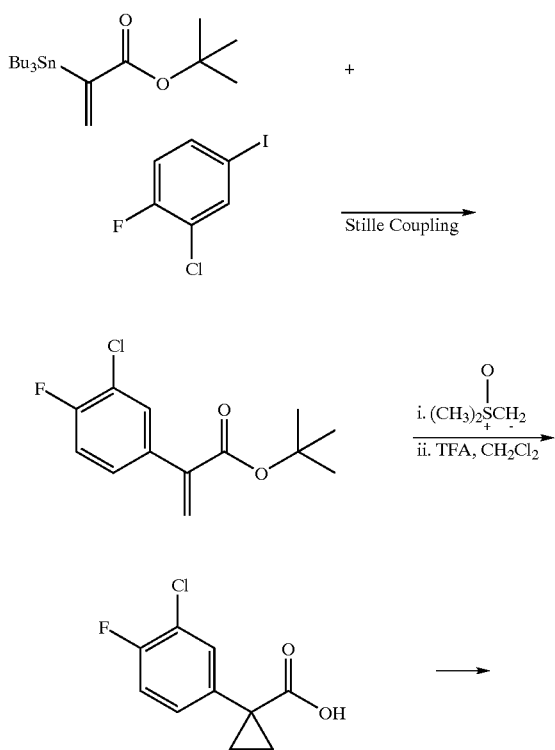

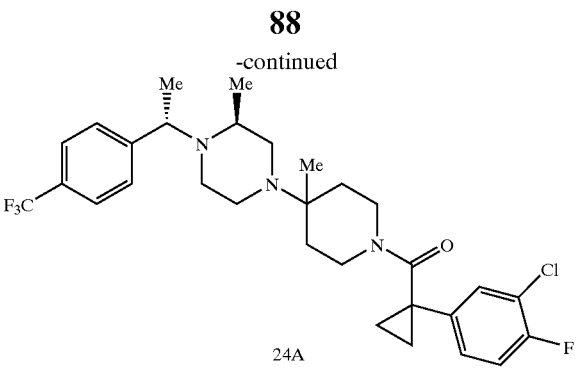

Step 1: To the stannane (0.39 g, 0.95 mmol) in DMF (10 ml) was added the 2-chloro-4-fluoroiodobenzene (0.73 g, 2.86 mmol), CuI (0.19 g, 1.05 mmol) and tetrakis(triphenylphosphine)palladium (0) (0.11 g, 0.095 mmol). The reaction was stirred at RT under N$_2$ for 21 h. The reaction mixture was added to Et$_2$O and the heterogeneous solution filtered through a bed of celite, washing with EtOAc. The filtrate was washed with water and brine and dried (MgSO$_4$). Filtration and evaporation of the solvent in vacuo afforded a residue that was preadsorbed on silica gel. Purification by silica gel chromatography (4% EtOAc/hexane) yielded the arylacrylate (0.19 g, 78%), which was used directly in the next step.

Step 2: To trimethylsulfoxonium iodide (0.18 g, 0.81 mmol) in DMSO (1.6 ml) was added potassium tert-butoxide (0.09 g, 0.81 mmol). The reaction mixture was stirred at RT for 1 h, at which time the arylacrylate (0.19 g, 0.74 mmol) in DMSO (1.6 ml) was added. The reaction mixture was stirred at RT for 5 h and water was added. The mixture was extracted with EtOAc. The combined organic layers were washed with water and brine and dried (MgSO$_4$). Filtration and evaporation of the solvent in vacuo afforded the arylcyclopropyl ester that was used directly by taking up into CH$_2$Cl$_2$ (3 ml) and adding TFA (0.5 ml). The reaction mixture was stirred at RT for 15 h and then concentrated in vacuo to afford the arylcyclopropylcarboxylic acid (0.14 g, 91%-2 steps). Without further purification, the carboxylic acid was coupled to the product of example 8, step 3, using the procedure of Example 8, step 4 to obtain 24A as the HCl salt. HRMS (M+H): found 566.2561.

Method B:

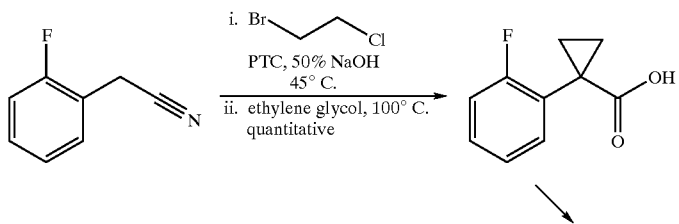

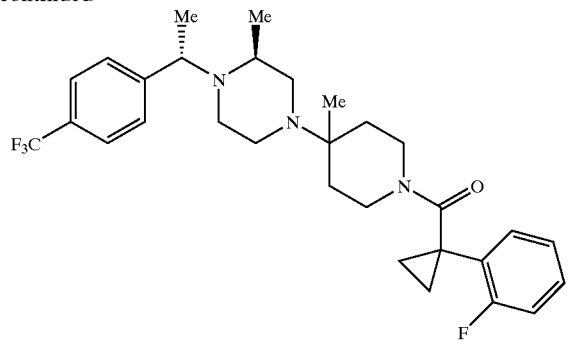

24B

To the 2-fluorophenylacetonitrile (0.80 g, 5.92 mmol), benzyltriethylammonium chloride (0.03 g, 0.12 mmol), and 1-bromo-2-chloroethane (1.70 g, 11.9 mmol) was added 50% aqueous NaOH (3.5 ml). The reaction was stirred at 45° C. for 21 h and ethylene glycol was added (3 ml). The reaction was then warmed to 100° C. and stirred for 7 h. Upon cooling to RT, the reaction was diluted with water and washed with EtOAc. The aqueous layer was acidified to pH 2–3 with aqueous 6N HCl. The acidified solution was extracted with $Et_2O$. The combined $Et_2O$ extracts were washed with water and brine and dried ($MgSO_4$). Filtration and evaporation of the solvent in vacuo afforded a pale yellow solid (1.06 g, 99%). The arylcyclopropyl acid was coupled to the product of example 8, step 3, using the procedure of Example 8, step 4 to obtain 24B as the HCl salt. HRMS (M+H): found 532.2949.

Using similar procedures, the compounds of the formula:

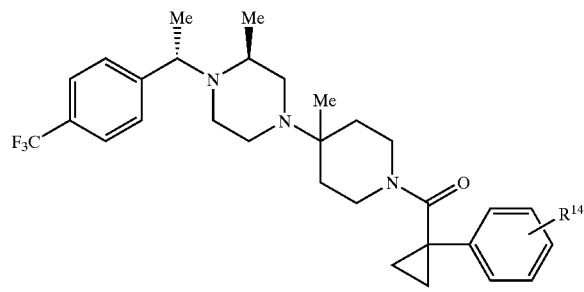

were prepared, wherein

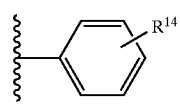

is defined in the table:

| Ex. | ![R14 phenyl] | HRMS (M + H) | m.p. (° C.) |
|---|---|---|---|
| 24C | phenyl | — | 240–245 |
| 24D | 4-Cl phenyl | — | >225 |
| 24E | 4-OCH$_3$ phenyl | — | 172–176 |
| 24F | 4-CH$_3$ phenyl | — | 225–230 |
| 24G | 2,4-diCl phenyl | — | >225 |
| 24H | 3-OCH$_3$ phenyl | 544.3151 | — |

-continued

| Ex. | ![R14 phenyl] | HRMS (M + H) | m.p. (° C.) |
|---|---|---|---|
| 24I | 4-Br-phenyl | 592.2150 | — |
| 24J | 4-F-phenyl | 532.2956 | — |
| 24K | 4-CN-phenyl | 539.3003 | — |
| 24L | 4-COOH-phenyl | 558.2949 | — |
| 24M | 4-COOCH₃-phenyl | 572.3107 | — |
| 24N | 3-CF₃-phenyl | 582.2910 | — |
| 24O | 4-CF₃-phenyl | 582.2910 | — |
| 24P | 3-thienyl | 520.2609 | — |
| 24Q | 3-pyridyl | 515.2991 | — |

EXAMPLE 25

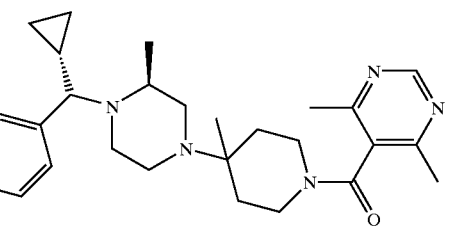

Step 1:

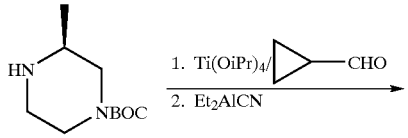

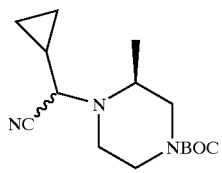

Cyclopropyl carboxaldehyde (3.4 ml), S-methyl N-BOC piperazine (8.28 g), CH₂Cl₂ (82 ml) and Ti(OiPr)₄ (15.80 ml) were mixed together and stirred at go RT for 23 h, then the resulting solution was cooled to 0° C. and Et₂AlCN (1.0 M in toluene; 62.1 ml) was added. The solution was stirred for 5 h at RT. A mixture of KF (20 g) and Celite (10 g) was added, followed by cautious addition of EtOAc (120 ml) and water (120 ml). The resulting slurry was stirred for 15 min, filtered, washed with EtOAc (3×35 ml) and the EtOAc layer was removed, washed with brine, dried over Na₂SO₄, filtered and evaporated to give the desired intermediate (12.0 g) which was used directly in the next step.

Step 2:

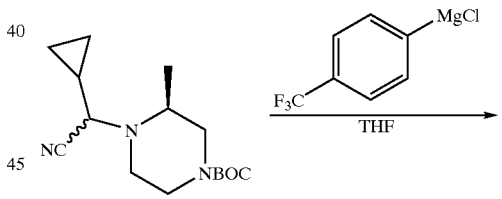

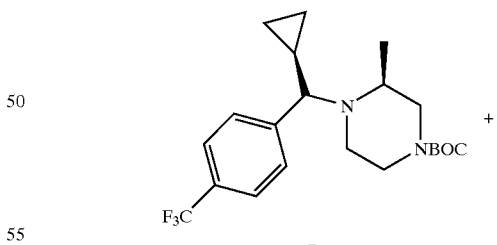
B

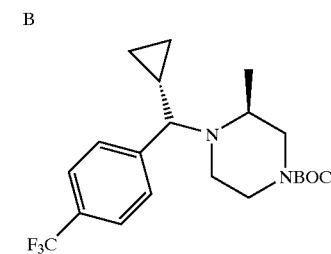
A

To a 0° C. solution of 4-iodobenzotrifluoride (40 g) and THF (52 ml) was added isopropyl magnesium chloride (2.0 M in Et$_2$O; 74 ml). The resulting solution was stirred at RT for 1 h and then added to a 0° C. solution of the product of step 1 (10.0 g) and THF (26 ml) over 10 min. The reaction solution was warmed to RT, stirred overnight and EtOAc (50 ml) was added. After stirring for 10 min, 2 N NaOH (50 ml) was added and the resulting mixture was stirred for 30 min, filtered and the salts were washed with EtOAc (3×20 ml). The combined EtOAc extracts were washed with brine, dried over Na$_2$SO$_4$, filtered and evaporated to give the crude product (28 g) as a gold oil which was chromatographed on silica gel (1 kg), eluting with hexanes:EtOAc (8:1). Two diastereomeric products were collected as a single fraction (15.9 g) and further purified by column chromatography as described above to give intermediate A (R$_f$=0.47 in 4:1 hexanes:EtOAc; 5.34 g), which was contaminated with an unidentified impurity. (The second diastereomer B (R$_f$=0.29 in 4:1 hexanes:EtOAc) was also collected.)

Step 3:

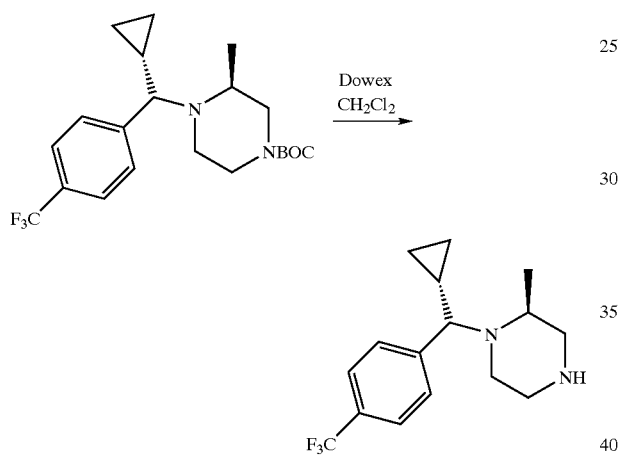

To a solution of A from Step 2 (3.96 g) and CH$_2$Cl$_2$ (120 ml) was added DOWEX 50X2-100 ion exchange resin (15 g) and the resulting mixture was shaken for 2.5 h at RT. The resin was filtered off and washed with CH$_2$Cl$_2$ (2×40 ml). The resin was treated with 7 N NH in CH$_3$OH (30 ml), the resin was filtered off and this procedure was repeated two times. The CH$_3$OH extracts were combined and evaporated. The resulting oil was treated with toluene:CH$_2$Cl$_2$ (1:1; 15 ml) and evaporated to give the piperazine intermediate (0.80 g) as a clear oil. HRMS: calc'd: M H$_{30}$ : C$_{16}$H$_{21}$N$_2$F$_3$:299.1735; measured:299.1748.

Step 4:

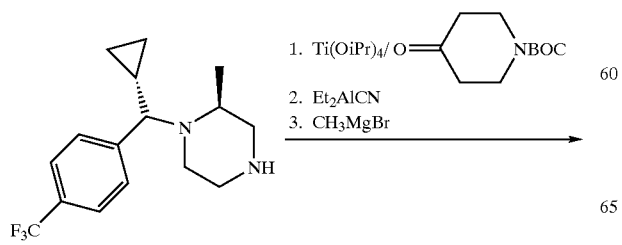

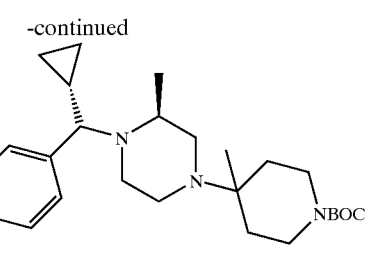

The product of Step 3 (0.57 g) was treated in the same fashion as Example 8, Step 1, using N-BOC 4-piperidone (0.42 g), CH$_2$Cl$_2$ (3.84 ml), Ti(OiPr)$_4$ (3.39 ml), Et$_2$AlCN (2.88 ml) and CH$_3$MgBr (3.0 M in Et$_2$O; 3.2 ml) to give the desired product (0.78 g) as a clear oil in 82% yield.

Step 5: The product of Step 4 (0.12 g) was treated with AcOH:CH$_2$Cl$_2$ (3:1, v:v; 1.4 ml) followed by BF$_3$Et$_2$O (0.14 ml). After stirring for 1 h, the resulting solution was diluted with CH$_2$Cl$_2$ (10 ml), cooled to 0° C. and the pH was adjusted to 10 with solid NaOH. Water (2 ml) was added and the CH$_2$Cl$_2$ layer was removed. After further extraction (2×10 ml) with CH$_2$Cl$_2$. the organic layer was washed with water, brine, dried over Na$_2$SO$_4$, filtered and evaporated to give the free piperidine (80 mg) in 81% yield.

Step 6: The product of Step 5 (57 mg) was treated in the same fashion as in Example 8, Step 4, using DMF (0.30 ml), HOBt (41 mg), DEC (57 mg), diisopropyl ethyl amine (0.08 ml) and 4,6-dimethyl 5-pyrimidine carboxylic acid (43 mg); the reaction was stirred at 45° C. for 5 h. Purification of the crude oil was carried out by preparative plate chromatography (silica adsorbent; 2000 μM; 76:19:5 EtOAc:hexanes:Et$_3$N as eluant) to give, after elution of the desired band (1:1 CH$_2$Cl$_2$:MeOH) and concentration of solvent, the title compound (70 mg) as a clear oil in 93% yield. The HCl salt was prepared as described for Example 8, Step 4 (78 mg) in 100% yield. mp:147–149° C.

Using a similar procedure, the following compound was prepared:

25A

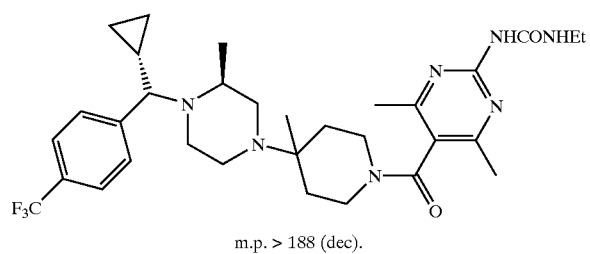

m.p. > 188 (dec).

EXAMPLE 26

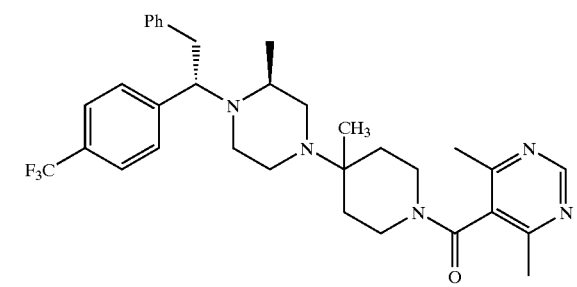

Step 1:

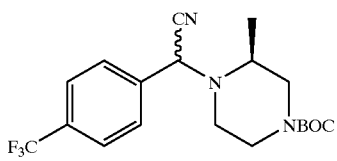

The desired compound was prepared in a manner similar to Example 25, Step 1, using p-trifluoromethyl benzaldehyde (20 g) instead of cyclopropyl carboxaldehyde, to give, after work up, a mixture of diastereomers (22.7 g) in 59% yield.

Step 2:

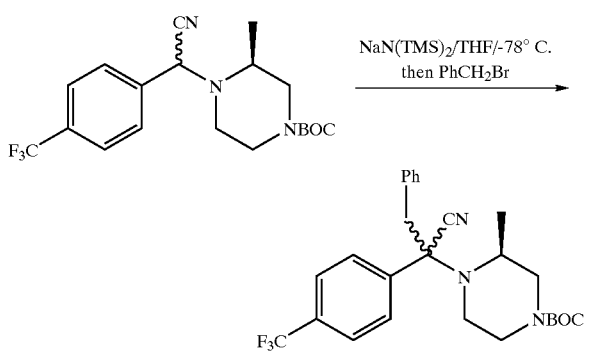

To a −70° C. solution of the product of step 1 (1.9 g) and THF (15 ml) was added NaHMDS (1.0 M in THF; 7.5 ml) followed by benzyl bromide (2 ml). The cooling bath was removed and the resulting solution was stirred for 45 min. Concentrated NH$_4$OH (10 ml) was added and the reaction was stirred for 30 min. The resulting mixture was partitioned between water and CH$_2$Cl$_2$, the CH$_2$Cl$_2$ extracts were removed and evaporated and the crude oil was purified by column chromatography (silica gel; 2:1 hexanes:CH$_2$Cl$_2$; 10:1 to 7:1 hexanes:EtOAc as eluant) to give, after evaporation of the appropriate fractions, a mixture of intermediates (1.92 g) as a yellow foam.

Step 3:

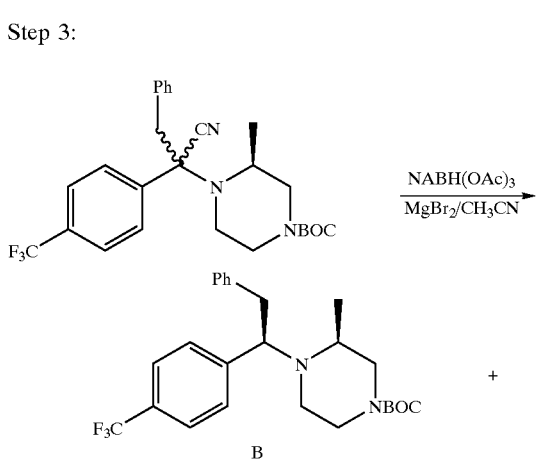

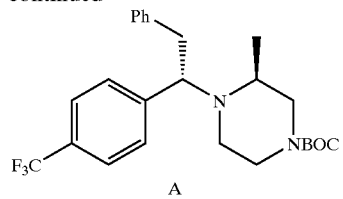

The mixture of Step 2 (1.91 g), CH$_3$CN (35 ml), sodium triacetoxy borohydride (4.0 g) and magnesium bromide etherate (2.25 g) were mixed and stirred at RT for 70 h. Water (25 ml) was added and then, gradually, a solution of Na$_2$CO$_3$ (10 g) in water (50 ml). After extraction with EtOAc (2×50 ml), drying and evaporation of the organic layer, the resulting oil was purified by preparative plate chromatography (5×2000 mM silica plates; 6:1 hexanes:EtOAc as eluant). The less polar band was removed, treated with 1:1 methanol:CH$_2$Cl$_2$ filtered and evaporated to give intermediate A (0.84 g) as a white foam. HRMS: calc'd: M H$^+$: C$_{25}$H$_{29}$O$_2$N$_2$F$_3$:449.2407; measured:4492416.

Step 4: The product of Step 3 (0.81 g) was treated in the same fashion as in Example 8, Step 3, using TFA (5 ml) and CH$_2$Cl$_2$ (10 ml), to give, after work up, the free piperazine (0.60 g) as a clear gum. HRMS: calc'd: M H$^{30}$ : C$_{20}$H$_{23}$N$_2$F$_3$: 349.1892; measured:349.1894.

Step 5: The product of Step 4 (0.39 g) was treated in the same fashion as in Example 8, Step 1, using N-BOC 4-piperidone (0.25 g), CH$_2$Cl$_2$ (8 ml), Ti(OiPr)$_4$ (0.40 mg), Et$_2$AlCN (2 ml) and CH$_3$MgBr (3.0 M in Et$_2$O; 1.5 ml) to give the desired BOC-protected piperidinyl intermediate (0.44 g) as a clear oil in 72% yield. HRMS: calc'd: M H$^+$: C$_{31}$H$_{42}$O$_2$N$_3$F$_3$:546.3307; measured:546.3315.

Step 6: The product of step 5 (0.43 g) was treated in the same fashion as in Example 8, Step 3, using TFA (3 ml), CH$_2$Cl$_2$ (2 ml) and water (0.2 ml) to give, after work up, the free piperidinyl intermediate (0.37 g) as a clear oil.

Step 7: The product of step 6 (50 mg) was treated in the same fashion as in Example 8, Step 4, using CH$_2$Cl$_2$ (3 ml), HOBt (28 mg), DEC (40 mg), diisopropyl ethyl amine (42 mg) and 4,6-dimethyl 5-pyrimidine carboxylic acid (24 mg); the reaction was stirred at RT for 2 days. Using the procedure described in Example 8, Step 4, the HCl salt of the title compound was prepared (59 mg) in 91% yield (from the product of Step 5). M.p:187–196° C. HRMS: calc'd: MH$^+$: C$_{33}$H$_{40}$ON$_5$F$_3$:580.3263; measured:580.3263.

Using a similar procedure, compounds of the formula:

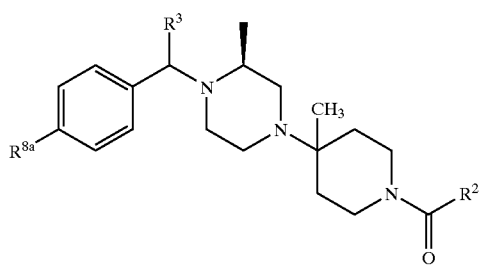

were prepared, wherein $R^{8a}$, $R^3$ and $R^2$ are defined in the table:

| Ex. | $R^{8a}$ | $R^3$ | $R^2$ | Mp (° C.) |
|---|---|---|---|---|
| 26B | —CF3 | benzyl | 4,6-dimethyl-2-phenylpyrimidin-5-yl | 86–92 |
| 26C | —CF3 | benzyl | 2,4,6-trimethylpyrimidin-5-yl | 83–90 |
| 26D | —CF3 | benzyl | 3,5-dimethyl-4-hydroxyphenyl | 195–205 |
| 26E | —CF3 | benzyl | 3,5-dimethyl-4-(NHCONHEt)phenyl | 118–125 |
| 26F | —OCF3 | benzyl | 4,6-dimethyl-2-methoxypyrimidin-5-yl | 175–185 |
| 26G | —OCF3 | benzyl | 4,6-dimethyl-2-hydroxypyrimidin-5-yl | 180–190 |
| 26H | —OCF3 | benzyl | 4,6-dimethylpyrimidin-5-yl | 220–230 |
| 26I | —OCF3 | benzyl | 2,4,6-trimethylpyrimidin-5-yl | 195–210 |

-continued

| Ex. | R⁸ᵃ | R³ | R² | Mp (° C.) |
|---|---|---|---|---|
| 26J | —OCF3 | benzyl | 3,5-dimethyl-5-chlorophenyl | 190–200 |
| 26K | —OCF3 | benzyl | 1-phenylcyclopropyl | 180–205 |
| 26L | —OCF3 | benzyl | 3,5-dimethyl-4-hydroxyphenyl | 230–240 |
| 26M | —OCF3 | benzyl | 3-phenyl-5-methylisoxazol-4-yl | 60–65 |
| 26N | —OCF3 | benzyl | 3-(2-chlorophenyl)-5-methylisoxazol-4-yl | 65–68 |
| 26O | —OCF3 | benzyl | 2,4-dimethylpyridine-N-oxid-3-yl | 60–62 |
| 26P | —CF3 | 3-fluorobenzyl | 4,6-dimethylpyrimidin-5-yl | 256–258 |
| 26Q | —CF3 | (5-chlorothien-2-yl)methyl | 4,6-dimethylpyrimidin-5-yl | 254–256 (dec) |

-continued

| Ex. | R^{8a} | R^3 | R^2 | Mp (° C.) |
|---|---|---|---|---|
| 26R | —CF3 | 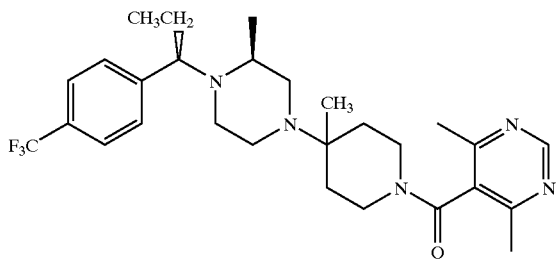 | | 249–250 (dec) |

EXAMPLE 27

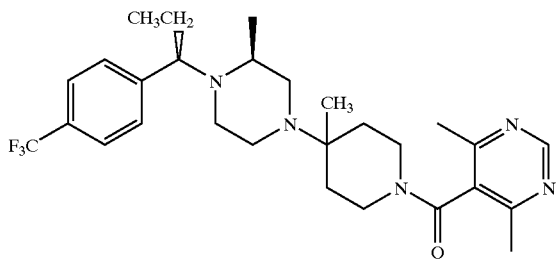

Step 1:

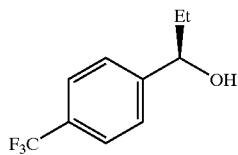

4'-Trifluoromethyl)propiophenone (2.02 g, 0.01 mol) and (S)-2-methyl-CBS-oxazaborolidine (1M in THF) (2.0 ml, 0.002 mol) in THF (10 ml) was cooled in an ice-bath and borane-methyl sulfide complex (2M in THF) (3 ml, 0.006 mol) was added dropwise to the mixture. The mixture was stirred for 30 min at 0° C. and $CH_3OH$ was added slowly until no bubbles appeared. The solvents were removed under reduced pressure and HCl solution (1N) was added to the mixture. EtOAc extractive work up followed by silica gel chromatography afforded the alcohol (1.47 g) in 72% yield.

Step 2: A solution of the product of Step 1 (4.32 g, 0.021 mol) and $Et_3N$ (5.9 ml, 0.042 mol) in $CH_2Cl_2$ (20 ml) was cooled to 0° C. in ice bath and $CH_3SO_2Cl$ (2.13 ml, 0.028 mol) was added dropwise. The mixture was stirred at 0° C. for 1 h and the ice bath was removed. Water was added to the mixture and $CH_2Cl_2$ extractive work up afforded the mesylate (5.99 g) in quantitative yield.

Step 3: The product of Step 2 (5.93 g, 0.021 mol) and 1-tert-butoxycarbonyl-3S -methyl piperazine (4.2 g, 0.021 mol) were dissolved in anhydrous $CH_3CN$ (20 ml) and oven-dry $K_2CO_3$ (4.35 g, 0.032 mol) was added to the solution. The mixture was stirred under reflux for 2 days, then diluted with water. EtOAc extractive work up followed by silica gel chromatography gave the desired product (3.16 g) in 39% yield.

Step 4: TFA (10 ml) was added to a solution of the product of Step 3(1.15 g, 2.59 mmol) in $CH_2Cl_2$ (5 ml) and the mixture was stirred at RT for 2 h, then concentrated under reduced pressure. NaOH (3N) was added to the residue and extractive work up with EtOAc gave the desired amine in quantitative yield.

Step 5: The product of Step 4 and 1-tert-butoxycarbonyl-4-piperidone (0.94 g, 4.74 mmol) were treated with $Ti(OiPr)_4$, Et, AlCN and $CH_3MgBr$ in a manner similar to that described in Example 8, step 1, to obtain the desired product (1.09 g) in 87% yield (from the amine of Step 4).

Step 6: TFA (4 ml) was added to a solution of the product of Step 5 (0.76 mg, 1.57 mmol) in $CH_2Cl_2$ (2 ml) and the mixture was stirred at RT for 2 h before it was concentrated under reduced pressure. NaOH (3N) was added to the residue and extractive work up with EtOAc gave the desired amine in quantitative yield.

Step 7: The amine of Step 6 and 4,6-dimethylpyrimidine 5-carboxylic acid (0.36 g, 2.35 mmol), were coupled as described in Example 8, Step 4, to obtain the title compound (0.58 g) in 72% yield. M.p. 160; HRMS (MH+) found: 518.3123.

Using a similar procedure, compounds of the formula:

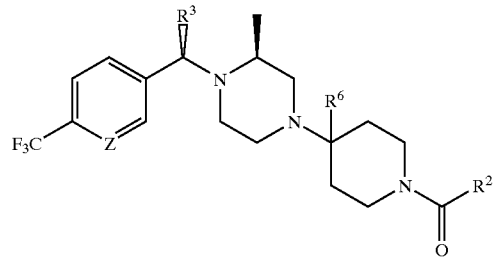

were prepared, wherein Z, $R^3$, $R^6$ and $R^2$ are defined in the table below:

| Ex. | Z | R^3 | R^6 | R^2 | Dec. (0° C.) | HRMS |
|---|---|---|---|---|---|---|
| 27A | N | Me | H | 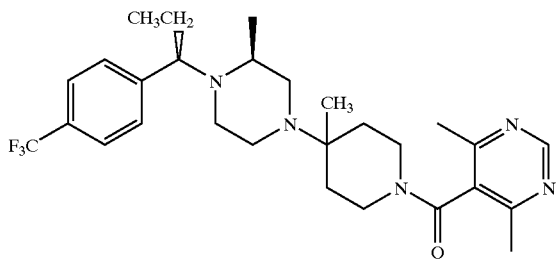 | 185 | 491.2744 |

-continued
| Ex. | Z | R³ | R⁶ | R² | Dec. (0° C.) | HRMS |
|---|---|---|---|---|---|---|
| 27B | N | Me | H | 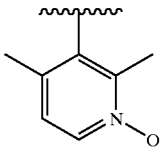 | 190 | 506.2729 |
| 27C | N | Me | Me | 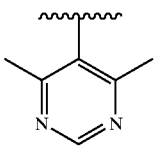 | 190 | 505.2898 |
| 27D | N | Me | Me | 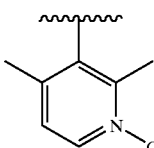 | 200 | 520.2902 |
| 27E | CH | Et | Me | 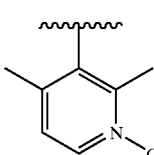 | 197 | 533.3097 |
| 27F | CH | Et | Me | 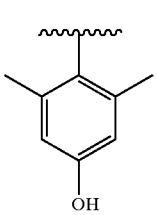 | 215 | 532.3147 |
| 27G | CH | Et | Me | 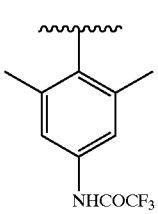 | 230 | 627.3145 |
| 27H | CH | Et | Me | 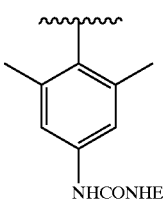 | 210 | 602.3678 |
| 27I | CH | Et | Me | 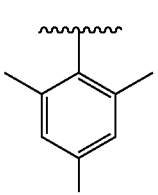 | 215 | 531.3305 |

-continued
| Ex. | Z | R³ | R⁶ | R² | Dec. (0° C.) | HRMS |
|---|---|---|---|---|---|---|
| 27J | CH | Et | Me | 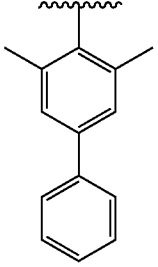 | 215 | 593.3470 |
| 27K | CH | Et | Me | 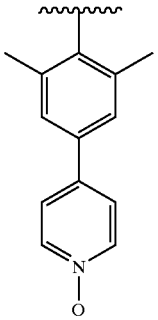 | 195 | 609.3424 |
| 27L | CH | Et | Me | 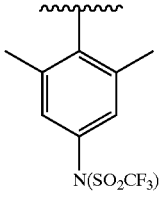 | 170 | 745.2308 |
| 27M | N | n-Pr | Me | 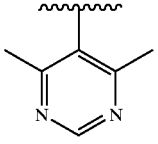 | 204 | 533.3207 |
| 27N | N | n-Pr | Me | 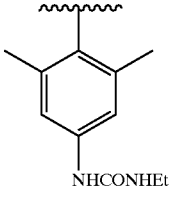 | 210 | 617.3798 |
| 27O | N | n-Pr | Me | 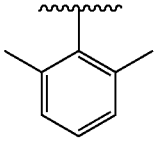 | 202 | 531.3304 |
| 27P | N | n-Pr | Me | 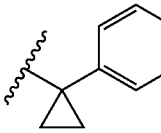 | 165 | 543.3311 |

-continued

| Ex. | Z | R³ | R⁶ | R² | Dec. (0° C.) | HRMS |
|---|---|---|---|---|---|---|
| 27Q | N | n-Pr | Me | (3-phenyl-5-methylisoxazol-4-yl) | 225 | 584.3205 |
| 27R | N | n-Pr | Me | (2,4-dimethylpyridine N-oxide-3-yl) | 195 | 548.3217 |

Using similiar procedures, the following compounds were also prepared:

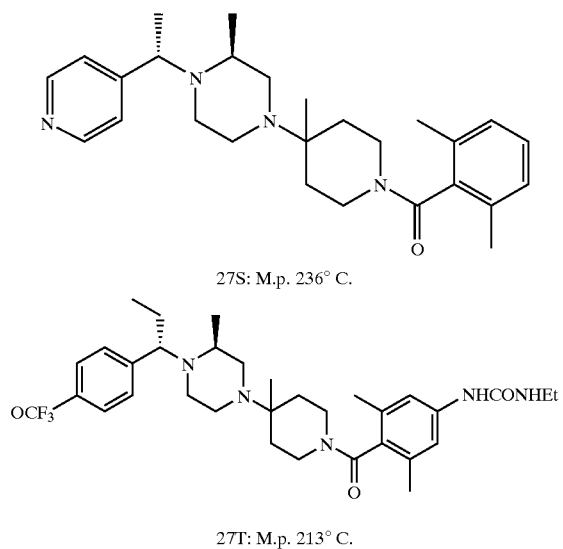

27S: M.p. 236° C.

27T: M.p. 213° C.

EXAMPLE 28

Steps 1–4:

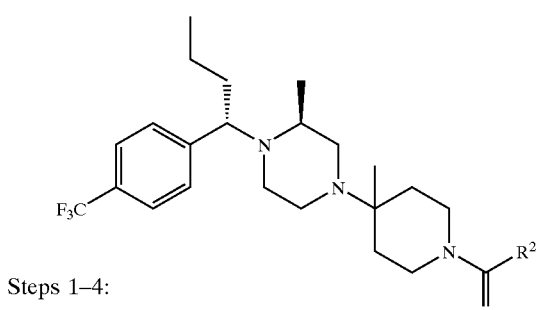

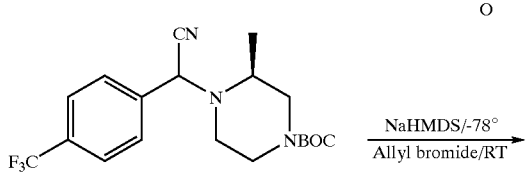

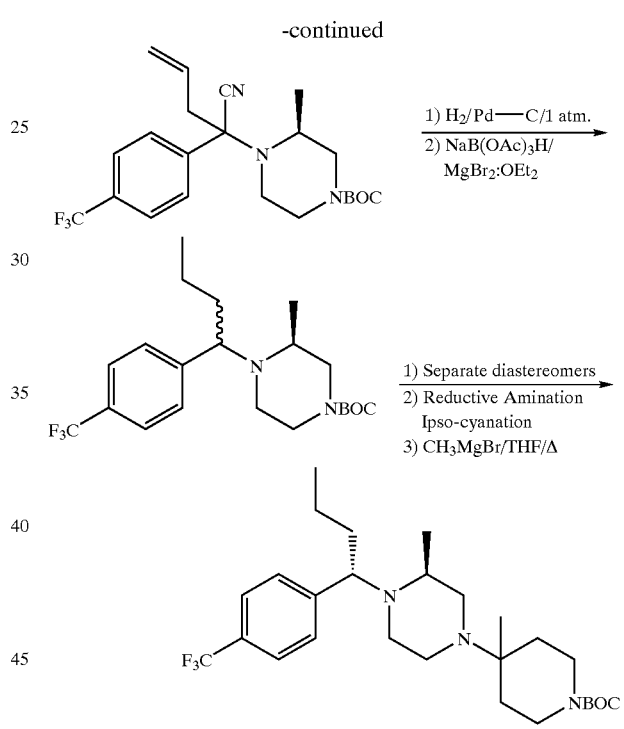

Step 1: The cyano amine was prepared from p-trifluoromethyl benzaldehyde and 2(S)-methyl-4-(tert-butoxycarbonyl) piperazine exactly as described in Example 6, Step 1.

Step 2: A solution of the cyano amine 2 (2.5 g; 6.53 mmol) in 30 ml of dry THF was placed under a blanket of $N_2$ and cooled to −78° C. This solution was treated with a solution of sodium hexa-methyl disilazide in THF (1M; 26 ml) followed after 5 min with neat allyl bromide (6 ml). Upon removal of the bath and letting the reaction mixture warm to RT (~1 h), it changed from a yellow solution to dark reddish brown solution. The reaction was quenched with saturated $NH_4Cl$ solution and the product extracted with EtOAc, washed with water, brine and dried. Concentration in vacuo afforded a brown semi solid. FSGC of this material using 25% Et$_2$O in hexane as eluant gave 2.5 grams (92%) of the desired product as an amber gum (TLC R$_f$=0.65, 0.6 for two overlapping spots).

Step 3: A solution of the product of Step 2 (2.4 g) in CH$_3$OH was treated with 10% Pd/C (0.2 g) and placed under a balloon of H$_2$ gas. After stirring at RT for 4 h, the catalyst was removed via filtration through celite. Concentration of the filtrate yielded an amber gum.

The α-propyl nitrile obtained above was dissolved in CH$_3$CN (12 ml). Magnesium bromide etherate (2.1 g; 8.14 mmol) and sodium triacetoxy borohydride (3.44 g; 16.2 mmol) were added and the reaction mixture was stirred at RT overnight. The reaction was quenched with water and rendered basic with saturated NaHCO$_3$. The organic products were extracted with EtOAc and processed to obtain ~2 g of crude material. FSGC (10–25% EtO in hexane) served to isolate two diasteromeric products (1.7 g total; 79% for two steps):

(S, S)-Diastereomer (A): TLC R$_f$=0.6 (25% Et$_2$O-Hexane). 0.9 g of a colorless gum.

(R, S)-Diastereomer (B): TLC R$_f$=0.5 (25% Et$_2$O-Hexane). 0.8 g of a colorless gum.

Step 4: Removal of the BOC-protecting group from the intermediate A was accomplished by treatment with TFA in CH$_2$Cl$_2$. The isolated free piperazine (0.68 g; 2.3 mmol), N-(tert-butoxycarbonyl)-4-piperidinone (0.45 g; 2.3 mmol) and Ti(OiPr)$_4$ (0.7 mL; 2.5 mmol) were dissolved in 10 ml of CH$_2$Cl$_2$ and stirred overnight. Et$_2$AlCN (1M in toluene; 2.7 ml) was introduced into the reaction mixture and the resultant solution was stirred for a day. The reaction was diluted with EtOAc and quenched with water. Celite was added to aid in the filtration of titanium and aluminum salts. The biphasic filtrate was washed with water, brine and dried. Concentration in vacuo yielded 1.1 g of a yellow gum (TLC R$_f$=0.55 in 25% EtOAc-hexane).

The resultant ipso-cyano compound was dissolved in dry THF (8 ml) and treated with a solution of CH$_3$MgBr (3M in Et$_2$O; 6 ml) and stirred overnight at RT. The reaction flask was placed in a cold water bath and carefully quenched with saturated NH$_4$Cl solution. The organic product was extracted with EtOAc and washed with water and brine. Concentration to a crude product which was purified by rapid FSGC (10–25% EtOAc in hexane) gave the BOC-piperidinyl compound as a pale yellow gum (1.1 g; 100%). TLC R$_f$=0.6 in 25% EtOAc-hexane.

Step 5: The BOC-protecting group on the piperidine nitrogen in the product of Step 4 was removed by treatment with TFA in CH$_2$Cl$_2$. Basification with 1 M NaOH and processing in CH$_2$Cl$_2$ afforded the unprotected piperidine in 90% yield. This intermediate was coupled (EDCl, HOBt) to aryl and heteroaryl carboxylic acids to obtain the amides exemplified in the following table:

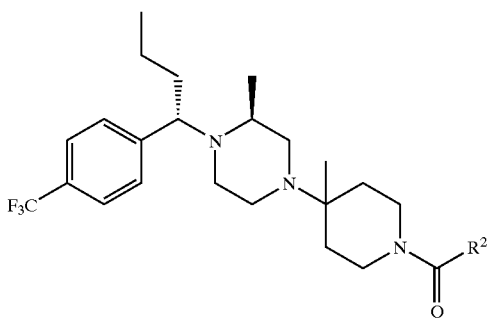

wherein R$^2$ is as defined in the table:

| Ex. | R$^2$ | Mp (° C.) | HRMS (MH$^+$) |
|---|---|---|---|
| 28A | 4,6-dimethylpyrimidin-5-yl | 249 | Calculated: 532.3263<br>Found: 532.3268 |
| 28B | 2,4-dimethylpyridine N-oxide | 59 | Calculated: 547.3260<br>Found: 547.3278 |
| 28C | 2,6-dimethylphenyl | 246 | Calculated: 530.3358<br>Found: 530.3372 |
| 28D | 1-phenylcyclopropyl | 239 | Calculated: 542.3358<br>Found: 542.3361 |
| 28E | 4,5-dimethyl-3-phenylisoxazole | 258 | Calculated: 583.3260<br>Found: 583.3272 |
| 28F | 3,5-dimethyl-4-(pyridin-4-yl N-oxide)phenyl | 102 | Calculated: 623.3573<br>Found: 623.3572 |
| 28G | 3,5-dimethyl-4-aminophenyl | 216 | Calculated: 545.3467<br>Found: 545.3459 |
| 28H | 3,5-dimethyl-4-hydroxyphenyl | 217 | Calculated: 546.3307<br>Found: 546.3309 |
| 28I | 3,5-dimethyl-4-(N-ethylurea)phenyl | 223 | Calculated: 616.3838<br>Found: 616.3848 |

Using similar procedures, the following compounds were prepared:

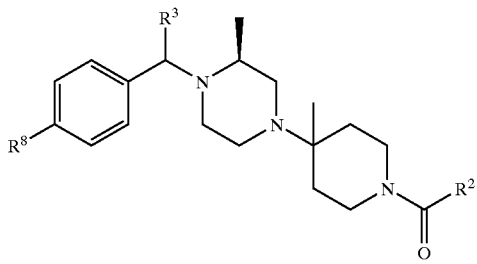

wherein R⁸, R³ and R² are as defined in the table:

| Ex. | R⁸ | R³ | R² | Mp (° C.) |
|---|---|---|---|---|
| 28J | —CF₃ | phenyl-CH₂ | 4,6-dimethylpyrimidin-5-yl | 195–220 |
| 28K | —CF₃ | phenyl-CH₂ | 3,5-dimethyl-4-(NHCONHEt)phenyl | 105–115 |
| 28L | CH₃CONH— | ethyl | 4,6-dimethylpyrimidin-5-yl | 177–180 |
| 28M | —CF₃ | CH₂CF₃ | 4,6-dimethylpyrimidin-5-yl | 224–232 |

Using 3-fluoro benzyl bromide or chloride in place of benzyl bromide in the procedure of Example 28, steps 1–4 (processing isomer B in step 3), then using the process of Example 1, step 5, followed by the process of Example 26, steps 6–7, the following compound was prepared (HCl salt):

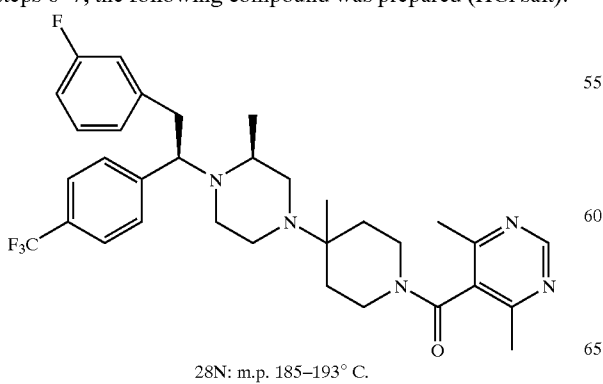

28N: m.p. 185–193° C.

EXAMPLE 29

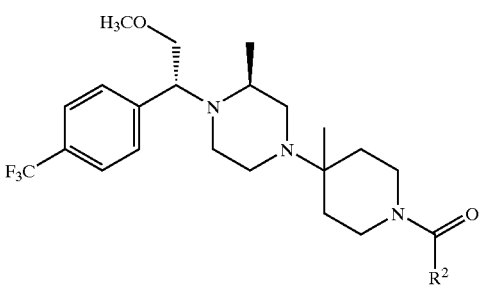

Steps 1–3:

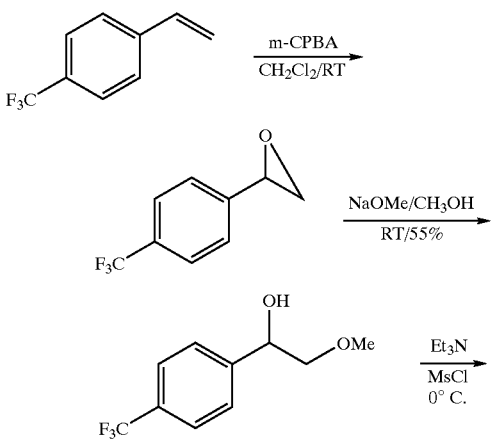

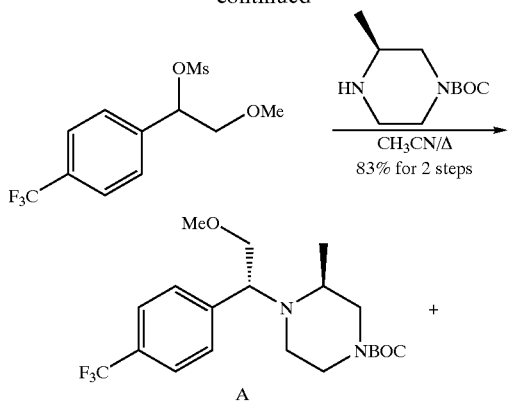

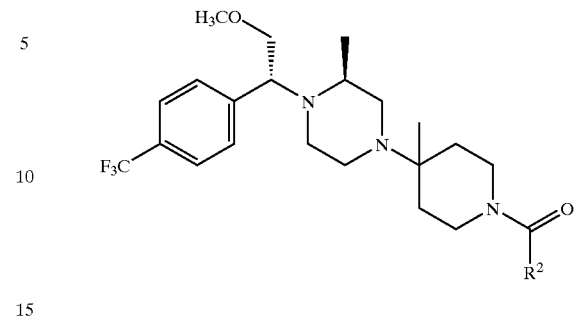

described in Example 8, step 4, to obtain the compounds shown in the following table:

wherein R² is as shown in the table:

| Ex. | R² | Mp (° C.) | HRMS (MH⁺) |
|---|---|---|---|
| 29A | ![dimethylpyrimidine] | 163 | Calculated: 534.3056<br>Found: 534.3050 |
| 29B | ![dimethylphenol-OH] | 208 | Calculated: 548.3100<br>Found: 548.3092 |
| 29C | ![dimethylpyridine N-oxide] | 101 | Calculated: 549.3053<br>Found: 549.3057 |
| 29D | ![dimethylphenyl urea ethyl] | 192 | Calculated: 618.3631<br>Found: 618.3638 |

Step 1: Solid m-CPBA was added to a solution of p-trifluoromethyl styrene (3 g; 17.4 mmol) in 30 ml of $CH_2Cl_2$ and stirred at RT for 20 h. About 20 ml of a saturated solution of $NaHCO_3$ was added and stirred at RT for 2 h. The mixture was diluted with 20 ml of $CH_2Cl_2$ and the organic product extracted into the $CH_2Cl_2$ layer. The organic extract was processed to obtain the crude product. FSGC gave 3 g (90%) of the desired epoxide as a colorless oil. TLC $R_f$=0.8 (25% EtOAc in hexane).

Step 2: Freshly prepared $NaOCH_3$ (0.6 g; 10.6 mmol) was added to a solution of the product of Step 1 (2 g; 10.6 mmol) in 20 ml of anhydrous $CH_3OH$. After stirring at RT for a day, $CH_3OH$ was removed in vacuo. The residue was dissolved in $CH_2Cl_2$ and washed with water and brine. Concentration, followed by FSGC, furnished 1.3 g (55%) of the carbinol as a colorless oil ($R_f$=0.3 50% $Et_2O$ in hexane).

Step 3: The carbinol of Step 2 (1.3 g; 5.9 mmol) was dissolved in $CH_2Cl_2$ and cooled in an ice bath. Sequential treatment with $Et_3N$ (1.7 ml; 12 mmol) and $CH_3SO_2Cl$ (0.6 ml; 7.7 mmol) and stirring for 30 min formed the mesylate. The product was extracted by standard work up (yield =100%).

The mesylate (1.76 g; 5.9 mmol) and 2(S)-methyl-4-(tert-butoxycarbonyl) piperazine (2.4 g; 12 mmol) were dissolved in 5 ml of $CH_3CN$ and heated to reflux for 19 h. The reaction mixture was cooled to RT and directly subjected to flash chromatography on silica gel. Eluting with 25%, then 50% $Et_2O$ in hexane served to isolate the diastereomeric products A and B (Total yield=86%).

A: $R_f$=0.5 (50% $Et_2O$ in hexane). Light yellow gum (0.9 g; 42%)

B: $R_f$=0.4 (50% $Et_2O$ in hexane). Amber gum (1.13 g; 44%)

Step 4: Reductive amination of the free piperazine dervied from A (0.9 g; 2.2 mmol) with N-BOC-piperidin-4-one with the installation of the isomethyl group was carried out as described in Example 1, step 4. to obtain the BOC-protected piperidinyl compound (0.87 g; 92%). $R_f$=0.3 (50% EtOAc in hexane).

Step 5: The BOC protecting group was removed from the piperidine nitrogen via TFA, and the resultant compound was coupled with acids using the EDCl/HOBt method as

EXAMPLE 30

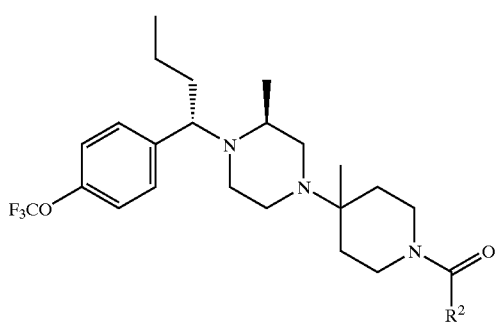

Step 1:

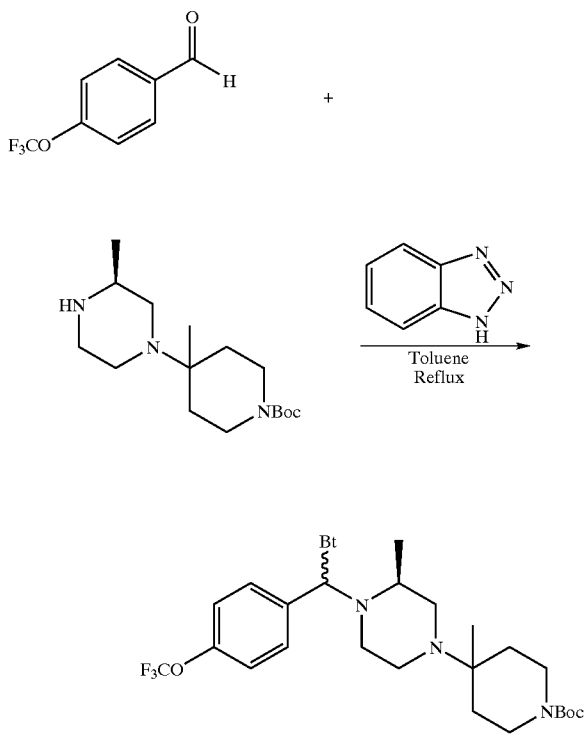

A solution of ptrifluoromethoxy benzaldehyde (0.48 ml, 3.36 mmol), the piperidino-pipiperazine (1.00 g, 3.36 mmol) and benzotriazole (0.48 g, 4.00 mmol) in dry toluene were heated at reflux for 6 h. The reaction mixture was cooled to RT and the solvent was removed in vacuo. Following NMR verification of the formation of the product, the product was used without further purification in the next step.

Step 2:

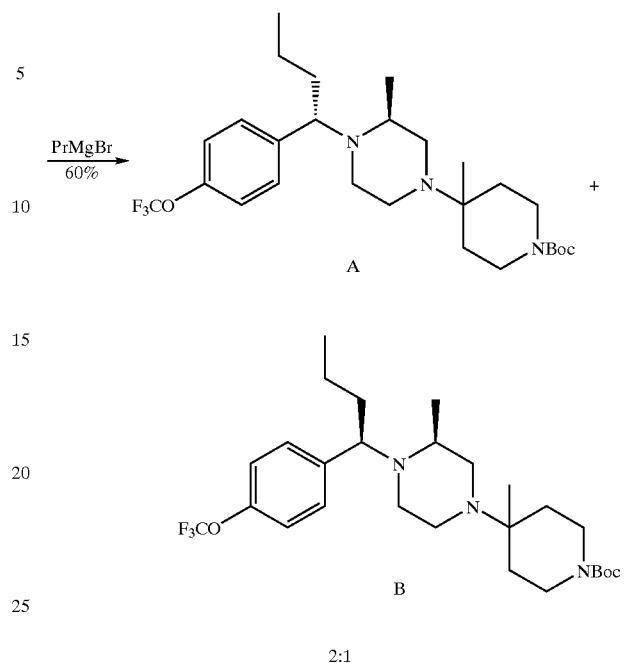

To a solution of the product of Step 1 (1.16 g, 1.97 mmol) in 20 ml of toluene was added a solution of n-propyl magnesium bromide (2M in $Et_2O$, 1.1 ml) and the mixture stirred at RT for 15 h. The reaction mixture was quenched by pouring onto ice and saturated aqueous $NH_4Cl$ solution. The aqueous layer was extracted with EtOAc, washed with 1M NaOH solution, water and brine. Concentration and purification by FSGC (20% EtOAc-hexane) provided the desired product A. Further elution with 300% EtOAc in hexane gave the (R, S) diastereomer B.

Step 3: The amine A was treated with TFA in $CH_2Cl_2$ to remove the BOC-protecting group. Coupling of the free piperidine with acids using EDCl/HOBt provided compounds 30–30B in the following table; similar methods were used to prepare compounds 30C–I.

| Ex. | $R^{8a}$ | $R^3$ | $R^2$ | Mp (° C.) | HRMS (MH+) found |
|-----|----------|-------|-------|-----------|------------------|
| 30 | —OCF$_3$ | n-Pr | 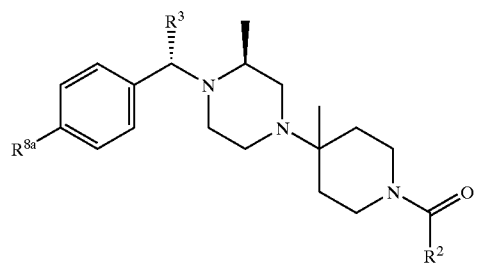 | 237 | 546.3314 |

-continued
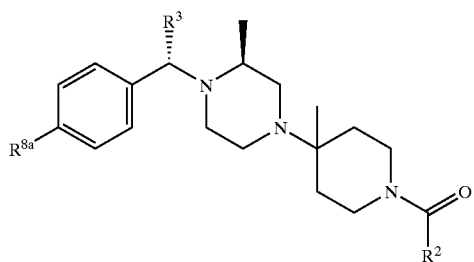
| Ex. | R$^{8a}$ | R$^3$ | R$^2$ | Mp (° C.) | HRMS (MH$^+$) found |
|---|---|---|---|---|---|
| 30A | —OCF$_3$ | n-Pr | 4,6-dimethylpyrimidin-5-yl | 241 | 548.3217 |
| 30B | —OCF$_3$ | n-Pr | 3,5-dimethyl-4-(3-ethylureido)phenyl | 219 | 632.3779 |
| 30C | H | phenyl | 4,6-dimethylpyrimidin-5-yl | 175–178 | — |
| 30D | H | phenyl | 3,5-dimethyl-4-(3-ethylureido)phenyl | 177–189 | — |
| 30E | H | phenyl | 1-(4-cyanophenyl)cyclopropyl | 84–90 | — |
| 30F | —CF$_3$ | 4-(trifluoromethyl)phenyl | 4,6-dimethylpyrimidin-5-yl | 180–192 | — |
| 30G | —CF$_3$ | phenyl | 4,6-dimethylpyrimidin-5-yl | 180–186 | — |

-continued

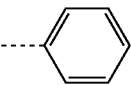

| Ex. | $R^{8a}$ | $R^3$ | $R^2$ | Mp (° C.) | HRMS (MH+) found |
|---|---|---|---|---|---|
| 30H | H | 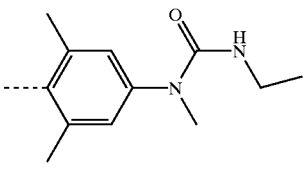 | 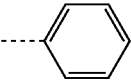 | 178–188 | — |
| 30I | —OCF$_3$ | 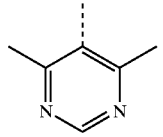 | 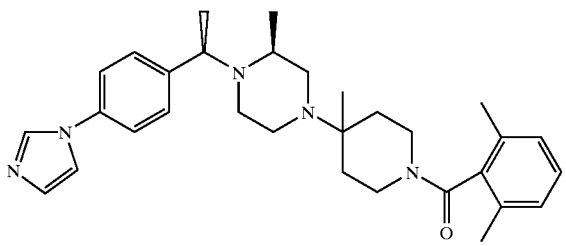 | 165–175 | — |

Mixture of Diastereomers

EXAMPLE 31

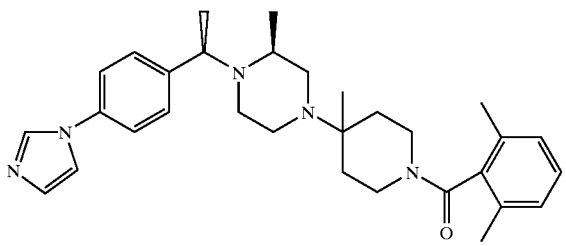

A solution of the product of Example 12, step 2 (150 mg, 0.27 mmol), imidazole (27.4 mg, 0.403mmol), 1,10-phenanthroline (48 mg, 0.27 mmol), trans,trans-dibenzylideneacetone (6.28 mg, 0.027 mmol), copper (II) trifluoromethanesulfonate benzene complex (15 mg, 0.027 mmol) and Cs$_2$CO$_3$ (96.1 mg, 0.30 mmol) in xylene (2 ml) was stirred at 110° C. for 5 days. The reaction mixture was cooled to RT and saturated NaHCO$_3$ was added. Extractive EtOAc work up followed by silica gel chromatography gave the title compound (70 mg, 52% yield). Dec. 215° C. (HCl salt). HRMS calcd for C$_{29}$H$_{39}$ClN$_3$OS (M+H+) 500.3389, found 500.3396.

The following assays can be used to determine the CCR5 antagonistic activity of the compounds of the invention.

CCR5 Membrane Binding Assay:

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in secondary cell-based HIV-1 entry and replication assays.

HIV-1 Entry Assay:

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al , Virology, 206 (1995), p. 935–944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay:

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates.

Following infection, the cells are washed to remove residual inoculum and cultured in the presence of compound for 4 days. Culture supernatants are harvested and viral replication measured by determination of viral p24 antigen concentration.

Calcium Flux Assay:

Cells expressing the HIV coreceptor CCR5 are loaded with calcium sensitive dyes prior to addition of compound or the natural CCR5 ligand. Compounds with agonist properties will induce a calcium flux signal in the cell, while CCR5 antagonists are identified as compounds which do not induce signaling by themselves but are capable of blocking signaling by the natural ligand RANTES.

GTPγS Binding Assay:

A GTPγS binding assay measures receptor activation by CCR5 ligands. This assay measures the binding of $^{35}S$ labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}S$ label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay:

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

The role of CC chemokine receptors such as CCR-5 receptors in inflammatory conditions has been reported in such publications as *Immunology Letters*, 57, (1997), 117–120 (arthritis); *Clinical & Experimental Rheumatoloy*, 17 (4) (1999), p. 419–425 (rheumatoid arthritis); *Clinical & Experimental Immunology*, 117 (2) (1999), p.237–243 (atopic dermatitis); *International Journal of Immunopharmacolocly*, 20 (11) (1998), p. 661–7 (psoriasis); *Journal of Allergy & Clinical Immunology*, 100 (6, Pt 2) (1997), p. S52–5 (asthma); and *Journal of Immunology*, 159 (6) (1997), p. 2962–72 (allergies).

In the assay to determine inhibition of RANTES binding, compounds of the invention range in activity from a Ki of about 0.5 to about 1500 nM, with preferred compounds having a range of activity from about 0.5 to about 750 nM, more preferably about 0.5 to 300 nM, and most preferably about 0.5 to 50 nM. The results for preferred and representative compounds of formulas I and II in the test to determine inhibition of RANTES binding are given in the table below. In the table, "Ex. No." stands for "Example Number" and "nM" stands for "nanomolar."

| Ex. No. | Ki (nM) Inhibition of RANTES binding |
| --- | --- |
| 3C | 9.97 |
| 6C | 30.0 |

| Ex. No. | Ki (nM) Inhibition of RANTES binding |
| --- | --- |
| 6E | 1.43 |
| 11 | 10.5 |
| 16 | 60 |
| 20A | 1300 |
| 23 | 2.95 |

For preparing pharmaceutical compositions of the CCR5 antagonist compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The CCR5 antagonist compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the CCR5 antagonist compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the CCR5 antagonist compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimen of the NRTIs, NNRTIs, PIs and other agents will be determined by attending clinician in view of the approved doses and dosage regimen in the package insert or as set forth in the protocol taking into consideration the age, sex and condition of the patient and the severity of the HIV-1 infection.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of treating Human Immunodeficiency Virus comprising administering to a human in need of such treatment a CCR5 antagonist represented by the structural formula II:

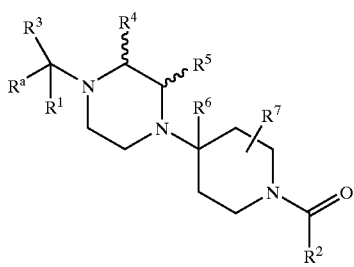

or a pharmaceutically acceptable salt thereof, wherein
(1) $R^2$ is $R^{8a}$-phenyl, $R^{8b}$-pyridyl $R^{8b}$-thiophenyl or $R^8$-naphthyl;
$R^1$ is hydrogen or $C_1$–$C_6$ alkyl;
$R^2$ is 6-membered heteroaryl substituted by $R^9$, $R^{10}$ and $R^{11}$; 6-membered heteroaryl N-oxide substituted by $R^9$, $R^{10}$ and $R^{11}$; 5-membered heteroaryl substituted by $R^{12}$ and $R^{13}$; naphthyl; fluoronyl; diphenylmethyl;

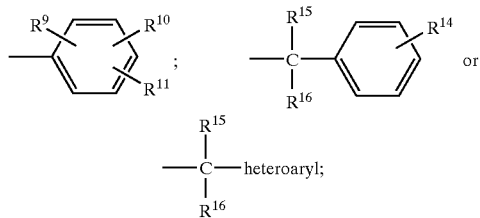

$R^3$ is hydrogen, $C_1$–$C_6$ alkyl, $(C_1$–$C_6)$alkoxy$(C_1$–$C_6)$ alkyl, $C_3$–$C_{10}$ cycloalkyl, $C_3$–$C_{10}$ cycloalkyl $(C_1$–$C_6$)alkyl, $R^8$-phenyl, $R^8$-phenyl$(C_1$–$C_6$ )alkyl, $R^8$-naphthyl, $R^8$-naphthyl$(C_1$–$C_6)$alkyl, $R^8$-heteroaryl or $R^8$-heteroaryl$(C_1$–$C_6)$alkyl;
$R^4$, $R^5$, $R^7$ and $R^{13}$ are independently selected from the group consisting of hydrogen and $(C_1$–$C_6)$-alkyl;
$R^6$ is hydrogen, $C_1$–$C_6$ alkyl or $C_2$–$C_6$ alkenyl;

$R^8$ is 1 to 3 substituents independently selected from the group consisting of hydrogen, halogen $C_1$–$C_6$ alkyl, $C_1$–$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$, $CH_3C(=NOCH_2CH_3)$

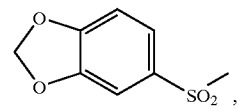

—$NH_2$, —$NHCOCF_3$, —$NHCONH(C_1$–$C_6$ alkyl), —$NHCO(C_1$–$C_6$ alkyl), —$NHSO_2(C_1$–$C_6$ alkyl), 5-membered heteroaryl and

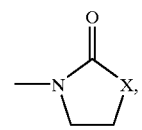

wherein X is —O—, —NH— or —$N(CH_3)$;
$R^{8a}$ is 1 to 3 substituents independently selected from the group consisting of hydrogen, halogen, —$CF_3$, $CF_3O$—, —CN, $CF_3SO_2$—, $R^{14}$-phenyl, —$NHCOCF_3$, 5-membered heteroaryl and

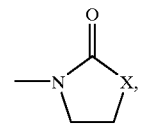

wherein X is as defined above;
$R^{8b}$ is 1 to 3 substituents independently selected from the group consisting of hydrogen, halogen, —$CF_3$, $CF_3O$—, $CH_3C(O)$—, —CN, $CF_3SO_2$—, $R^{14}$-benzyl, $CH_3C(=NOCH_3)$, $CH_3C(=NOCH_2CH_3)$,

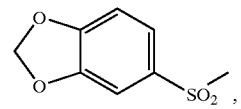

—$NHCOCF_3$, 5-membered heteroaryl and

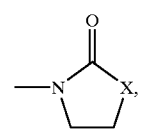

wherein X is as defined above;
$R^8$ and $R^{10}$ are independently selected from the group consisting of $(C_1$–$C_6)$alkyl, halogen, —$NR^{17}R^{18}$, —OH, —$CF_3$, —$OCH_3$, —O-acyl, —$OCF_3$ and —$Si(CH_3)_3$;
$R^{11}$ is $R^9$, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —$N(R^{17})$ $CONR^{18}R^{19}$, —NHCONH(chloro-$(C_1$–$C_6)$alkyl), —NHCONH$((C_3$–$C_1)$cycloalkyl$(C_1$–$C_6)$alkyl), —NHCO$(C_1$–$C_6)$alkyl, —$NHCOCF_3$, —$NHSO_2N$ $((C_1$–$C_6)$alkyl$)_2$, —$NHSO_2(C_1$–$C_6)$alkyl, —$N(SO_2CF_3)_2$, —$NHCO_2(C_1$–$C_6)$alkyl, $C_3$–$C_{10}$ cycloalkyl, —$SR^{20}$, —$SOR^{20}$, —$SO_2R^{20}$, —$SO_2NH$ $(C_1-C_6)$alkyl, $-OSO_2(C_1-C_6)$alkyl, $-OSO_2CF_3$, hydroxy$(C_1-C_6)$alkyl, $-CON\ R^{17}R^{18}$, $-CON(CH_2CH_2-O-CH_3)_2$, $-OCONH(C_1-C_6)$alkyl, $-CO_2R^{17}$, $-Si(CH_3)_3$ or $-B(OC(CH_3)_2)_2$;

$R^{12}$ is $(C_1-C_6)$alkyl, $-NH_2$ or $R^{14}$-phenyl;

$R^{14}$ is 1 to 3 substituents independently selected from the group consisting of hydrogen, $(C_1-C_6)$ alkyl, $-CF_3$, $-CO_2R_{17}$, $-CN$, $(C_1-C_6)$alkoxy and halogen;

$R^{15}$ and $R^{16}$ are independently selected from the group consisting of hydrogen and $C_1-C_6$ alkyl, or $R^{15}$ and $R^{16}$ together are a $C_2-C_5$ alkylene group and with the carbon to which they are attached form a spiro ring of 3 to 6 carbon atoms;

$R^{17}$, $R^{18}$ and $R^{19}$ are independently selected from the group consisting of H and $C_1-C_6$ alkyl; and $R^{20}$ is $C_1-C_6$ alkyl or phenyl; or (2) $R^a$ is $R^8$-phenyl, $R^8$-pyridyl or $R^8$-thiophenyl;

$R^2$ is fluorenyl, diphenylmethyl,

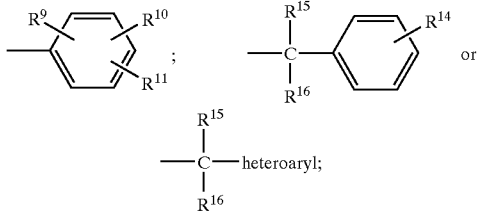

and $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are as defined in (1); in combination with one or more antiviral agents selected from the group consisting of nucleoside reverse transcriptase inhibitors, non-nucleoside reverse transcriptase inhibitors, protease inhibitors, hydroxyurea, ribavirin, IL-2IL-12, pentafuside and Yissum No. 11607.

2. The method of claim 1 wherein the antiviral agent is selected from the group consisting of nucleoside reverse transcriptase inhibitors, non-nucleoside reverse transcriptase inhibitors and protease inhibitors.

3. The method of claim 1 wherein the antiviral agent is selected from the group consisting of zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 11607 and AG-1549.

4. A method of treating Human Immunodeficiency Virus comprising administering to a human in need of such treatment a therapeutically effective amount of a CCR5 antagonist of the structural formula I:

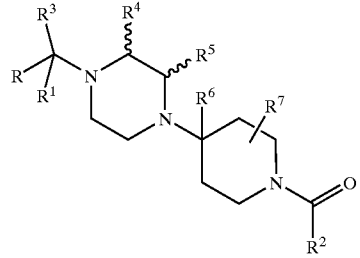

or a pharmaceutically acceptable salt thereof, wherein

R is $R^8$-phenyl, $R^8$-pyridyl, $R^8$-thiophenyl or $R^8$-naphthyl;

$R^1$ is hydrogen or $C_1-C_6$ alkyl;

$R^2$ is 6-membered heteroaryl substituted by $R^9$, $R^{10}$ and $R^{11}$; 6-membered heteroaryl N-oxide substituted by $R^9$, $R^{10}$ and $R^{11}$; 5-membered heteroaryl substituted by $R^{12}$ and $R^{13}$; naphthyl; fluorenyl; diphenylmethyl;

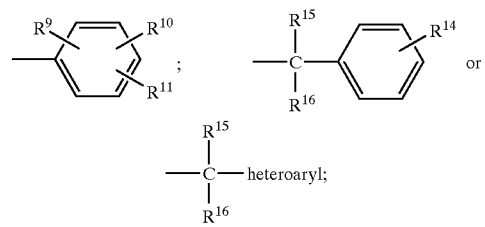

$R^3$ is hydrogen, $C_1-C_6$ alkyl, $(C_1-C_6)$alkyl, $C_3-C_{10}$ cycloalkyl, $C_3-C_{10}$ cycloalkyl$(C_1-C_6)$alkyl, $R^8$-phenyl, $R^8$-phenyl$(C_1-C_6)$alkyl, $R^8$-naphthyl, $R^8$-naphthyl$(C_1-C_6)$alkyl, $R^8$-heteroaryl or $R^8$-heteroeryl$(C_1-C_6)$alkyl;

$R^4$, $R^5$, $R^7$ and $R^{13}$ are independently selected from the group consisting of hydrogen and $(C_1-C_6)$-alkyl;

$R^6$ is hydrogen, $C_1-C_6$ alkyl or $C_2-C_6$ alkenyl;

$R^8$ is 1 to 3 substituents independently selected from the group consisting of hydrogen, halogen, $C_1-C_6$ alkyl, $C_1-C_6$ alkoxy, $-CF_3$, $CF_3O-$, $CH_3C(O)-$, $-CN$, $CH_3SO_2-$, $CF_3SO_2-$, $R^{14}$-phenyl, $R^{14}$-benzyl, $CH_3C(=NOCH_3)$, $CH_3C(=NOCH_2CH_3)$

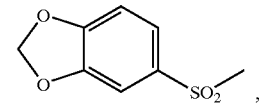

$-NH_2$, $-NHCOCF_3$, $-NHCONH(C_1-C_6\ alkyl)$, $-NHCO(C_1-C_6\ alkyl)$, $-NHSO_2(C_1-C_6\ alkyl)$, 5-membered heteroaryl and

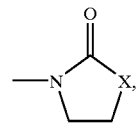

wherein X is $-O-$, $-NH-$ or $-N(CH_3)-$;

$R^9$ and $R^{10}$ are independently selected from the group consisting of $(C_1-C_6)$alkyl, halogen, $-NR^{17}R^{18}$, $-OH$, $-CF_3$, $-OCH_3$, $-O$-acyl, $-OCF_3$ and $-Si(CH_3)_3$;

$R^{11}$ is $R^9$, hydrogen, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —N($R^{17}$)$CONR^{18}R^{19}$, —NHCONH(chloro-($C_1$-$C_6$)alkyl), —NHCONH(($C_3$-$C_1$)cycloalkyl($C_1$-$C_6$)alkyl, —NHCO($C_1$-$C_6$)alkyl, —$NHCOCF_3$, —$NHSO_2$N(($C_1$-$C_6$)alkyl)$_2$, —$NHSO_2$($C_1$-$C_6$)alkyl, —N($SO_2CF_3$)$_2$, —$NHCO_2$($C_1$-$C_6$)alkyl, $C_3$-$C_{10}$ cycloalkyl, —$SR^{20}$, —$SOR^{20}$, —$SO_2R^{20}$, —$SO_2$NH($C_1$-$C_6$ alkyl), —$OSO_2$($C_1$-$C_6$)alkyl, —$OSO_2CF_3$, hydroxy($C_1$-$C_6$)alkyl, —CON $R^{17}R^{18}$, —CON($CH_2CH_2$—O—$CH_3$)$_2$, —OCONH($C_1$-$C_6$)alkyl, —$CO_2R_{17}$, —Si($CH_3$)$_3$ or —B(OC($CH_3$)$_2$)$_2$;

$R^{12}$ is ($C_1$-$C_6$)alkyl, —$NH_2$ or $R^{14}$-phenyl;

$R^{14}$ is 1 to 3 substituents independently selected from the group consisting of hydrogen, $C_1$-$C_6$ alkyl, —$CF_3$, —$CO_2R_{17}$, —CN, ($C_1$-$C_6$)alkoxy and halogen;

$R^{15}$ and $R^{16}$ are independently selected from the group consisting of hydrogen and $C_1$-$C_6$ alkyl, or $R^{15}$ and $R^{16}$ together are a $C_2$-$C_5$ alkylene group and with the carbon to which they are attached form a spiro ring of 3 to 6 carbon atoms;

$R^{17}$, $R^{18}$ and $R^{19}$ are independently selected from the group consisting of H and $C_1$-$C_6$ alkyl; and $R^{20}$ is $C_1$-$C_6$ alkyl or phenyl, in combination with one or more antiviral agents selected from the group consisting of nucleoside reverse transcriptase inhibitors, non-nucleoside reverse transcriptase inhibitors, protease inhibitors, hydroxyurea, ribavirin, IL-2, IL-12, pentafuside and Yissum No. 11607.

5. The method of claim 4 wherein R is $R^8$-phenyl or $R^8$-naphthyl.

6. The method of claim 5 wherein R is

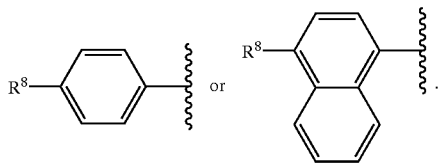

7. The method of claim 4 wherein $R^3$ is hydrogen, ($C_1$-$C_6$) alkyl, $R^8$-phenyl, $R^8$-benzyl or $R^8$-pyridyl.

8. The method of claim 4 wherein $R^1$ is hydrogen and $R^6$ is hydrogen or methyl.

9. The method of claim 4 wherein $R^2$ is

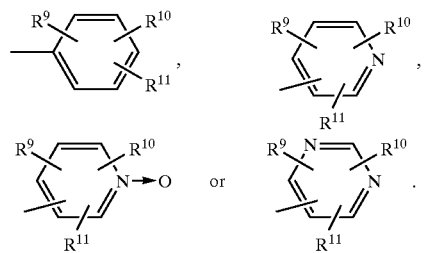

10. The method of claim 9 wherein $R^2$ is selected from the group consisting of

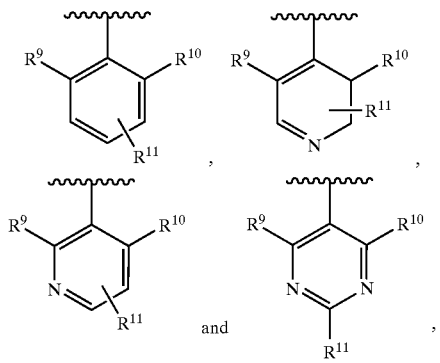

wherein $R^9$ and $R^{10}$ are selected from the group consisting of ($C_1$-$C_6$)alkyl, halogen, —OH and —$NH_2$.

11. The method of claim 10 wherein $R^2$ is phenyl or pyridyl and $R^{11}$ is hydrogen, or wherein $R^2$ is pyrimidyl and $R^{11}$ is hydrogen, methyl or phenyl.

12. The method of claim 4 wherein the antiviral agent is selected from the group consisting of nucleoside reverse transcriptase inhibitors, non-nucleoside reverse transcriptase inhibitors and protease inhibitors.

* * * * *

UNITED STATES PATENT AND TRADEMARK OFFICE
CERTIFICATE OF CORRECTION

PATENT NO. : 6,689,765 B2
DATED : February 10, 2004
INVENTOR(S) : Bahige M. Baroudy et al.

It is certified that error appears in the above-identified patent and that said Letters Patent is hereby corrected as shown below:

Column 124,
Line 55, change "$R^8$" to read -- $R^9$ --.

Line 63, change 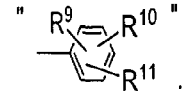 to read
-- -NHCONH(($C_3$-$C_{10}$)cycloalkyl($C_1$-$C_6$)alkyl --.

Column 125,
Line 41, change "IL-2IL12" to read -- IL-2, IL-12 --.

Column 126,
Line 25, delete 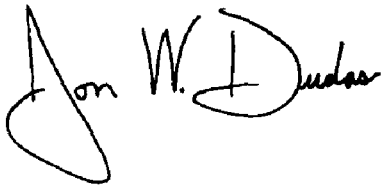 .

Line 33, in the first line of the definition of $R^3$, insert
-- ($C_1$-$C_6$)alkoxy -- before "($C_1$-$C_6$)alkyl"

Signed and Sealed this

Thirty-first Day of August, 2004

JON W. DUDAS
*Director of the United States Patent and Trademark Office*